(12) United States Patent
Phillips et al.

(10) Patent No.: US 6,492,023 B1
(45) Date of Patent: Dec. 10, 2002

(54) BUNDLES OF FIBERS USEFUL FOR MOVING LIQUIDS AT HIGH FLUXES AND ACQUISITION/DISTRIBUTION STRUCTURES THAT USE THE BUNDLES

(75) Inventors: Bobby Mal Phillips, Jonesborough, TN (US); Jackson Lee Nelson, Johnson City, TN (US); Shriram Bagrodia, Kingsport, TN (US)

(73) Assignee: Clemson University Research Foundation, Clemson, SC (US)

( * ) Notice: Subject to any disclaimer, the term of this patent is extended or adjusted under 35 U.S.C. 154(b) by 97 days.

(21) Appl. No.: 09/693,859

(22) Filed: Oct. 20, 2000

Related U.S. Application Data

(62) Division of application No. 09/439,744, filed on Nov. 15, 1999, now Pat. No. 6,387,493, which is a division of application No. 08/912,608, filed on Aug. 15, 1997, now Pat. No. 6,103,376.
(60) Provisional application No. 60/024,301, filed on Aug. 22, 1996.

(51) Int. Cl.$^7$ ................................................. D02G 3/00
(52) U.S. Cl. ....................... 428/397; 428/357; 428/400; 428/401
(58) Field of Search ............................... 428/375, 357, 428/397, 480, 482, 400, 401

(56) References Cited

U.S. PATENT DOCUMENTS

| | | | |
|---|---|---|---|
| 3,121,040 A | 2/1964 | Shaw et al. ................. 161/177 |
| 3,405,424 A | 10/1968 | Imobersteg et al. ............. 18/8 |
| 3,616,633 A | 11/1971 | Chevalier-Seyvet et al. ............... 57/140 J |
| 4,129,679 A | 12/1978 | Woodings | |
| 4,245,001 A | 1/1981 | Phillips et al. .............. 428/224 |
| 4,321,924 A | 3/1982 | Ahr ........................... 128/287 |
| 4,324,247 A | 4/1982 | Aziz .......................... 128/287 |
| 4,332,761 A | 6/1982 | Phillips et al. .............. 264/147 |
| 4,476,079 A | 10/1984 | Phillips ...................... 264/154 |
| 4,829,761 A | 5/1989 | Phillips et al. ................ 57/248 |
| 4,954,398 A | 9/1990 | Bagrodia et al. ............. 428/400 |
| 5,057,368 A | 10/1991 | Largman et al. .............. 428/397 |
| 5,200,248 A | 4/1993 | Thompson et al. ........... 428/131 |
| 5,242,644 A | 9/1993 | Thompson et al. ......... 264/177 |
| 5,263,845 A | 11/1993 | Warren ....................... 425/461 |
| 5,268,229 A | 12/1993 | Phillips et al. .............. 428/400 |
| 5,275,859 A | 1/1994 | Phillips et al. ................ 428/65 |
| 5,314,743 A | 5/1994 | Meirowitz et al. ........... 428/297 |
| 5,334,176 A | 8/1994 | Buenger et al. .............. 604/367 |
| 5,342,336 A | 8/1994 | Meirowitz et al. ........... 604/378 |
| 5,346,422 A | 9/1994 | Bagrodia et al. ............ 446/394 |
| 5,368,926 A | 11/1994 | Thompson et al. .......... 428/284 |
| 5,387,469 A | 2/1995 | Warren ....................... 428/397 |
| 5,458,835 A | 10/1995 | Wilkes et al. ............... 264/143 |
| 5,458,963 A | 10/1995 | Meirowitz et al. ........... 428/297 |
| 5,611,981 A | 3/1997 | Phillips et al. .............. 264/130 |
| 5,634,914 A | 6/1997 | Wilkes et al. ............... 604/375 |
| 5,648,142 A | 7/1997 | Phillips ...................... 428/132 |
| 5,723,159 A | 3/1998 | Phillips et al. .............. 425/461 |
| 5,837,625 A | 11/1998 | Phillips et al. .............. 442/337 |
| 5,972,505 A * | 10/1999 | Phillips et al. .............. 428/397 |
| 5,977,429 A | 11/1999 | Phillips et al. .............. 604/370 |
| 6,251,322 B1 | 6/2001 | Phillips et al. .............. 264/103 |

FOREIGN PATENT DOCUMENTS

| | | |
|---|---|---|
| EP | 0 301 874 | 2/1989 |
| EP | 0 391 814 A | 10/1990 |
| EP | 0 493 728 | 7/1992 |
| EP | 0 516 730 B1 | 12/1992 |
| EP | 0 547 498 | 6/1993 |
| GB | 2 225 724 A | 6/1990 |
| WO | WO 91 12949 A | 9/1991 |
| WO | WO 92 00407 A | 1/1992 |
| WO | WO 93 01779 A | 2/1993 |
| WO | WO 93 01780 A | 2/1993 |
| WO | WO 93 02235 A | 2/1993 |
| WO | WO 94 05245 A | 3/1994 |
| WO | WO 95 00093 | 1/1995 |
| WO | WO 96 04876 | 2/1996 |

OTHER PUBLICATIONS

Patent Abstracts of Japan vol. 095, No. 009, Oct. 31, 1995 & JP 07 148876 A (Shinshiyou KK; Others: 01), Jun. 13, 1995; see abstract.
Patent Abstracts of Japan vol. 095, No. 005, Jun. 30, 1995 & JP 07 034341 A (Toray Ind. Inc.), Feb. 3, 1995; see abstract.

\* cited by examiner

*Primary Examiner*—Cynthia H. Kelly
*Assistant Examiner*—B. Shewareged
(74) *Attorney, Agent, or Firm*—Kennedy Covington Lobdell & Hickman, LLP

(57) ABSTRACT

The ability to transport body liquids in consumer products such as diapers, incontinents and feminine napkins is a key factor in their performance. This invention is designed to provide specific high fluxes (volume of liquid/(time*mass of polymer) of aqueous liquids in designated directions using bundles of new specially designed fibers. The key factors for the bundles are a high specific adhesion for the liquid of interest, a high specific volume of the bundle itself, and alignment of the fibers within the bundle. The invention includes novel liquid acquisition/distribution systems and absorbent products that include a liquid acquisition/distribution system which may incorporate the novel bundles of fibers.

11 Claims, 59 Drawing Sheets

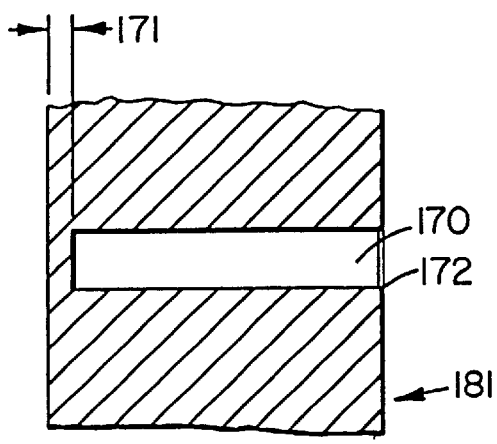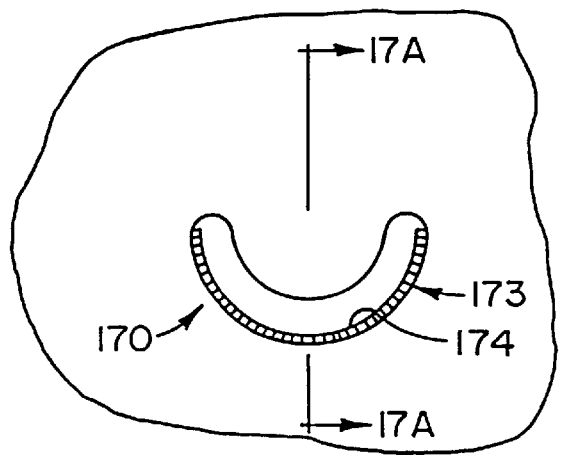
Fig. 17A          Fig. 17B
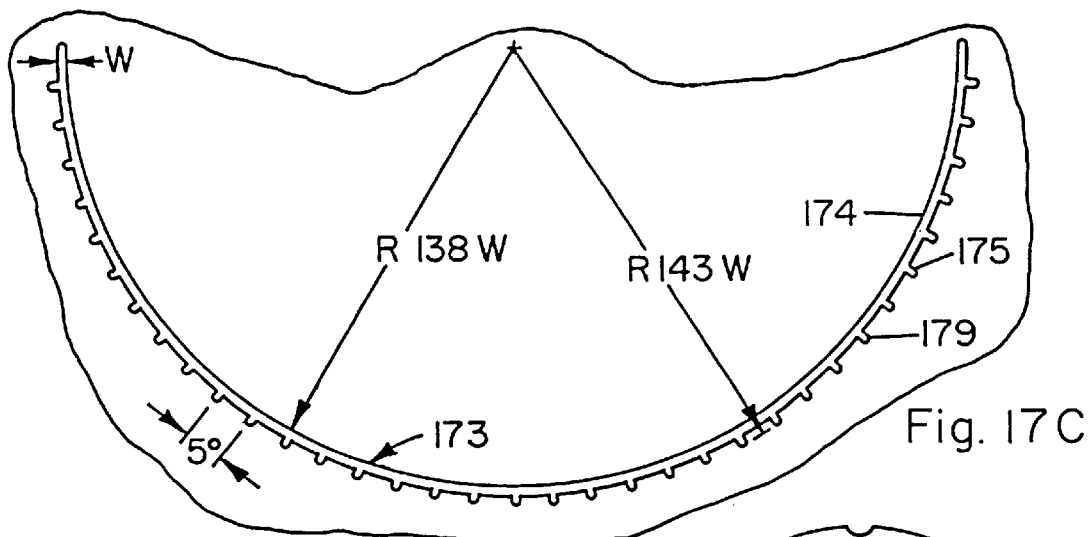
Fig. 17C
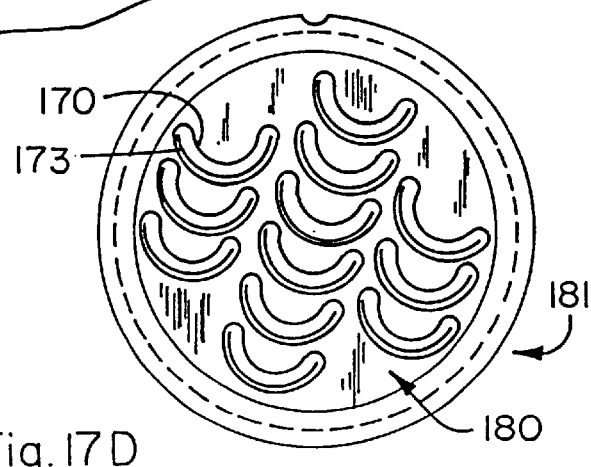
Fig. 17D

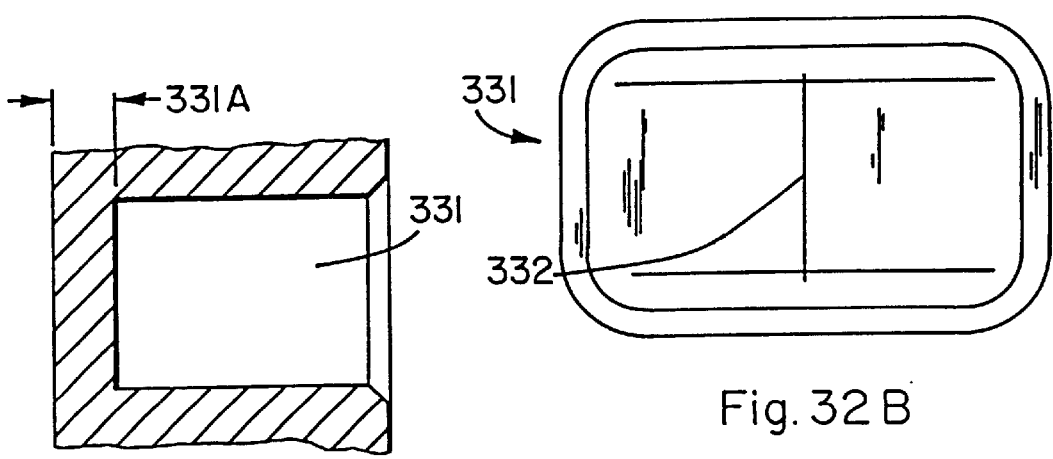
Fig. 32A
Fig. 32B
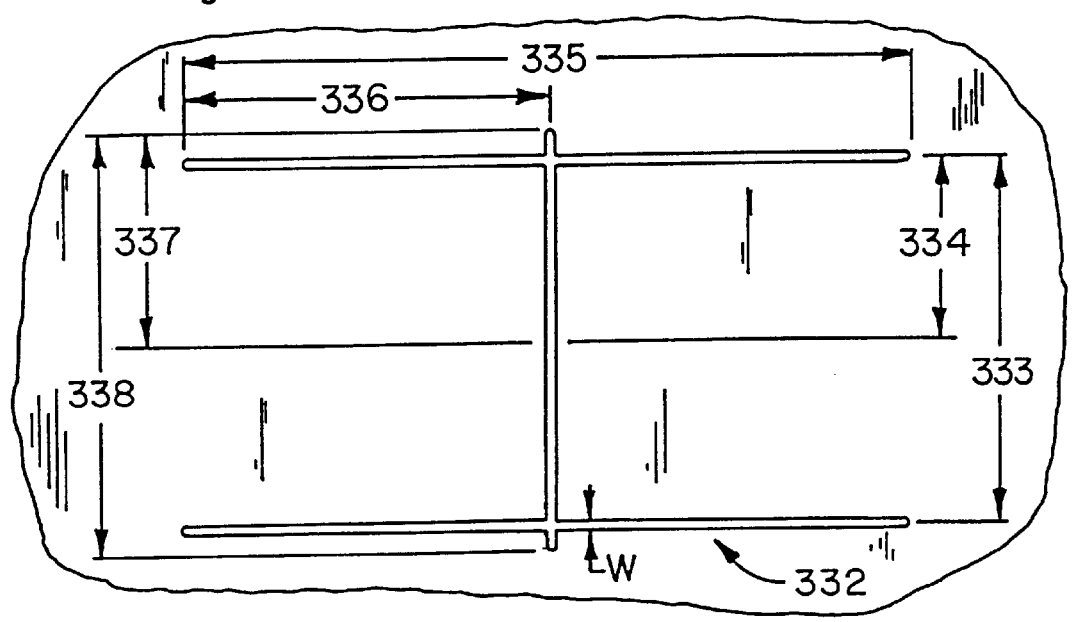
Fig. 32C
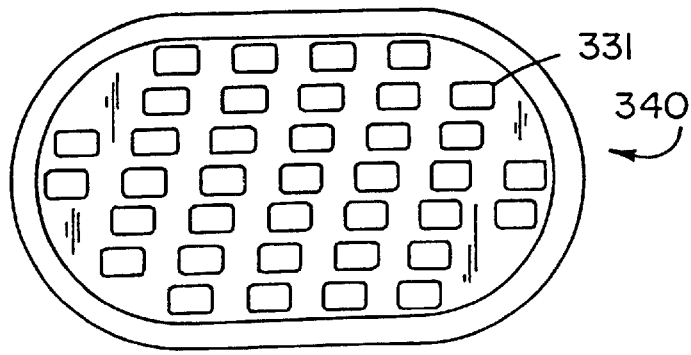
Fig. 32D

530

BUNDLES OF FIBERS USEFUL FOR MOVING LIQUIDS AT HIGH FLUXES AND ACQUISITION/DISTRIBUTION STRUCTURES THAT USE THE BUNDLES

CROSS-REFERENCES TO RELATED APPLICATIONS

This is a divisional application Ser. No. 09/439,744, filed Nov. 15, 1999, now U.S. Pat. No. 6,387,493, which claims priority from and is a divisional application Ser. No. 08/912,608, filed Aug. 15, 1997, issued as U.S. Pat. No. 6,103,376, which claims benefit of Provisional Application Serial No. 60/024,301 filed Aug. 22, 1996.

TECHNICAL FIELD

This invention relates to structures that transport liquids by capillary action. More particularly, this invention relates to fibers and personal hygiene absorbent products such as diapers, adult incontinent pads, and feminine napkins, and to the flow, distribution, and acquisition of liquids in the fibers and products.

BACKGROUND OF THE INVENTION

In the past several years there has been great interest in polymer structures that provide liquid transport and storage.

U.S. Pat. No. 5,200,248 to Thompson et al. issued Apr. 6, 1993 and discloses capillary channel structures such as fibers that include intrastructure capillary channels that store and transport liquid. The Thompson et al. patent disclosed that these capillary channel fibers may be coated with materials that provide an adhesion tension with water of at least 25 dynes/cm. The teachings and especially the definitions in the Thompson et al. patent are hereby incorporated by reference as if fully set forth herein. This specification provides values for fibers shown in examples herein for some of the quantities defined in the Thompson et al. patent.

European patent application No. EP 0 516 730 B1 claims priority from the application that matured into the Thompson et al. patent.

U.S. Pat. No 5,611,981 to Phillips et al. issued Mar. 18, 1997 discloses spontaneously wettable fibers having a combination of X values and surface contact angles that satisfy conditions for spontaneous wetting. The X factor is defined therein as $X=P_w/(4r+(\pi-2)D)$ where $P_w$ is the wetted perimeter of the filament, r is the radius of the circumscribed circle circumscribing the fiber's cross-section, and D is the minor axis dimension across the fiber's cross-section. The teachings of and especially the definitions in the Phillips '981 patent are hereby incorporated herein by reference as if fully set forth herein. This specification discloses values for fibers shown in examples herein for some of the quantities defined in the Phillips '981 patent.

U.S. Pat. No. 5,268,229 to Phillips et al. issued Dec. 7, 1993 discloses specific "U" and "E" shaped cross-sections of spontaneously wettable fibers with stabilizing legs.

U.S. Pat. No. 5,314,743 discloses non-woven webs made from capillary channel fibers.

U.S. Pat. No. 3,121,040 to Shaw et al. discloses "+" and "Y" shaped polyolefin fibers with arm length/arm width ratios greater than 4. These fibers are so thick and large that they are too stiff for use in consumer disposables. The smallest arm width disclosed in the Shaw et al. patent is about 75 microns.

International patent application PCT/US95/08896 discloses a structure that is capable of transporting liquids by intercapillary action using essentially parallel fibers, and discloses that the driving force on the liquid is directed from the open areas to the closed areas.

U.S. Pat. No. 4,829,761 to Phillips et al. issued May 16, 1989 discloses-continuous filament yarns. The teachings of and especially the definitions in that patent are hereby incorporated herein by reference as if fully set forth herein. This specification provides values for fibers shown herein for the specific volume quantity defined in the Phillips '761 patent. U.S. Pat. No. 4,245,001 to Phillips et al. also discloses the specific volume quantity, and its teachings are also incorporated by reference as if fully set forth herein. The specific volume is defined in the Phillips '761 patent in units of cubic centimeters per gram as 8.044 divided by the weight of the yarn in grams when the yarn is under a tension of 0.1 grams per denier for a volume of yarn filling an 8.044 cubic centimeter volume. Thus, the specific volume is the volume per gram of material in a volume of space when the fibers of the yarn are pressed against one another in the volume of space and are under a defined tension.

Much of the interest in polymer structures that absorb and transport liquid is because of their applicability in consumer disposable products. The inventors view absorbent cores of modern consumer disposable products including diapers, adult incontinent pads, and feminine napkins, as having three primary functions; acquisition, distribution, and storage of liquids. The distribution function is typically poorly executed with current absorbent core components such as fluff pulp and/or super absorbent polymer. As a consequence, excessive leakage and poor utilization of the absorbent core material relative to the theoretical maximum absorbent capacity of the absorbent core material are problems limiting the performance of these consumer disposables.

Poor distribution occurs because the components of the core are typically good at storing liquids but poor at distributing them. Many attempts have been made in the prior art to solve this problem.

International Patent Application No. WO 95/00093 dated Jan. 5, 1995 discloses a sanitary pad with a liquid directing strip and an absorbent strip positioned under a top sheet.

U.S. Pat. No. 5,342,336 to Meirowitz et al. issued Aug. 30, 1994 and discloses a structure for absorbing and transporting a liquid that includes shaped staple fibers to move liquids more toward the ends of the pad. Typically, staple fibers are less than two inches long.

U.S. Pat. No. 4,324,247 to Aziz issued Apr. 13, 1982 and discloses an absorbent article including a top sheet, an absorbent core, and a perforated thermoplastic film between the top sheet and the absorbent core. The Aziz patent teaches that its structure prevents liquid in the core from flowing out of the absorbent core back to the top sheet when the structure is squeezed.

U.S. Pat. No. 4,321,924 to Ahr issued Mar. 30, 1982 and discloses an absorbent article including a top sheet, a layer of fibers affixed to the inner surface of the top sheet, the fiber layer overlaying an intermediate layer having a multiplicity of tapered capillaries, and an absorbent core. The Ahr patent asserts that the Ahr structure provides improved acquisition and reduced re-wetting.

United Kingdom Patent Application GB 2,225,724A was published Jun. 13, 1990 and discloses an absorbent device that includes a liquid pervious cover sheet, an absorbent core, and a liquid pervious intermediate layer that is between the absorbent core and the cover sheet and that has apertures and contours. This patent application asserts that its structure provide reduced re-wetting.

U.S. patent application Ser. No. 545,450 filed Oct. 19, 1995 discloses an apertured film with cut out portions in the apertured walls to provide spontaneous liquid inversion from the front side of the top sheet to the backside of the top sheet. The teachings of the '450 application are hereby incorporated by reference as if fully set forth herein and may be used in conjunction with the absorbent product inventions defined herein.

Thus, there is a general ongoing desire in the art to increase the absorbent capacity and the liquid transport capacity of polymer material for various applications. There is a more specific continuing need in the art for a family of acquisition/distribution structures which can better transport and distribute liquids in disposable absorbent products. Accordingly, it is to the provision of such that the present invention is primarily directed.

Further, it is to be understood that the inventors conceive of additional applications relating to the novel transport ability of the basic fiber structures disclosed herein including filtering of liquids and suspensions, horizontal transport of liquids, and vertical transport of liquids.

SUMMARY OF THE INVENTION

The invention is a bundle of synthetic fibers for transporting fluids. The bundle comprises at least two fibers that when acting as individual fibers are poor transporters of fluids, yet when in a bundle the fibers provide a bundle that is an excellent transporter of fluids. The bundles are useful in absorbent articles such as diapers, incontinents and feminine hygiene products.

The bundle has a Specific Volume greater than 4.0 cubic centimeters per gram (cc/gm), an average inter-fiber capillary width of from 25 to 400 microns, and a length greater than one centimeter (cm). Preferably, the fluid to be transported is aqueous and the movement of fluid in the bundle is measured according to the following parameters as defined herein: a $MPF_B/MPF_{SF}$ greater than or equal to 3.0, a $MPF_B$ greater than or equal to 0.14 cubic centimeters per denier per hour (cc/(den*hr)), a $VR_B/VR_{SF}$ greater than or equal to 1.3, and a $VR_B$ greater than or equal to 4.0 centimeters (cm).

At least one of the two fibers has a non-round cross-section, a Single Fiber Bulk Factor greater than 4.0, a Specific Capillary Volume less than 2.0 cc/gm or a Specific Capillary Surface Area less than 2000 cc/gm, and more than 70% of intra-fiber channels having a capillary channel width greater than 300 microns. Preferably, the cross-section defines a first arm having a length greater than 40 microns. The lengths of the cross-section of the fibers range up to almost 1000 microns with some of the examples having arm lengths that are between 100 and 400 microns. Preferably, the fibers have a denier (den) between 15 and 250. The cross-section and the surface composition of the non-round fibers preferably satisfy the inequality: $(P\gamma \cos(\theta a))/d > 0.03$ dynes/den, wherein P is the perimeter of the cross-section of the fiber, $\gamma$ is the surface tension of the liquid, ($\theta a$) is the advancing contact angle of the liquid measured on a flat surface made from the same material as the fiber and having the same surface treatment and d is the denier of the fiber.

Further, the invention includes the novel spinnerettes used to make the fibers of the bundles. Those spinnerettes are characterized by very large ratios of the length to the width of the aperture of the spinnerette and large absolute lengths of sections of the aperture of the spinnerette. Preferably, the length to width ratios of a section of the spinnerette is greater than 40, more preferably greater than 60, and even more preferably greater than 100. The length to width ratio of individual cross-section segments (e.g., legs, arms) may be between 40 and about 150.

Further, the process of making the fibers of the present invention includes heating the polymer to between 270° and 300° centigrade and extruding the heated polymer through an aperture having a width of less than 0.12 millimeters (mm) and a total length of at least 50 times the width.

Further, liquid acquisition/distribution structures are included in the invention which comprise a top layer that is permeable to a liquid, a distribution layer, and a resistance layer. The distribution layer comprises a capillary system providing capillary forces on the liquid when the liquid is in contact with the distribution layer tending to transport the liquid parallel to the top layer. The resistance layer has a resistance layer top surface and a resistance layer bottom surface. The resistance layer provides resistance to transmission of the liquid from the resistance layer top surface to the resistance layer bottom surface. An absorbent core may also be added to the structures which may be beneath the resistance layer or partially surrounded by the distribution layer and the resistance layer.

BRIEF DESCRIPTION OF THE DRAWINGS

FIG. 17A is a partial sectional view of a bore detail for an aperture of a spinnerette used in example 9;

FIG. 17B is a plan view of a bore and an aperture of the spinnerette used in example 9;

FIG. 17C is a schematic showing the dimensions of the aperture of the spinnerette used in example 9;

FIG. 17D is a plan view of an interior face of the spinnerette used in example 9 showing a bore and an aperture pattern;

FIG. 32A is a partial side sectional view of the bore for an aperture of the spinnerette used in example 13;

FIG. 32B is a schematic plan view of a bore and an aperture of the spinnerette used in example 13;

FIG. 32C is a schematic showing the dimensions of an aperture of the spinnerette used in example 13;

FIG. 32D is a plan view of an interior face of the spinnerette used in example 13 showing a bore and an aperture pattern;

DETAILED DESCRIPTION OF THE INVENTION

Figure 1A:
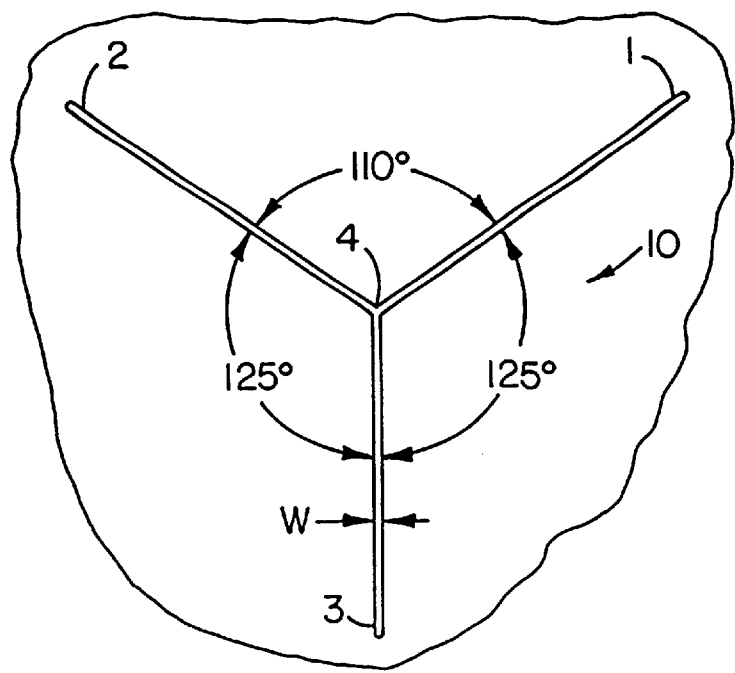
FIG. 1A is a schematic identifying relative dimensions of an aperture of a spinnerette used in example 1.

The present invention is a bundle of synthetic fibers which, when wetted, is capable of transporting liquid along its length at a relatively large liquid flux as compared to the liquid flux associated with an individual fiber in the bundle. In other words, the bundle consists of fibers which individually are poor liquid transporters or which have no "capillary channels" on their surfaces, i.e have no intra-fiber capillary channels. This unexpected improved liquid transport that the bundles provide over the individual fibers that are poor liquid transporters is a phenomenon resulting from a novel combination of fiber and bundle structure, which create inter-fiber capillaries, and surface composition of the fibers.

The term "capillary channels" as used herein refers to prior art definitions of this term wherein channels having a width of about less than 300 microns, preferably 250 microns, are considered capillary channels since the capillary forces acting within the channels are much greater than the force of gravity.

Bundle Structure

As used herein, the term "bundle" refers to two or more synthetic fibers, preferably 8 to 50,000 fibers, that have a length greater than one centimeter, are aligned on the average parallel with one another and have inter-fiber capillaries. An average inter-fiber capillary width, D, of the bundles of fibers is about 25 to 400 microns, preferably 60 to 300 microns and more preferably 100 to 300 microns. The average inter-fiber capillary width, D, is defined by the following equation:

$$D = \frac{4(SV - 1/\rho_P) * dpf * 10^3}{9P};$$

wherein SV is the Specific Volume of the bundle of fibers (cc/gm), $\rho_p$ is the density of the polymer from which the fiber is made (gm/cc), dpf is the average denier (den) of the individual fiber (gms/9000 meters of a single fiber) and P is the average perimeter of the cross-section of the individual fibers (microns).

SV is measured using the procedure described in U.S. Pat. No. 4,829,761 except that the tension used to define SV herein is 0.05 gm/den instead of the 0.10 gm/den for the '761 patent. The bundle is wound at a specified tension of 0.05 grams/den into a cylindrical slot of known volume (normally 8.044 cc). The bundle is wound until the known volume of the slot is completely filled by winding of the bundle. The weight of the bundle contained in the slot is determined to the nearest 0.1 milligram (mg). The specific volume is then defined as the ratio of the known volume to the weight of the bundle in the slot, which may be represented as $$SV \text{ (at 0.05 gm/den tension)} = \frac{8.044 \text{ cc}}{\text{wt of yarn in gms}}.$$

The bundle of synthetic fibers of the invention provide the following two properties:

$MPF_B > 0.14 \text{cc}/(\text{den}*\text{hr})$  1.

and $$\frac{MPF_B}{MPF_{SF}} \geq 3 \qquad 2.$$

wherein Maximum Potential Flux (MPF) is a measure of maximum volume of liquid transported per denier of the fiber (or fibers) forming the capillary (or capillaries) per unit of time. All MPF values in this application are in units of cubic centimeters per denier per hour (cc/(den*hr)). The test liquid utilized in the measure of MPF for data in this specification must be either (1) Syltint® Red Fugitive Tint, commercially available from Milliken Chemical, a division of Milliken & Company of Inman, S.C. or (2) Red Test Solution as described in detail below. Both test liquids are dark colored aqueous solutions which make them visually observable. Syltint® Red has a surface tension of about 54 dynes/cm and a shear viscosity of about 1.5 centipoise. Red Test Solution has a surface tension of about 54 dynes/cm and a shear viscosity of about 1.5 centipoise. Shear viscosity is measured at 25° C. using a Cannon-Ubbelohde Calibrated Viscometer. The procedure for obtaining MPF values is discussed in detail below.

MPF is a quantity that indicates the effectiveness of a fiber or a bundle of fibers in transporting liquid per weight of the fibers. The subscript "SF" refers to the MPF of a single fiber. The subscript "B" refers to the MPF of a bundle of fibers. The MPF values are based upon the net liquid flux propagating along both directions of the fiber or bundle of fibers. Because the flux is a property in one direction, there is a factor of two appearing in the definition of MPF to account for the movement of liquid in both directions away from where it contacts the bundle. This is sometimes referred to as "two-way" MPF to emphasize the factor of two in the definition. Thus, $MPF_B$ means MPF for a bundle of fibers, and $MPF_{SF}$ means MPF for a single fiber (i.e., a filament).

The $MPF_B/MPF_{SF}$ ratio refers to the $MPF_{SF}$ for a single fiber that is essentially identical (i.e., having the same surface morphology shape and the same composition) as fibers forming the bundle having the $MPF_B$. A bundle may be formed from fibers having different shaped cross-sections. For such a bundle that is formed from fibers having different shaped cross-sections, an effective $MPF_b/MPF_{SF}$ ratio can be calculated by averaging the $MPF_{SF}$ values for the fibers forming the bundle and using the averaged value for $MPF_{SF}$ in the ratio for $MPF_b/MPF_{SF}$. Reference hereinafter to the $MPF_B/MPF_{SF}$ ratio includes the effective ratio for bundles formed from fibers having different shaped cross-sections.

For a bundle of N fibers, $MPF_B$ is defined by the equality:

$$MPF_B = 8 \times 10^{-4} * Vo_N * SV * \left(1 - \frac{1}{\rho_p * SV}\right),$$

which is in cubic centimeters per denier per hour, wherein N is the number of the fibers in the bundle; $Vo_N$ is the initial velocity of the liquid in the N fiber bundle in millimeters per second (mm/s) measured according to the procedures described below; SV is the specific volume of the bundle; and $\rho_p$ is the density of the polymer forming the fibers of the bundle (gm/cc). For example, the maximum potential flux for a bundle of eight fibers is:

$$MPF_B = 8 \times 10^{-4} * Vo_8 * SV * \left(1 - \frac{1}{\rho_p * SV}\right),$$

wherein $Vo_8$ is the defined quantity called "Initial Velocity" of the liquid moving along a bundle of eight fibers in millimeters per second; SV is the specific volume of the bundle of fibers in cubic centimeters per gram at a tension of 0.05 gm/den, $\rho_p$ is the density of the polymer used to make the fibers of the bundle of eight fibers (gm/cc). All values for $MPF_B$ herein are based on Vo for a bundle of eight fibers. The use of a bundle of eight fibers as the basis for measuring Vo of the present invention is an arbitrary number. The reason that a bundle of eight fibers is used in the procedures for determining MPF relates to the ease with which liquid transport properties of a bundle of eight fibers and a single fiber can be measured with the same instrument, not because a bundle of eight fibers is more effective at transporting liquid than a bundle of a larger number of fibers.

The two-way $MPF_{SF}$ for a single fiber is defined in cubic centimeters per denier per hour as:

$MPF_{SF}=2*0.1620*Vo*(capillary\ channel\ area\ for\ flow)*1/dpf,$ wherein Vo (mm/sec) is the Initial Velocity of the liquid and dpf is the denier of the single fiber (gm/9000 m). The capillary channel area for flow (microns$^2$) is defined hereinbelow in the discussion of FIGS. 35–37C.

The $MPF_B$ for embodiments of the present invention ranges from 0.14 to 2.0 cc/(den*hr) and preferably from 0.2 to 2.0 cc/(den*hr). Since the $MPF_B$ is the movement of fluid along the bundle, the higher this value the better. Thus, the value for $MPF_B$ which represents bundles of fibers of this invention is simply greater than 0.14 cc/(den*hr), more preferably greater than 0.2 cc/(den*hr). The examples disclosed herein have $MPF_B$ for eight fiber bundles of between about 0.06 and about 0.36. The ratio of $MPF_B/MPF_{SF}$ is from 3 to 28. Preferably the ratio is greater than 5 and more preferably greater than 11.

Another measure of the properties of the bundles of synthetic fibers is the ratio of the height of the vertical rise of the test liquid, i.e. Syltint® Red or Red Test Solution, up along the bundle from a reservoir of the test liquid and against the pull of gravity to the height of the vertical rise of the test liquid up along a single fiber of the same type of fibers as the fibers forming the bundle and against the pull of gravity. The vertical rise measurement for a bundle of fibers of the present invention satisfies the inequality:

$$\frac{\text{Vertical Rise (Bundle)}}{\text{Vertical Rise (Single Fiber)}} \geq 1.3,$$

wherein Vertical Rise (VR) means the distance the test liquid rises above the level of the liquid to which the fiber or the bundle of fibers is in contact. Vertical Rise is reported herein in centimeters (cm) for a period of fifteen minutes unless otherwise specified. The ratio $VR_B/VR_{SF}$ is from 1.3 to 11.7, preferably greater than 2 and more preferably greater than 2.3. $VR_B$ is preferably greater than 4 cm and $VR_{SF}$ is preferably less than 4 cm.

The length of the bundle depends upon the length of liquid transport required for the desired application. Preferably, the bundle is at least one centimeter long. More preferably, the bundle is at least five centimeters long. For diapers, feminine napkins, and incontinent pads, the desired liquid transport lengths range from about 5 centimeters to about 40 centimeters. The bundle length is usually about twice the maximum transport length over which it is intended that the liquid be transported. This is because the liquid insults are designed to be near the centers of most absorbent products.

Preferably, when the bundle is wetted, at least one half of the fibers of the bundle contact at least one other fiber of the bundle on an average of at least once per centimeter. More preferably, when the bundle is wetted, each of the fibers of the bundle contact at least one other fiber of the bundle on an average of at least once per centimeter.

Preferably, tangents to the longitudinal axis of each of the fibers of a bundle are within 30° to one another along at least one half the length of the bundle. However, bundles of fibers that split at some point into two or more bundles that are not aligned with one another but otherwise meet the criteria indicated above are within the scope of this invention.

To ensure contact between fibers of the bundle when the bundle is not wetted, the fibers may be held together by a slight stickiness resulting from an anti-static or a hydrophilic finish if such a finish is present, by a crimp in the fiber that mechanically constrains the fibers of the bundle relative to one another, or merely by the placement of the fibers aligned adjacent one another when there are no substantial attractive or repulsive forces on the fibers of the bundle.

The fibers of the bundle do not necessarily have a unique cross-sectional orientation relative to one another. That is, since the fibers of the bundle are not necessarily rigidly connected to one another, there may be rotations of the cross-sections or local misalignments of the fibers along their lengths. Their orientations relative to one another along their length may be random or the bundles may be minimally twisted. There is no requirement of a fixed spatial relationship between the fibers of the bundle when the bundle is not wetted in order to provide the large liquid flux when the bundle is wetted. Thus, any bundle of fibers pressed against one another that provides an average inter-fiber capillary width of from 25 to 400 microns and has a specific volume greater than 4.0 cc/gm is within the scope of the present invention.

For purposes of further explaining the invention, one idealized structure is a bundle of fibers that when wetted and thereby pressed together define (at least) one inter-fiber capillary channel that has parallel walls, in which the inter-fiber capillary channel's walls are spaced from one another by the average inter-fiber capillary widths indicated above due to some sort of standoff structure, and in which the standoff structure is part of the cross-section of at least some of the fibers of the bundle.

Fiber Structure

The individual fibers of the present invention are shaped fibers having thin armed cross-sections. The term "shaped" fibers means fibers with non-round cross-sections. A single fiber has at least one channel that has walls defined by line segments of the cross-section of the fiber. The channel width of a channel of a single fiber is the length of a line segment tangent to the distal tips of the channel walls. The majority of the channel widths are preferably greater than 300 microns, which is relatively large as compared to channel widths for fibers of the prior art classified as having intra-fiber capillary channels.

The line segments of the cross-section, which define the channel walls, may be adjacent planar sections that in cross-section are aligned at greater than 60°, greater than 90°, or even greater than 120° relative to one another. For example, the planar sections may create a channel having two walls which join one another at a "V" shaped intersection or may also include a base region to which proximal ends of the two walls join. Moreover, the surface of the channel may be curved and therefore have no planar section defining a channel wall.

A quantitative measure of the deviations of the cross-section of a single fiber from round is known as the shape factor. The single fiber shape factor is a dimensionless ratio defined as:

$\text{Shape factor} = P/(4\pi A_F)^{1/2}$ wherein $A_F$=area of the fiber's cross-section and P=the perimeter of the cross-section of the fiber.

The shape factor for the single fibers of the present invention is equal to or greater than 2.0, preferably greater than about 5.0. The shape factor can be measured by hand from photomicrographs of cross-sections or it can be determined automatically by several commercially available computer controlled optical microscope systems. The shape factor of a round cross-section fiber is 1.

Another property of the shaped fiber is a measure of the ratio of void areas formed by the cross-section of a shaped fiber to the polymer area of the cross-section of the shaped fiber. This property is referred to herein as the Single Fiber Bulk Factor (SFBF), which is equal to or greater than 4 and preferably from 4 to 10. SFBF is defined as:

$$SFBF = \frac{\text{Sum of the void cross-sectional areas}}{\text{Fiber Cross-sectional Area}}$$

Figure 26A:
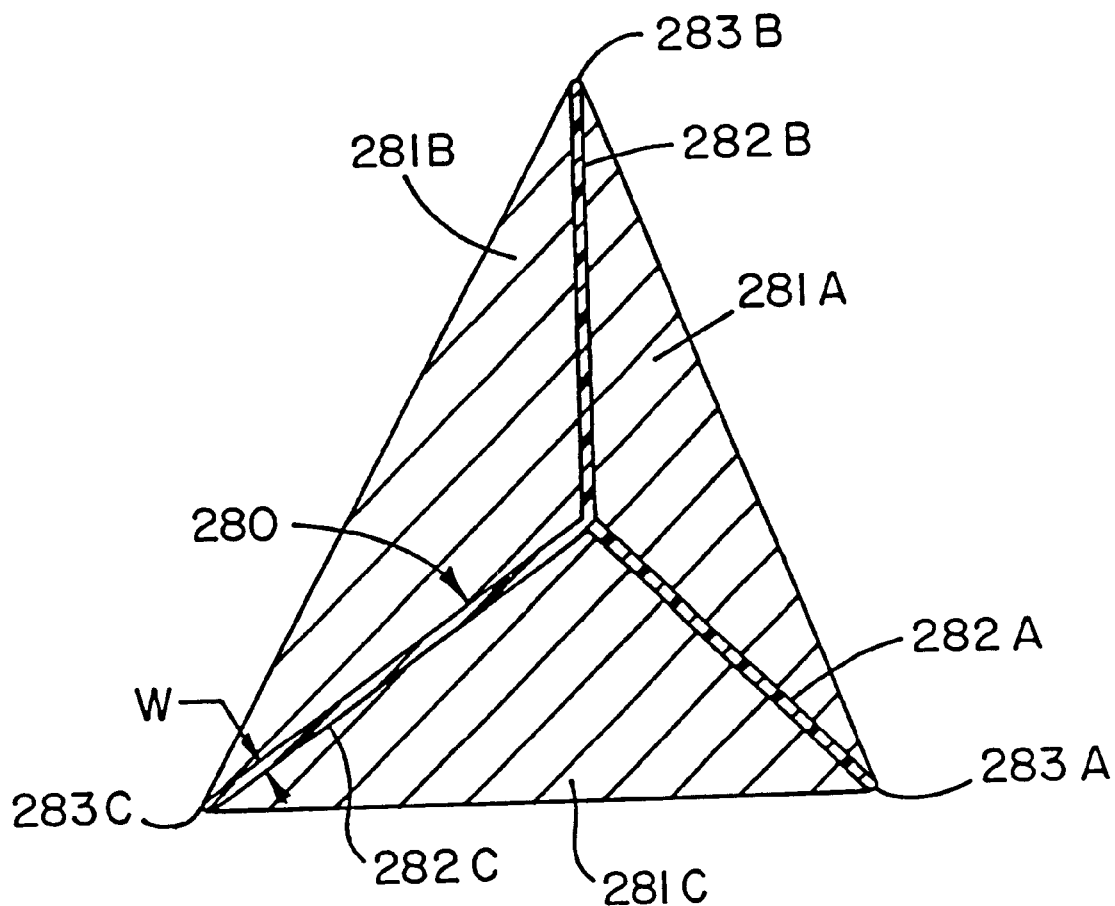
FIG. 26A is a schematic of a cross-section of a fiber for use in illustrating the definition of the single fiber bulk factor.
Figure 26B:
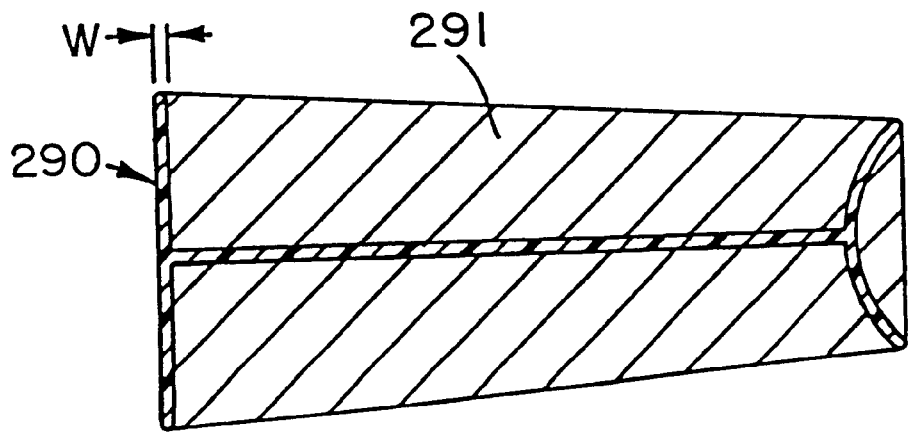
FIG. 26B is a schematic of a cross-section of a fiber for use in illustrating the definition of the single fiber bulk factor.

The void areas are illustrated in the fiber cross-sections of FIGS. 26A–B and 38A–B along with exemplary calculations of the SFBF for the cross-sections shown in FIGS. 26A–B. As with shape factor, the single fiber bulk factor can be determined by hand or using an automated measurement system.

Additional properties of the single fibers of a bundle of the invention that characterize the fibers' poor liquid transport properties include a $MPF_{SF}$ equal to or less than 0.03 cc/(den*hr) and a $VR_{SF}$ equal to or less than 4.0 cm. Calculations of these properties are discussed above.

Being poor liquid transporters, the single fibers of the invention preferably do not have intra-fiber capillaries. As used herein, intra-fiber capillaries means channel widths of less than 300 microns. The fibers' structures are such that a bundle of the fibers forms inter-fiber capillaries which create the large liquid fluxes. For example, single fibers of the bundles of the invention have an $MPF_{SF}$ less than about 0.03 cc/(den*hr) and a $VR_{SF}$ of less than about 4 centimeters in fifteen minutes. When these fibers define bundles of the invention, the bundles can have an $MPF_B$ of greater than 0.2 cc/(den*hr) and vertical rise of liquid of over six centimeters (after 15 minutes).

Prior art fibers having intra-fiber capillaries that effectively transport liquid on their surface meet the criteria set forth in U.S. Pat. No. 5,200,248 (the '248 patent). The fibers of the '248 patent, which individually act as excellent liquid transporters, have the following properties: Specific Capillary Volume (SCV) of at least 2.0 cc/gm, Specific Capillary Surface Area (SCSA) of at least 2000 cm²/gm, Compressive Strength Dry of at least 13,800 dynes/cm², Slenderness Ratio of at least about 9, and at least 30 percent of the capillary channels (i.e. intra-fiber capillaries) have a Capillary Channel Width (CCW) of less than about 300 microns. Fibers that have no intra-fiber capillaries are individually poor liquid transporters and are outside the scope of the '248 patent.

However, the fibers of the present invention that do not have intra-fiber capillaries and are individually poor liquid transporters, are unexpectedly excellent transporters of liquid if in the form of a bundle of such fibers comprising at least two individual fibers. Thus, the individual fibers of the present invention which do not have intra-fiber capillaries may be characterized as non-capillary channel structures and have the following properties: (1) either Specific Capillary (channel) Volume less than 2.0 cc/gm or Specific Capillary (channel) Surface Area less than 2000 cm²/gm and (2) more than 70% of intra-fiber capillaries (channels) having a channel width greater than 300 microns.

The following procedures are useful for determination of parameters used to define and evaluate the capillary channel structures, and are taken verbatim from U.S. Pat. No. 5,200,248 at column 27 line 45 to column 30 line 12 and column 35 line 63 to column 35 line 59.

The procedures may require preparation of structures of varying lengths, some of which may exceed the length of the structure actually intended for use. It is to be understood that any structures shorter than lengths required by the procedures are evaluated on the basis of equivalent structures having the requisite lengths set forth in such procedures, except as may be otherwise specifically provided. Specific units may be suggested in connection with measurement and/or calculation of parameters described in the procedures. These units are provided for exemplary purposes only. Other units consistent with the intent and purpose of the procedures can be used.

The procedure used to determine Specific Capillary Surface Area (SCSA) and Specific Capillary Volume (SCV) of a capillary channel structure is applied to a photomicrograph which shows a representative cross-section of the capillary channel structure. The cross-section of the structure is prepared for photomicrographing by embedding and microtoming techniques known to those skilled in the art. The following equations are used:

$$SCSA = \text{sum over } x=1 \text{ to } i, \text{ of } P_x/\rho A_s, \tag{1}$$

$$SCV = \text{sum over } x=1 \text{ to } i, \text{ of } Av_x/\rho A_s, \tag{2}$$

wherein:

ρ = density of the solid (i.e., polymer);

$A_S$ = area of the cross-section of capillary channel solid perpendicular to the capillary channel axis which bounds those capillary channels within the scope of criterial (a) and (b), the sum over x=1 to i of $P_x$=the sum of the perimeters of the cross section of the solid forming each of the capillary channels, x, wherein each perimeter $P_x$ bounds the capillary channel and is within the theoretical closure provided by $C_x$;

the sum over x=1 to i of $Av_x$=the sum of the void areas of the capillary channel structure wherein each $Av_x$ is calculated as the area bounded by the perimeter of the solid forming the channel and by $C_x$; and wherein i is the number of capillary channels in the structure, x refers to specific capillary channels of a capillary channel structure, and $C_x$ corresponds to that part of a circle which is convex toward the interior of the channel and which is of a selected diameter that closes each capillary channel, x, wherein the circle, $C_x$ is sized and positioned according to the following criteria:

(a) the circle, $C_x$, is tangent to both walls of the capillary channel, x, at the points where it meets the walls; and (b) for each capillary channel, x, the circle $C_x$ meeting (a) maximizes $Av_x$ for each such channel, x, subject to the limitations that:

(i) the lines tangential to the intersection of $C_x$ and the capillary channel walls intersect to form an angle of 120° or less; and (ii) $C_x$ can have a radius of no greater than about 0.025 cm with respect to the actual scale of the capillary channel structure (circle radius will be enlarged by the same magnification factor applied to the actual structure in the photomicrograph).

For capillary channel structures having capillary channel wall fluid exchange orifices, the effect on SCV and SCSA will generally not be of numerical significance due to the thin walls of the capillary channel structures hereof, and can generally be disregarded in the calculations.

For capillary channels having multiple points of tangency with a circle of maximum radius, as provided above, the circle is positioned so as to maximize cross-sectional area (Av) of the channel. For capillary channel structures having variation in cross-sectional size or shape, sufficient cross-sections can be evaluated to provide a representative weighted average SCV and/or SCSA. If, however, any portion of the structure of linear length (in the axial direction of the capillary channels) of at least about 0.2 cm, preferably at least about 1.0 cm, has a SCV and SCSA within the claimed ranges hereof, that such structure is said to comprise a capillary channel structure of the present invention.

For capillary channel sheets, particularly those with capillary channel bases of relatively large width, a representative sample of the product having a fraction of the total width of the base can be substituted in place of the entire cross-section of the sheet. Such fractional sample of the sheet preferably has a width of at least about 0.5 cm. The purpose of SCV and SCSA, as defined above, is to provide quantitative analysis of structures characterized by open capillary channels. It is conceivable that such structures can have solid portions, appendages, and the like, which do not otherwise contribute to the definition of the capillary channels in this procedure. The above criteria will exclude perimeter and void areas corresponding to such nonfunctional portions of the structure from the calculations. Also, the cross-sectional area of nonfunctional solid elements is not to be included in the calculation of $A_s$. Exclusion of such perimeters and cross-sectional area is exemplified in more detail below.

Figure 61:
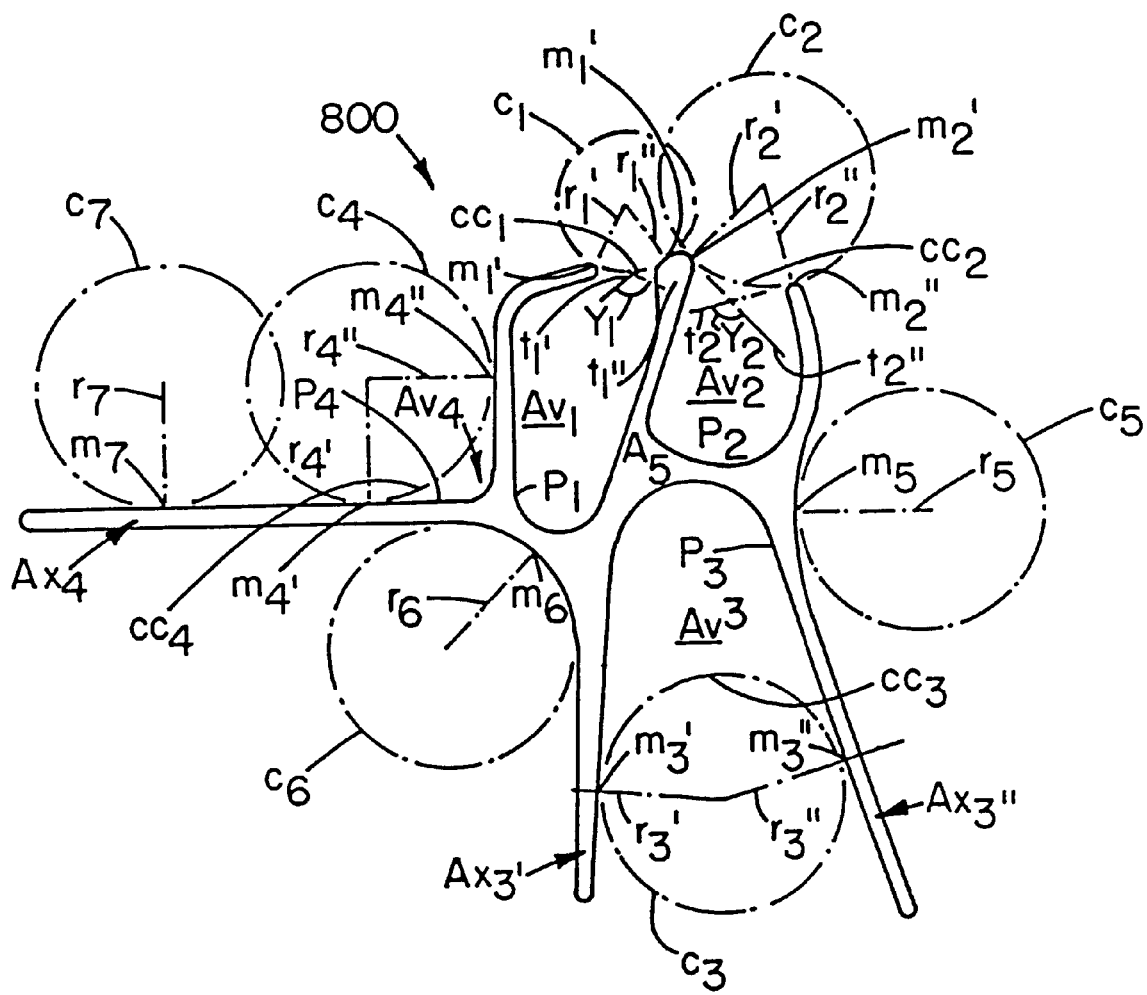
FIG. 61 is a schematic cross-section of a fiber helpful in defining SCV and SCSA.

FIG. 61 exemplifies a capillary channel structure fragment 800 and application of the SCV and SCSA procedure thereto. Shown is the fragment 800 of solid (i.e., polymer) having area $A_s$, capillary channel void areas $Av_1$, $Av_2$, $Av_3$, $Av_4$, with corresponding capillary channel perimeters $P_1$, $P_2$, $P_3$, $P_4$ and theoretical closure circles $C_1$, $C_2$, $C_3$, and $C_4$. Also shown are circles $C_5$, $C_6$, $C_7$. Radii $r_{1'}$, $r_{1''}$, $r_{2'}$, $r_{2''}$, $r_{3'}$, $r_{3''}$, $r_{4'}$, $r_{4''}$, $r_5$, $r_6$, $r_7$ are each perpendicular to the line tangent to the points of intersection $m_{1'}$, $m_{1''}$, $m_{2'}$, $m_{2''}$, $m_{3'}$, $M_{3''}$, $m_{4'}$, $m_{4''}$, $m_5$, $m_6$, $m_7$, respectively, between the corresponding circles, $C_1$, $C_2$, $C_3$, $C_4$, $C_5$, $C_6$, $C_7$ and the solid material of fragment 800.

The circles $C_1$, $C_2$, $C_3$, and $C_4$ are drawn so as to meet the above criteria. As can be seen circles $C_1$ and $C_2$ are limited in radius $r_1$, $r_2$ by angles $\gamma_1$, $\gamma_2$ which represent 120° angles of intersection between tangent lines $t_{1'}$, $t_{1''}$, and between $t_{2'}$, $t_{2''}$, respectively. $Av_1$, $Av_2$, $Av_3$, and $Av_4$ are the areas bounded by perimeters $P_1$, $P_2$, $P_3$, and $P_4$ and curves $cc_1$, $cc_2$, $cc_3$, and $cc_4$, respectively. Circles $C_3$ and $C_4$ represent the maximum size circle for capillary channel, wherein the angle of intersection of lines drawn tangent to the circle at points $m_{3'}$, $m_{3''}$ and at $m_{4'}$, and $m_{4''}$, respectively, would be less than 120°. Thus, as represented in this exemplary figure, circles $C_3$ and $C_4$ would each have radius of 0.025 cm, after reduction for magnification effects. Perimeters are determined as the length of the solid boundary interior to the channels between the points of intersection between the circle and the solid for each channel. $C_5$, $C_6$, and $C_7$ represent circles of maximum radius applied to portions of the structure which do not qualify as capillary channels according to the criteria of this procedure. Hence, P and Av for these circles would be zero. As perimeters $P_1$, $P_2$, $P_3$, and $P_4$, and curves $cc_1$, $cc_2$, $cc_3$, and $cc_4$, can be seen, the area of the solid between $m_{4'}$, and $m_{4''}$, would be included within $A_s$ since such solid corresponds to capillary channel walls bounding channels within the criteria for Av in the calculation of SCV and SCSA. Areas $A_{x3'}$ and $A_{x3''}$, which are bounded by linear extensions of the radii $r_{3'}$, $r_{3''}$, (said radii being perpendicular to the line of tangency between the circle $C_3$ and the walls of the channel), are not included in $A_s$. Likewise, radius $r_4$, truncates area $A_{x4}$ from the calculation $A_s$ based upon extension of $r_4$, of circle $C_4$.

Figure 62:
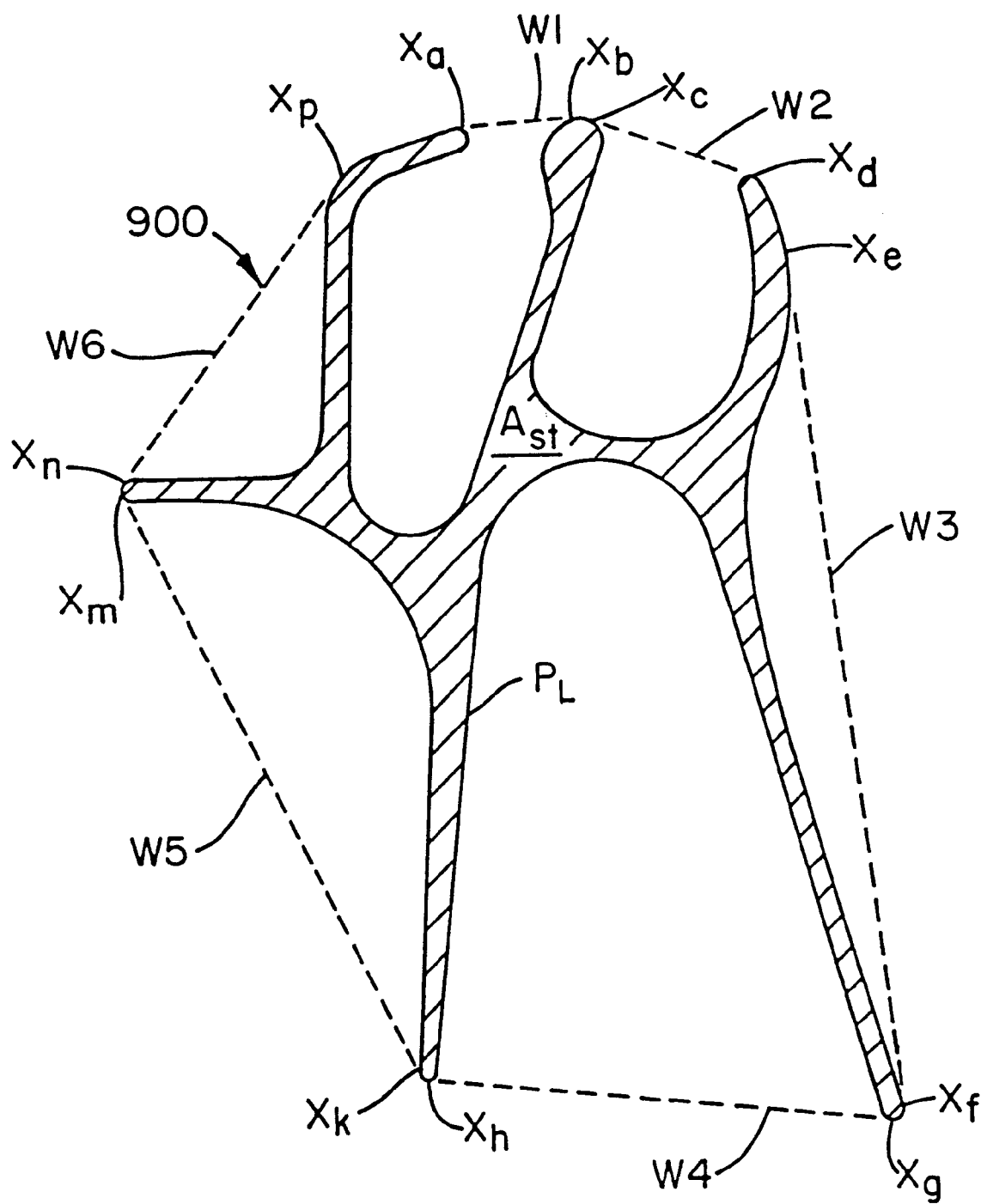
FIG. 62 is a schematic cross-section of a fiber helpful in defining S and CCW.

Slenderness Ratio (S), Capillary Channel Width (CCW), and Average Structure Thickness ($t_{ave}$) are determined according to the procedures as follow. The procedures are implemented based upon a photomicrograph of a representative microtomed cross-section of the capillary channel structure, as previously described. For capillary channel structures having variation in Slenderness Ratio, Capillary Channel Width, and Average Structure Thickness in the axial direction of the capillary channels, sufficient cross-sections should be evaluated to provide a representative weighted average Slenderness Ratio, Capillary Channel Width, and/or average structure thickness value. If, however, any portion of this structure of linear length in the axial direction of the capillary channels of at least about 0.2 cm, preferably at least about 1.0 cm, has a Slenderness Ratio, capillary channel width, and/or average structure thickness value within the ranges hereof, then such structure may comprise a capillary channel structure of the-present invention. Reference is made to FIG. 62 for exemplary purposes of the procedures.

The following equations are used:

$$S = L^2/4A_{st}$$

$$t_{ave} = 2A_{st}/L$$

wherein:

L=total solid perimeter of the cross-section of the structure; and $A_{st}$=total area of the cross-section of the solid forming the structure perpendicular to the capillary channel axis.

The foregoing equation for Slenderness Ratio treats the fiber under consideration as if it has one channel-forming wall therein. For channeled fibers having a functional portion wherein one or more channels are present, the formula for Slenderness Ratio (S) can be given as:

$$S = L^2/4A_{st}N$$

wherein:

L and $A_{st}$ are as hereinbefore defined; and

N=number of channel walls in the structure, said walls being those that have, on one or both sides, channels that are closable by straight closure chords.

CCW is the length of the straight closure chord of a capillary channel wherein said chord closes said intra-structure capillary channel and which tangentially contacts the points of intersection with the capillary channel walls of said channel in such a way to maximize the volume of the channel. (Portions of the structure which do not contribute open channels closable by straight closure chords should be disregarded prior to the above calculations.)

FIG. 62 shows, for exemplary purposes, a cross-section of a capillary channel structure 900 having chords W1, W2, W3, W4, W5, and W6 for capillary channels C1, C2, C3, C4, C5, and C6, respectively, thus N=6. FIG. 62 also indicates the region corresponding to total cross-sectional area $A_{st}$ and indicates continuous line $P_L$, the length of which is the total perimeter L. $X_a$–$X_p$ indicate points of tangency of the chords and the cross-section.

Figure 10:
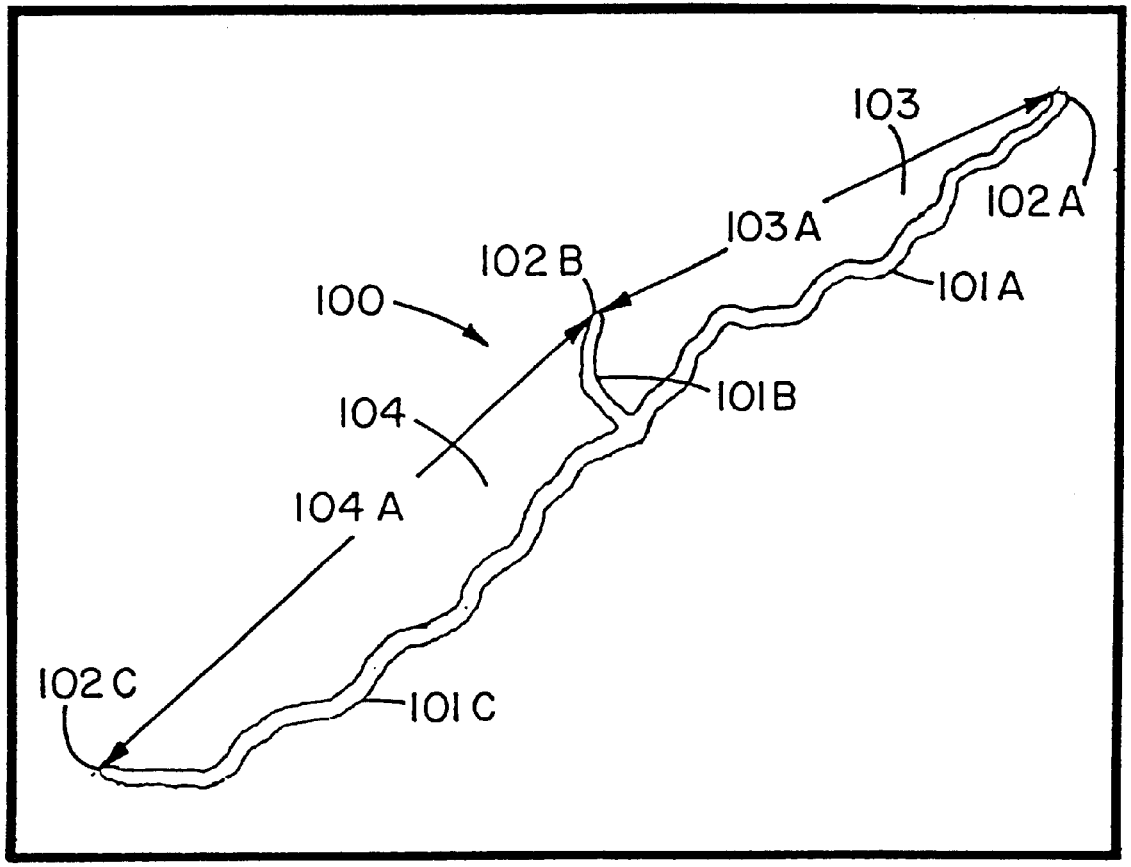
FIG. 10 is a photocopy of a photograph at a magnification of 163 of a cross-section of a fiber of example 5.

Referring now to FIG. 10, a cross-section of an exemplary fiber of a bundle of the present invention is shown which approximates the idealized structure discussed above. This cross-section includes the long thin channel arms 101A and 101C and short thin channel arm 101B. When a plurality of fibers having the cross-section shown in FIG. 10 are bundled together the long thin channel arms 101A and 101C of adjacent fibers oppose one another and are spaced from one another by the standoff arms 101B at a distance between 50 and 100 microns (i.e., the inter-fiber average capillary width). Thus, the standoff arms 101B space the long thin arms 101A and 101C of adjacent fibers from one another, and the long thin arms 101A and 101C of adjacent fibers that oppose one another approximate the idealized parallel inter-fiber capillary channel walls discussed above. The fact that the long thin arms 101A and 101C are much longer than the inter-fiber average capillary width, D, defines a capillary channel having a length (i.e., parallel to the long arms) that is greater than D. The cross-sections of the fibers having a section (such as an arm or base) extending in one dimension at least the desired inter-fiber average capillary width indicated above is an important characteristic of the present invention.

Synthetic fibers of the invention are fibers made from the major melt spinnable groups. These groups include polyesters, nylons, polyolefins, and cellulose esters. Fibers from poly(ethylene terephthalate) and polypropylene are especially useful at least because of their manufacturability and wide range of applications. Preferably, the denier of each fiber is between about 15 and about 250, and more preferably between about 30 and 170.

Fiber Surface Composition

The fibers of the bundles of the invention have a surface composition that is either hydrophilic or hydrophobic. The surface composition may be inherent due the nature of the material used to make the fibers or may be fabricated by application of surface finishes. The type of surface finish depends on the nature of the liquid to be transported by the inter-fiber capillary channels. Hydrophilic surface finishes provide structures the surfaces of which have large adhesion tension (i.e., that strongly attract) with aqueous liquids and are therefore preferred for applications involving aqueous liquids. For absorption, filtering, and transport applications involving non-polar liquids a hydrophobic surface finish is required to provide large adhesion tensions with non-polar liquids.

Preferably, the fibers of the bundle have a hydrophilic surface which is defined as a surface having an adhesion tension with distilled water greater than 25 dynes/cm.

Preferably, the fibers of the bundle have a specific surface force which is mathematically determined by the following equation:

$$(P\gamma \cos(\theta a))/d \geq 0.03 \text{ dynes/den}$$

wherein P is the perimeter of the cross-section of the fiber; $\gamma$ is the surface tension of the liquid on the surface; $\theta$ is the advancing contact angle of the liquid on a flat surface having the same composition and finish as the surface of the fiber (as specified in U.S. Pat. No. 5,611,981); $\gamma \cos(\theta a)$ is the adhesion tension of the liquid on the surface of the fiber; and d is the denier of the fiber on which the P was measured. Bundles of fibers which satisfy this inequality have excellent flow of fluid, whether aqueous or nonaqueous, along the length of the bundle.

The surface finishes are typically coated on fibers during their manufacture. The coating usually occurs just after the molten polymer is extruded through the aperture of a spinnerette and quenched, but it can be applied later. The thickness of the coating is much thinner than the cross-section of the fiber and is measured in terms of its percent of the total weight of the fiber. The weight percent of the coating is typically between 0.005 and 2.0 percent of the total weight of the fiber.

Some of the finishes/lubricants useful to provide large adhesion tensions to aqueous liquids are described or referenced in U.S. Pat. No. 5,611,981. Surface finishes are well known in the art.

Large Liquid Flux

The forces creating the transport of a large flux of liquid along the bundle of the fibers are the result of the surface energetics and the thin armed cross-section shapes of the fibers and relative positions of the fibers when wetted, thereby forming the inter-fiber capillaries. When wetted, the bundle of fibers has a large ratio of inter-fiber capillary volume (i.e., void volume) to the volume of the polymer in the fibers forming the bundle. The thinner the cross-sections of the fibers, the larger the ratio of the void volume to the volume of the polymer in the fibers for a given cross-sectional shape. This ratio may be characterized by the Single Fiber Bulk Factor or specific volume.

The surface tension of the liquid generates radially directed forces on the fibers of the bundle that press or collapse the fibers of the bundle against one another until the fibers are constrained from further radial collapse by their cross-sectional shapes. The initial collapse occurs very quickly once the fibers are wetted and results in the fibers of the bundle being in contact with one another along their lengths shortly after the bundle is wetted. Thus, as long as the fibers are in contact at any point along their lengths at the time the fibers are wetted, the forces on any two fibers are sufficient to press the fibers against one another to form the inter-fiber capillaries.

The flux of a liquid in any capillary is the product of the cross-sectional area of the capillary available for flow times the velocity of the liquid in the cross-sectional area of the capillary that is available for flow per mass associated with the channel. For the bundles of fibers to be effective liquid movers, the velocity of the liquid/solid/air front moving from where the bundle is wetted along the axis of the bundle times the cross-sectional area for flow must be relatively large. The Initial Velocity of liquid along a bundle of fibers of the invention synergistically increases with the number of fibers from two fibers per bundle to about twelve fibers per bundle after which there is little change in initial velocity with numbers of fibers in the bundle.

The flux of a liquid in any capillary is also dependent on the interplay of the driving force on the liquid in the capillary, the viscous drag force on the moving liquid, and the gravitational forces on the liquid. The liquid flux is proportional to the driving force divided by viscous drag force (also known as resistance to flow). The gravitational forces on the liquid affect the liquid flux for capillaries that are not aligned horizontally as is often the case for absorbent product worn by humans.

The driving force on the liquid in any capillary is proportional to the adhesion tension of the liquid with the surface of the capillary and to the perimeter of the cross-section of the capillary. Thus, larger adhesion tensions result in larger liquid fluxes. The adhesion tension of the liquid with the surface of the capillary depends upon the composition of the liquid and the composition of the surface of the capillary. Most conventional hydrophilic surface finishes provide an adhesion tension with aqueous liquids between about twenty and sixty dynes/centimeter. The adhesion tensions with non-polar liquids for most conventional hydrophobic surface finishes are in the range of ten to thirty dynes/centimeter.

The viscous drag force on the moving liquid in the capillary is approximately proportional to the viscosity of the moving liquid in the capillary, the perimeter of the cross-section of the capillary, and the diameter of the capillary. Capillaries that have narrow widths have a relatively large ratio of the perimeter of the cross-section of the capillary to the cross-sectional area of the capillary resulting in increased viscous drag force and, thus, reduced liquid flux.

The force of gravity on the liquid in the capillary will affect the liquid flux through the capillary if the capillary is not aligned horizontally. Because of the gravitational force, the width of a vertically aligned capillary that maximizes the liquid flux up to a given height is narrower than the width of a horizontally aligned capillary that maximizes the liquid flux.

The average inter-fiber capillary width, D, is the measurement utilized to determine if the inter-fiber capillaries are sufficiently spaced apart to result in large fluxes. D, as discussed above, is the average spacing between opposing walls of the inter-fiber capillaries and is between 25 and 400 microns. Bundles that have inter-fiber capillaries having large capillary cross-section perimeter length per cross-sectional area of the capillary and narrow average inter-fiber capillary widths (D), have high resistance to flow. Thus, when wetted, bundles with small Ds must have stronger driving forces per cross-sectional area of the inter-fiber capillaries in order to have large fluxes. Small inter-fiber capillary widths do not provide the maximum liquid flux because narrow capillaries have smaller cross-sections for liquid flow and the viscous drag force inhibits the speed of the moving liquid.

In view of all of the forces on aqueous liquids, the preferred D for a capillary formed from a polymer structure that is intended to maximize the liquid flux of aqueous liquids and that has an adhesion tension provided by a conventional surface coating is between 50 and 150 microns for a capillary in which the liquid must rise up at least three centimeters and is between 200 and 400 microns for a horizontally oriented capillary. While it is useful to move liquid up to a height of three centimeters in many absorbent products, obviously it is desirable to maximize the liquid flux up to other heights, as well. Thus, D is preferably between 40 and 120 microns for a polymer structure that is intended to provide a maximal flux up to about six centimeters.

Acquisition/Distribution Structures

Preferably, the bundles of the invention are incorporated into novel disposable absorbent products such as diapers, adult incontinent products, and feminine hygiene products, as a means to internally acquire and transport liquid in those products.

This invention also includes novel liquid acquisition/distribution structures for absorbent products that distribute aqueous liquids and are useful in consumer disposable products such as diapers, feminine napkins and incontinent products. The liquid acquisition/distribution structures acquire and distribute human body liquids, reduce leakage, improve core material utilization by increasing the liquid distribution to regions of the core, which improves dryness of the exterior of the absorbent product thereby increasing the wearer's comfort.

The acquisition/distribution structures may also be useful for non-polar liquids. For example, absorbent materials are useful for absorbent products for cleaning up household or industrial oil spills. Absorbent products for cleaning up oils may include an acquisition/distribution structure of this invention that is tailored for acquiring and distributing non-polar liquids.

Figure 40:
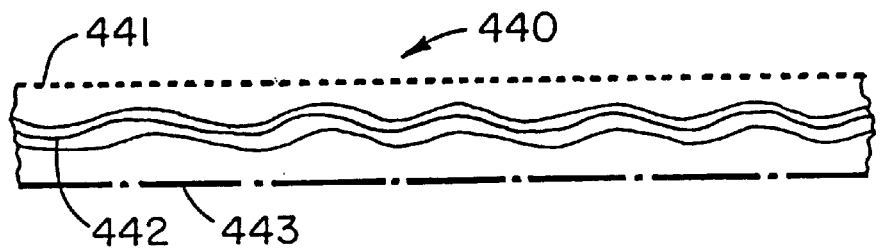
FIG. 40A is a schematic side sectional view of a basic liquid acquisition/distribution structure of the present invention.
FIG. 40B is a schematic side sectional view of an absorbent product of the invention showing the distribution of the liquid in the acquisition/distribution structure between the cover sheet and the absorbent core.
Figure 40:
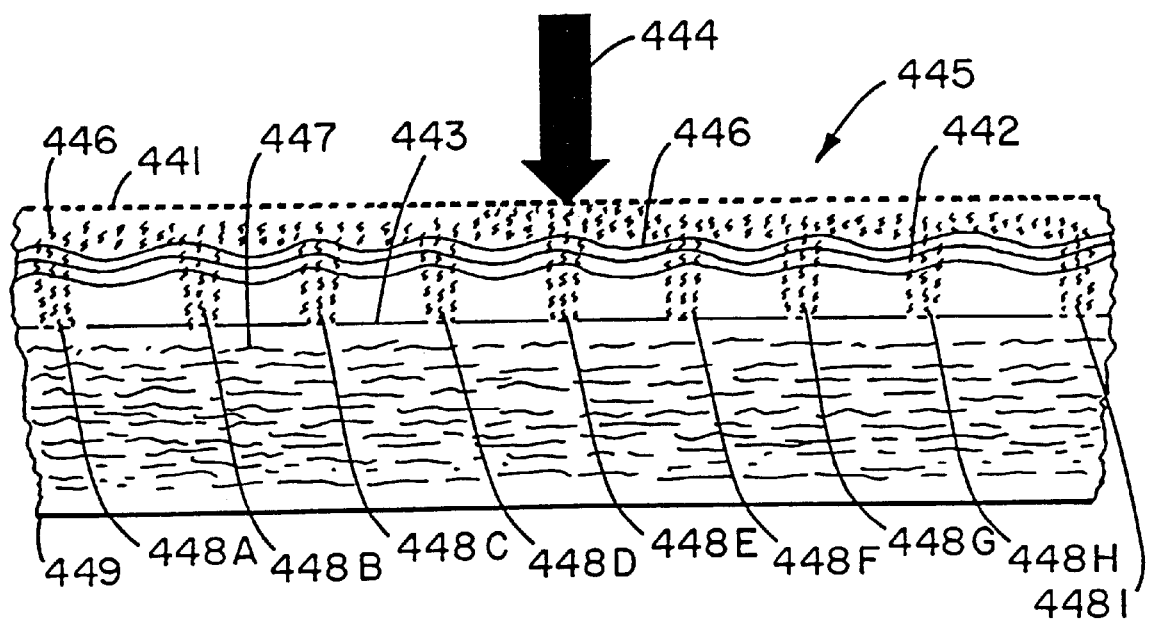
Figure 43:
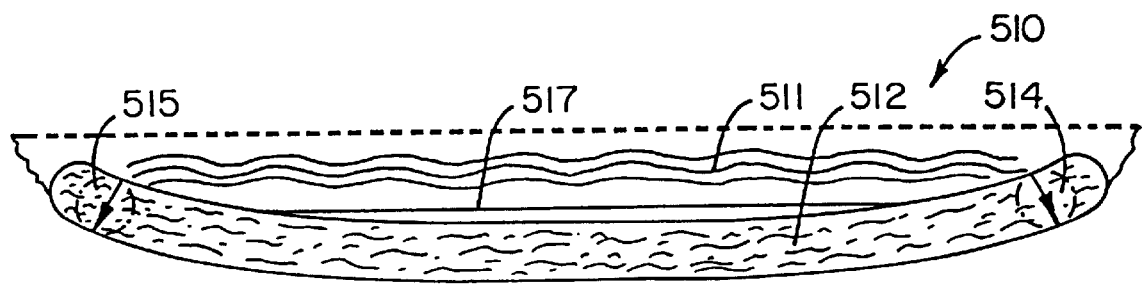
FIGS. 43A–B are side sectional views of the acquisition/distribution structure and absorbent core showing embodiments of the communication of the channels or grooves in the distribution layer with the absorbent core.
Figure 43:
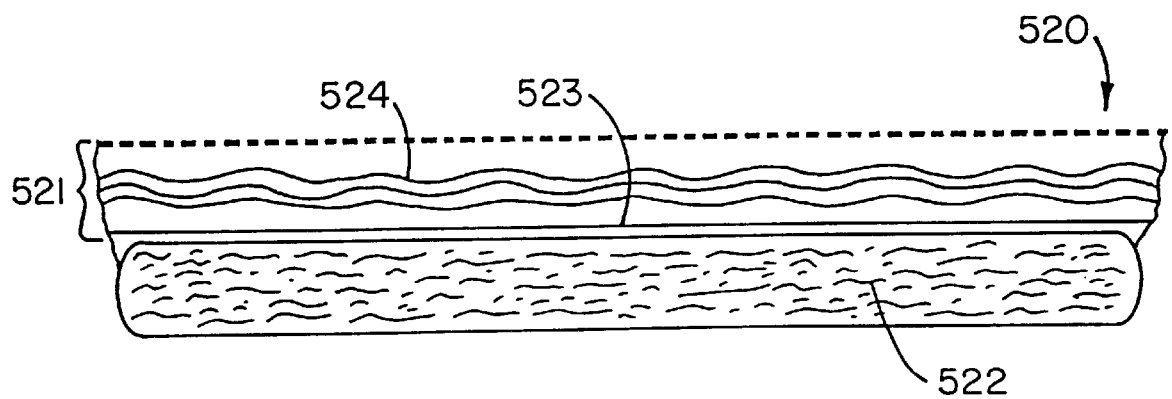
Figure 44:
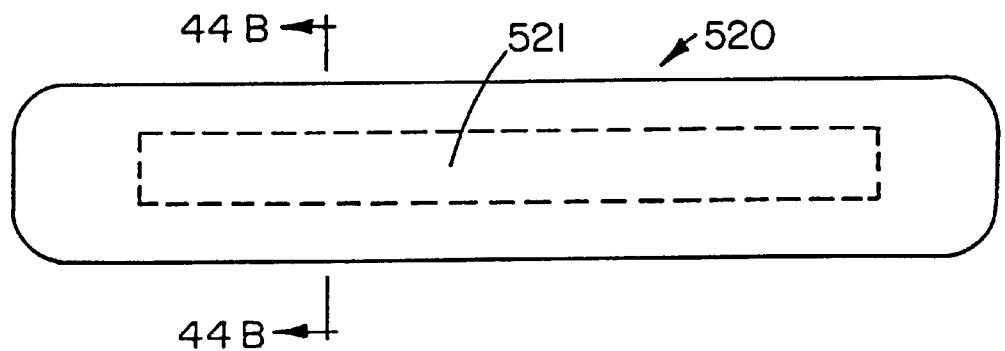
FIG. 44A is a top plan view of a liquid acquisition/distribution structure of the invention used in examples 15–22.
FIG. 44B is a side sectional view of the acquisition/distribution system of FIG. 44A.
Figure 44:
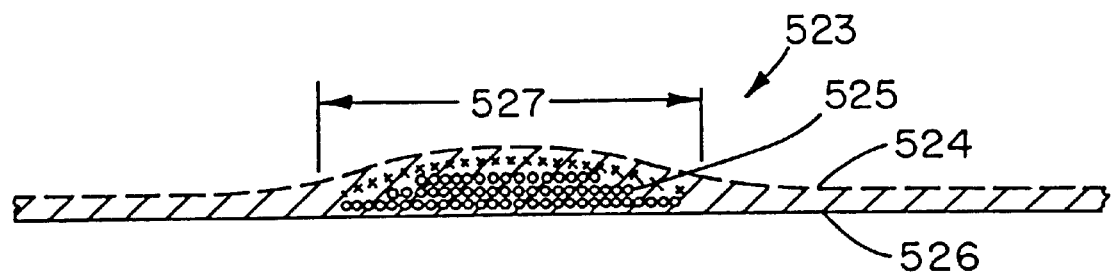

The novel absorbent product of the invention include (1) a liquid acquisition/distribution structure comprising (a) a top layer, (b) a distribution layer and (c) a flow resistance layer that is resistant to penetration in the direction perpendicular to the plane of the fabric, the basic structure of which is shown in FIG. 40A, (2) an absorbent core and (3) an impermeable back sheet. The liquid acquisition/distribution structure of the absorbent product of the invention is usually the layer (or layers) directly above the absorbent core containing the liquid storage material, as shown in FIG. 43B. The core is above the impermeable back sheet thus completing the absorbent product.

The top layer, also called a top sheet, may be any conventional top sheet material such as perforated polyethylene film or a calendar bonded or a spun bonded top sheet made from polypropylene fiber. However, the top layer may be made from other perforated polymer films and fibers. Preferably, the underside of the top sheet has a lower contact angle with aqueous liquids than the top side of the top sheet.

In another preferred embodiment the top sheet is made from an apertured film with cut out portions in the aperture walls to provide spontaneous liquid inversion from the frontside of the top sheet to the backside, as disclosed in U.S. patent application Ser. No. 545,450 filed Oct. 19, 1995.

The distribution layer or structure may be made from any continuous capillary system such as a capillary sheet, a web, a bundle, or a tow, or filaments that each provide spontaneous transport (or wetting) of liquids along their surfaces. The capillary system preferably includes capillaries aligned in specific directions. The capillary system may include fiber that each spontaneously transport (or wet) the liquids of interest. Preferably, the distribution layer or structure includes a bundle of the high $MPF_B$ fibers of the type disclosed in examples 1–9.

While not preferred, the distribution layer or structure may be made from a large number of round cross-section continuous fibers which are in close proximity to each other, preferably touching one another. Whichever fibers are used in the distribution layer, they define inter-fiber capillaries that provide for directional flow of liquid along the aligned direction of the fibers.

Examples of fibers are the spontaneously transporting or wettable fibers disclosed in U.S. Pat. Nos. 5,268,229, 5,200,248 and 5,611,981 and the bundles of fibers disclosed in this specification. These fibers may be made in the form of tows, slivers, nonwoven webs, yarns, etc.

The spontaneously transporting fibers are not constrained to be bundled together (i.e., in close proximity to each other) in order to transport liquids. However, the spontaneously transporting fibers provide more flux when they are bundled. Spontaneous wettability and close proximity in this context means that the fibers do not have to form inter-fiber capillaries, since each individual fiber will transport liquid but it is desirable. Since (1) capillary action is only significant for capillaries which can generate forces large when compared to the force of gravity on the liquid and (2) only capillaries with dimensions less than about 300 microns do so, close proximity in this context means less than about 300 microns. Therefore, spontaneous transporting or wettable fibers in the distribution layer can be more than 300 microns average spacing from one another.

The directional flow in the distribution layer can be designed by arrangements of the directions of transport of the liquid to be (1) essentially radially outward from a point or small region, (2) essentially bi-directional, (3) fan shaped (i.e., radiating along an arc from a point or small region), (4) multiple fan shaped (i.e., radiating along at least two arcs from a point or small region), (5) grid structured, and (6) any other essentially two dimensional flow pattern in the distribution layer, depending on the needs of the product. The important point is that the distribution layer can be designed so that liquid contacting a region on the distribution layer that is intended for the liquid's contact is distributed along a flow pattern by arrangement of the axes of the fiber forming the capillary system to locations in the structure remote from the contact region and where the liquid can be stored. This means that there is a first region in the distribution layer in which either the axes of the fibers are substantially aligned with one another or from which the axes of the fibers radiate away. In one preferred embodiment, there is a second region in the distribution layer where either the axes of the fibers are substantially aligned with one another along a different direction than the direction of the axes of the fibers in the first region or from which the axes of the fibers radiate away in an arc.

Preferably, the distribution layer provides a flow pattern distributing the liquid to at least two distinct regions, and more preferably at least three distinct regions, of absorbent core material.

Preferably, the distribution layer includes at least two sets, and more preferably at least three sets, of fibers that are aligned in the impingement region and that are not parallel to each other outside of the liquid impingement region. The distribution layer even more preferably includes a plurality of sets of fibers that are aligned in the impingement region, that are not parallel to each other outside of the impingement region and that distribute liquid from the impingement region substantially uniformly to more remote regions of the absorbent core.

Preferably, the distribution layer includes yarns produced from the spontaneously transporting or wettable fibers having a hydrophilic surface. The yarns (tows) in the distribution layer range up to 100,000 denier. The spacing of the yarns can vary from no spacing, that is all adjacent yarns are touching, to spacings up to three times the yarn diameter. The dpf's of the individual fibers may vary from 5 to 150. Preferably, the $MPF_B$ of the fibers in the distribution layer exceeds 0.005 cc/(den*hr).

The choice of the yarn for the distribution layer is influenced by the desired separation distance between the top sheet and the flow resistance layer. Typically 3.0 millimeter separation is the maximum uniform spacing distance. However, in some cases it is desirable to have essentially all of the fibers forming a single bundle. In this case the separation distance between the top sheet and the flow resistance layer is essentially zero at some edge of the article but may be up to 10 millimeters where the fiber bundle is between the top sheet and the flow resistance layer.

In a preferred embodiment all of the fibers in the distribution layer are located within an approximately one inch wide band along a major axis centerline of the absorbent article.

The weight of the distribution layer depends on the type of product. For feminine napkins, the weight should be between ¼ and 2 grams with the length of the fibers being between 7 and 25 centimeters. For diapers, the weight of the distribution layer may be between ½ and 4 grams with the length of the fibers being between 10 and 40 centimeters. For adult incontinent products, the weight of the distribution layer should be between 1 and 10 grams with the lengths of the fibers being between 10 and 70 centimeters.

The distribution layer may include fibers of at least two lengths. This enables transport of the liquid to regions at different lengths from the impingement region. The specific lengths of fibers in the distribution layer and the distribution of those lengths depends on the design of the absorbent article.

The flow resistance layer provides two primary functions. First, the flow resistance layer provides a resistance to flow that is perpendicular to the plane of the layer. This first function prevents the liquid from reaching the core until after the liquid is distributed. Second, the flow resistance layer helps keep the directional capillaries in the distribution layer from contacting the core material where that contact is not desired. The flow resistance layer may have the same structure and composition as the top sheet. The flow resistance layer may also be designed to have more flow resistance than the top sheet. The length of the flow resistance layer may be shorter than the distribution layer or the top sheet layer. This will allow the distribution layer to transport liquid directly to predetermined regions of the absorbent core beyond the edges of the flow resistance layer. The flow resistance layer may also have a set of apertures through which the distribution layer may communicate liquid to the absorbent core. Preferably, the set of apertures are spaced in a designed array. For example, the apertures could be arrayed to provide a substantially uniform liquid flux to all regions of the absorbent core.

Preferred Embodiments of the Invention

Spinnerettes, Fibers and Bundles

Referring now in more detail to the drawings, in which like reference numerals indicate identical or corresponding parts throughout the several views, FIG. 1A is a schematic showing the dimensions of an aperture of a spinnerette used to make the fibers of example 1 including arms 1, 2, 3, which radiate from a common axis 4. The arms 1, 2, 3, have a short dimension having a width W and a long dimension having a length of 150 W. The width w is 0.067 millimeters (which is 2.6 mils) wide.

Figure 1C:
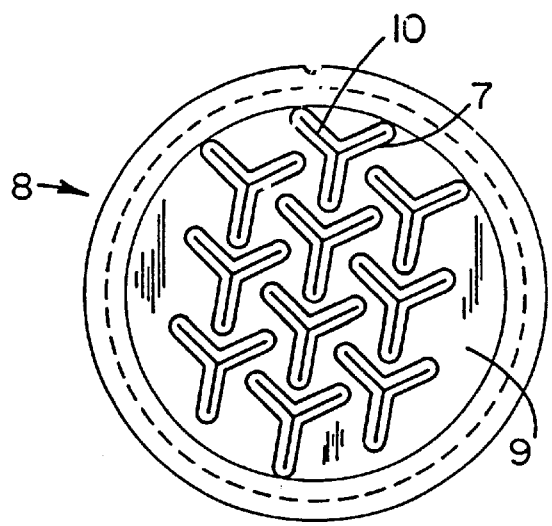
FIG. 1C is a plan view of an interior face of the spinnerette used in example 1 showing a bore and aperture pattern.
Figure 1B:
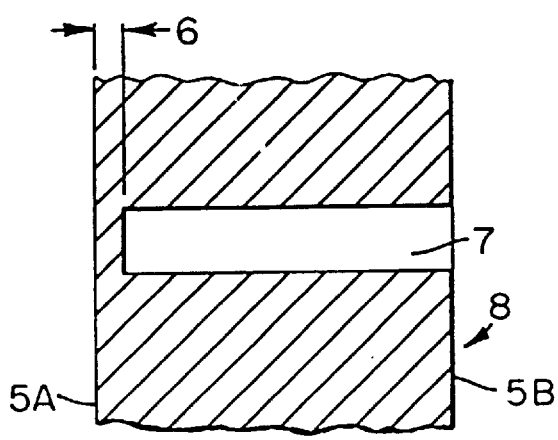
FIG. 1B is a partial sectional view showing a bore detail for the aperture of the spinnerette of FIG. 1A.

FIG. 1B shows the details of a bore for an aperture of the spinnerette used in example 1 including a first (external) face 5A, a second (internal) face 5B, a thickness 6, and a blank bore 7. The thickness 6 at the bottom of the blank bore 7 for the spinnerette used in example 1 is 50 mils (0.050 inches). The aperture is not shown in FIG. 1B. However, the spinnerette's apertures extend through the thickness 6 between the bottom of the blank bore 7 and the first face 5A.

FIG. 1C shows a spinnerette 8 having a face 9 and bores with apertures 10. There are 10 apertures in the spinnerette 8. The apertures are arranged along three rows and are all oriented the same way relative to the rows.

Figure 2:
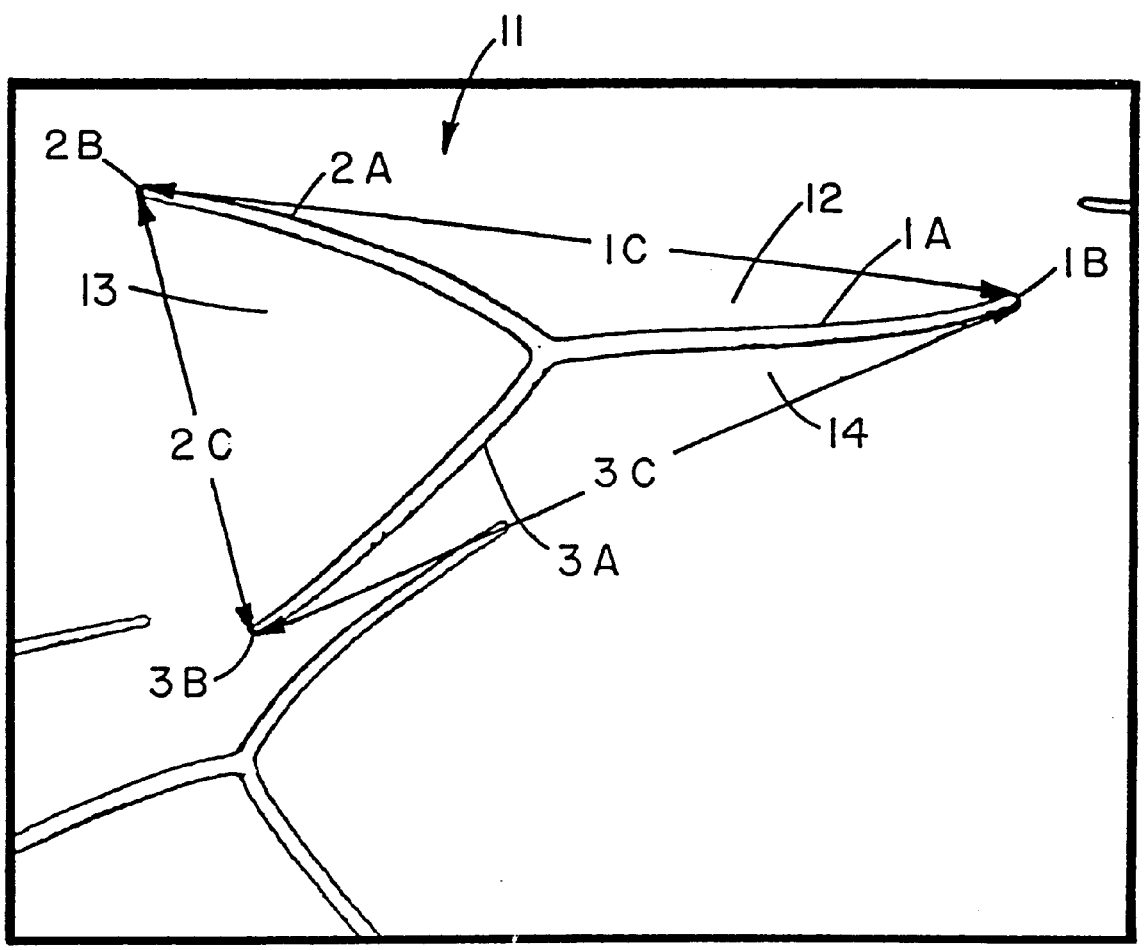
FIG. 2 is a photocopy of a photograph at a magnification of 156 of cross-sections of the fibers of example 1.

FIG. 2 shows a cross-section of a fiber of example 1 in a photograph taken at a magnification of 156. The fiber's cross-section 11 is formed from polymer arms 1A, 2A, 3A, upon extrusion of the fiber from the arms 1, 2, 3, of the aperture pattern shown in FIG. 1. The polymer arms 1A, 2A, 3A, define channels 12, 13, and 14. Polymer arms 1A, 2A, and 3A, have distal tips 1B, 2B, and 3B, respectively. The length of a line segment that is tangent to two adjacent distal tips of the cross-section 12, defines a channel width. For example, the distance between the distal tip 1B and 2B defines the channel width 1C for the channel 12. Similarly, channel widths 2C and 3C are the widths of the channels between the distal tips 2B and 3B, and 3B and 1B, respectively.

Figure 3A:
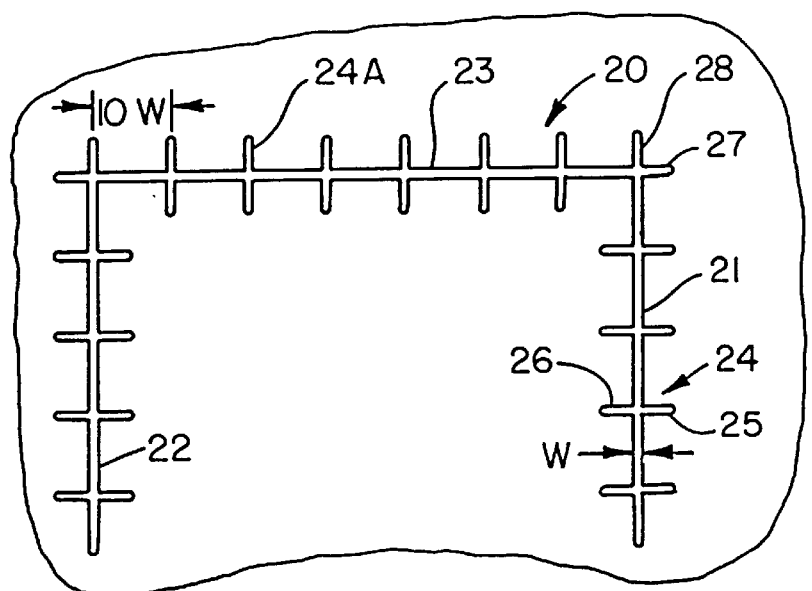
FIG. 3A is an engineering diagram in plan showing the relative dimensions of an aperture of a spinnerette used in example 2.

FIG. 3A shows the dimensions of an aperture 20 in which W illustrates a width of the aperture 20 and lengths of portions of the aperture are shown relative to the length W. The aperture 20 is formed from channel walls 21, 22 which extend perpendicular to a channel base 23, and protrusions 24 that extend away from the channel walls. The protrusions 24 include an outer portion 25 that protrudes away from the channel and an inner portion 26 that protrudes into the channel. In addition, aperture 20 includes protrusion 27 which is an extension of the base 23 beyond the intersection of the base 23 and the channel wall 21, and protrusion 28 that is an extension of the channel wall 21 beyond the intersection of the channel wall 21 and the channel base 23. Protrusions similar to protrusions 27 and 28 exist near the intersection of channel wall 22 and channel base 23. The protrusions 25, 26, 27, 28 are shown as being five times as long as the width W. However, those protrusions could be longer or shorter, depending upon the desired cross-section of the fiber produced therefrom. In addition, the protrusions 24 that are further from the intersection of the channel wall 21 and the base 23 may be longer than the protrusions closer to the intersection of the channel wall 21 and the channel base 23 in order to increase the surface area of the channel in the polymer fiber resulting from the extrusion of polymer through the aperture 20. Similarly, the protrusions 24A along the base 23 that are near the center of the base 23 may be longer than the protrusions 24 from the base 23 that are nearer the channel walls 21, 22, in order to increase the surface area of the channel of the polymer fiber resulting from extrusion of polymer through the aperture 20. The protrusions along the channel walls and base of the aperture 20 do not need to be evenly spaced, and the relative lengths of the walls in the base may vary from those shown in FIG. 3A. The width W is 0.090 millimeters for the aperture 20. The base 23 extends 70 W, and the arms 21, 22 extend about 47 W.

Figure 3C:
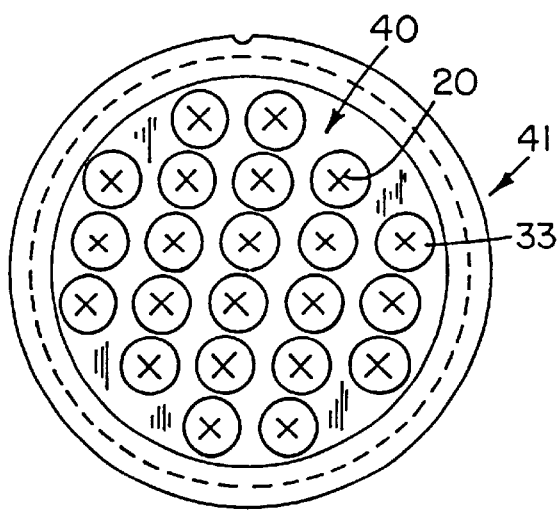
FIG. 3C is a plan view of an interior face of the spinnerette used in example 2 showing a spinnerette aperture pattern.
Figure 3B:
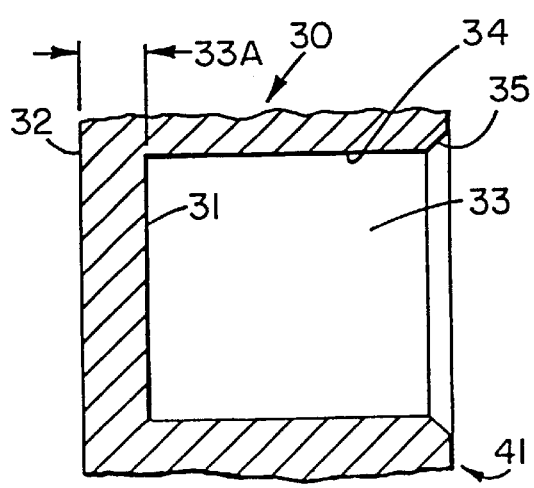
FIG. 3B is a partial sectional view showing a bore detail for the aperture of the spinnerette shown in FIG. 3A.

FIG. 3B shows a bore detail of a partial sectional view 30 for an aperture of a spinnerette used in example 2. The aperture is not shown in FIG. 3B. The partial sectional view 30 shows surface 31 and face 32 spaced from one another by a dimension 33A which is 0.092 plus or minus 0.02 inches in the spinnerette used in example 2. The aperture 20 of the spinnerette used in example 2 is machined through the blank dimension 33A. The corresponding blank dimension in the other examples range from about 0.040 inch to 0.100 inch. Surface 31 along with surface 34 partially define the bore 33. Bore 33 is also defined by a beveled surface 35. The diameter of the bore 33 of the spinnerette used in example 2 is about 0.36 inches. That is, the spacing between surfaces 34 and 35 shown in FIG. 3B is about 0.36 inches for the spinnerette used in example 2. Surface 35 is beveled at a 45° angle relative to surface 34.

FIG. 3C shows the spinnerette 41 used in example 2 having the bore and aperture pattern 40. The bore pattern consists of bores aligned in five rows in which the apertures are all oriented the same way.

Figure 4:
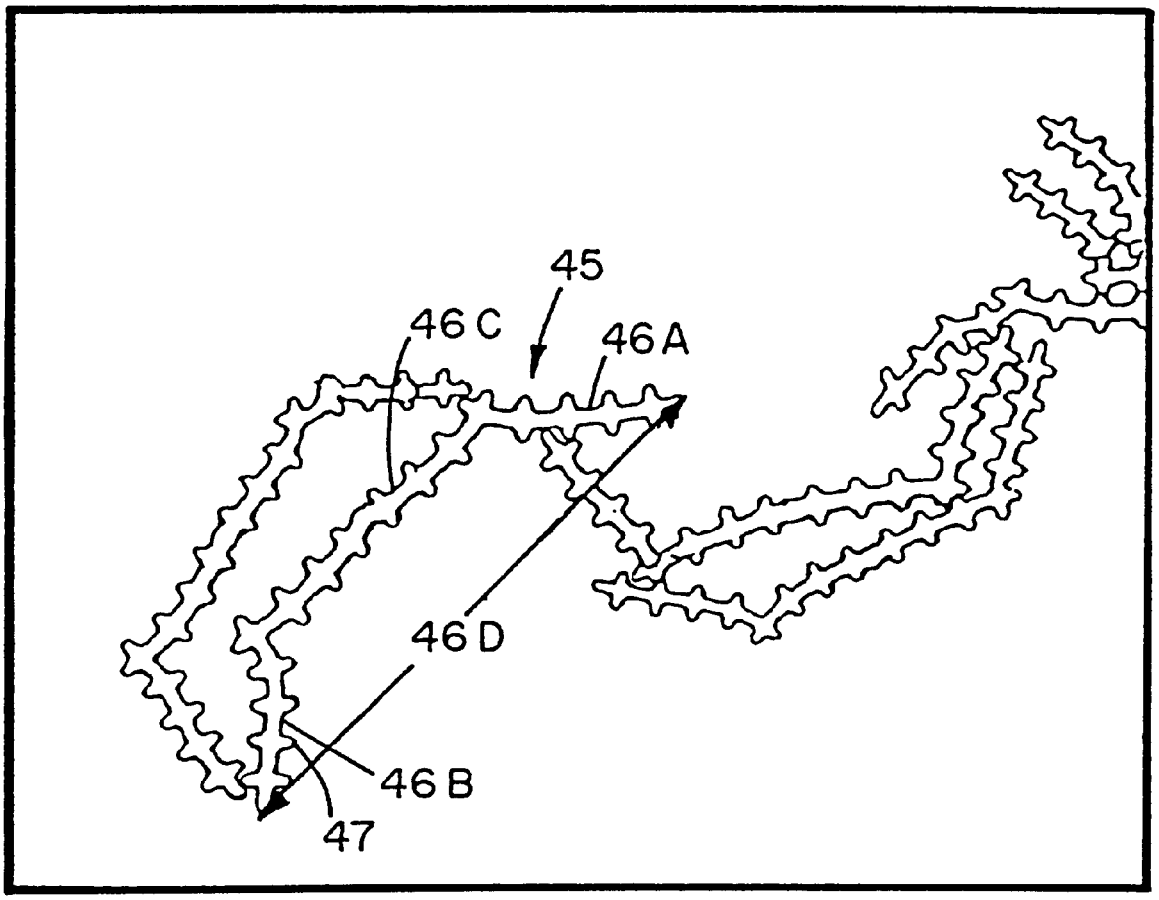
FIG. 4 is a photocopy of a photograph at a magnification of 162 of cross-sections of fibers of example 2.

FIG. 4 is a photocopy of a photograph taken at 162 magnification of fiber cross-sections including cross-section 45. Cross-section 45 includes polymer arms 46A, 46B, and polymer base 46C. The polymer arms 46A, 46B extend from the polymer base 46C such that the base and each arm forms an angle of substantially greater than 90°. The cross-section 45 includes protrusions 47 extending from the polymer arms 46A, 46B and the polymer base 46C that correspond to the protrusions 24, 27, 28 of the aperture 20 of the spinnerette shown in FIG. 3. The cross-section 45 has a channel width 46D.

The polymer arms 46A, 46B and the polymer base 46C form angles of intersection substantially greater than the 900 angles of intersection shown for the base 23 and the arms 21 and 22 of the aperture 20 of the spinnerette shown in FIG. 3A. The fiber's angles being greater than the aperture's angles is due to the effect of surface tension on the shaped molten polymer extruded from the shaped aperture. The protrusions 47 of the cross-section 45 of the polymer fiber have an aspect ratio (i.e., height to width ratio) substantially smaller than the aspect ratio of the protrusions 24, 27, 28 in the aperture 20 of the spinnerette shown in FIG. 3A also due to the effect of surface tension on molten polymer extruded through the aperture 20.

Figure 5A:
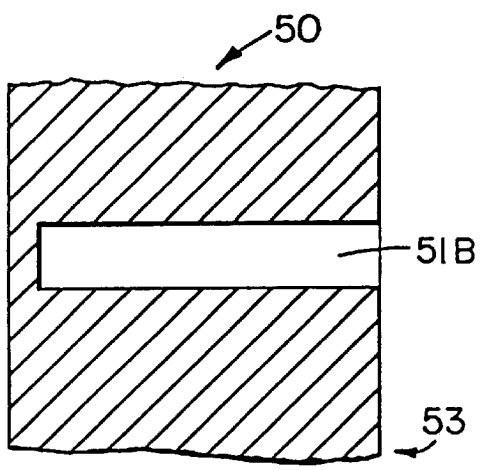
FIG. 5A is a partial sectional view of a bore for an aperture of a spinnerette used in example 3.
Figure 5B:
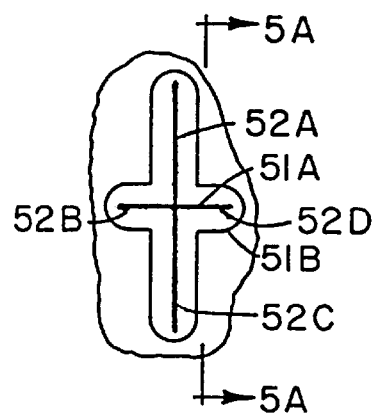
FIG. 5B is a schematic view of a bore and an aperture of a spinnerette used in example 3.

FIG. 5A shows a partial sectional view 50 of a bore detail for the bore and the aperture shown in FIG. 5B. The partial sectional view 50 is similar to the partial sectional view shown in FIG. 1B and does not show the aperture through the bottom of the bore.

FIG. 5B shows an aperture 51A in a bore 51B including long arms 52A and 52C and short arms 52B and 52D. The arms 52A, 52B, 52C and 52D extend away from a locating point defining 90° angles with one another.

Figure 5C:
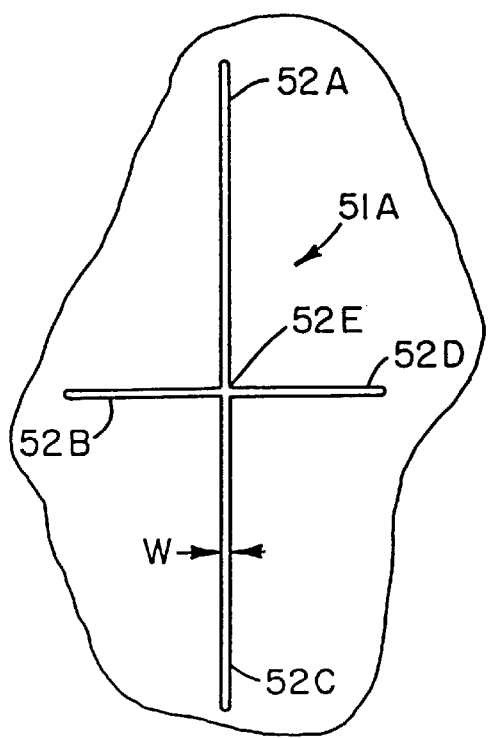
FIG. 5C is a schematic identifying relative dimensions of an aperture of a spinnerette used in example 3.

FIG. 5C is a schematic diagram identifying relative dimensions of the aperture 51A of example 3. The long arms 52A, 52C have a length of 150 W and the short arms 52B and 52D have a length of 75 W. 52A, 52B, 52C and 52D all radiate from a common axis 52E. W is the width of the aperture in each arm perpendicular to the direction in which that arm extends. The width W is 0.067 millimeters (which is 2.6 mils).

Figure 5D:
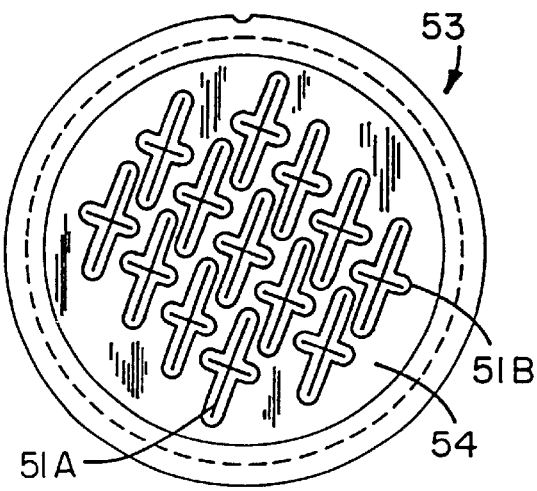
FIG. 5D is a plan view of an interior face of the spinnerette used in example 3 showing a bore and an aperture pattern.

FIG. 5D shows a spinnerette 53 having apertures 51A in the bores 51B for the spinnerette face 54 of example 3. There are thirteen apretures 51A aligned in three rows in the spinnerette 53.

Figure 6:
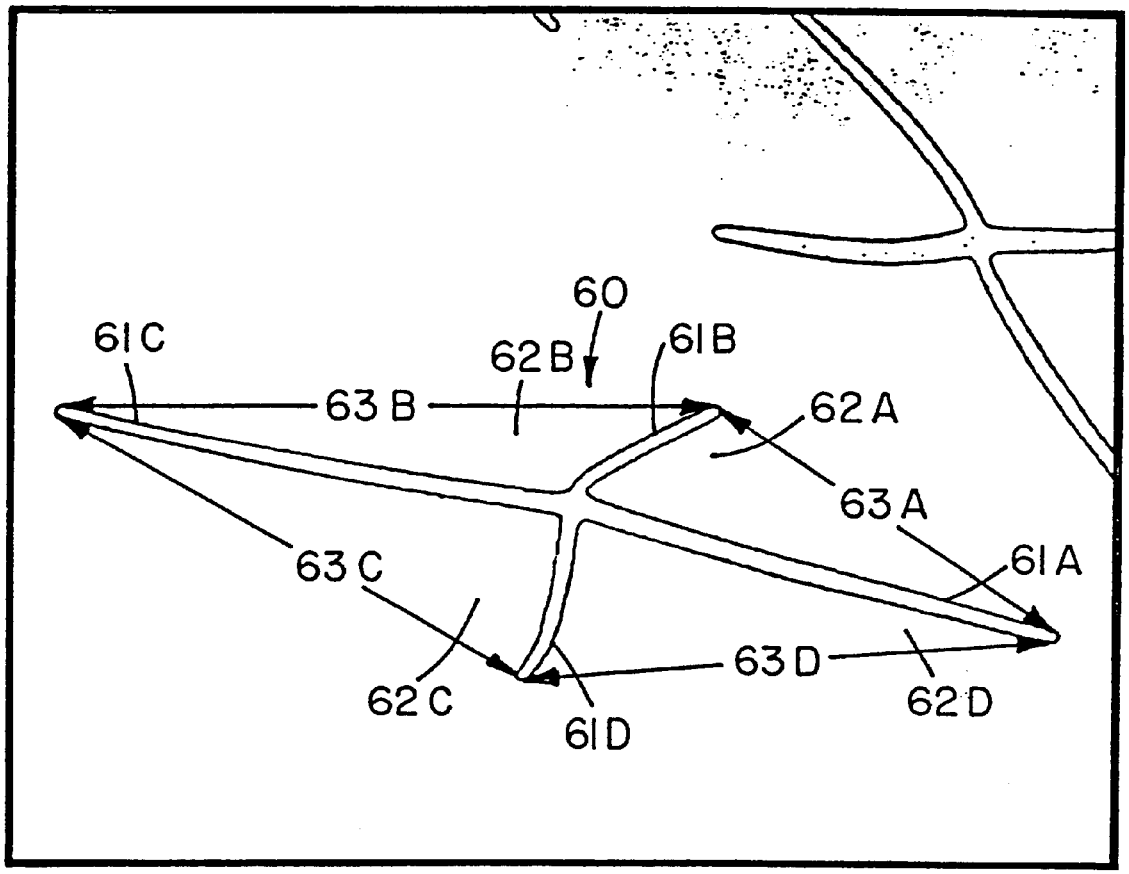
FIG. 6 is a photocopy of a photograph at a magnification of 158 of cross-sections of the fibers of example 3.

FIG. 6 is a photocopy of a photograph taken at a magnification of 158 showing a cross-section 60 of a polymer fiber of example 3. The polymer cross-section 60 includes the long arms 61A, 61C, and the short arms 61B, 61D. The arms 61A, 61B, 61C and 61D form channels 62A, 62B, 62C, and 62D, which have channel widths 63A, 63B, 63C, and 63D. Channels 62A, 62B, 62C, and 62D are substantially similar to one another due to their formation from the spinnerette having apertures that are each symmetric, as shown in FIG. 5D.

Figure 7A:
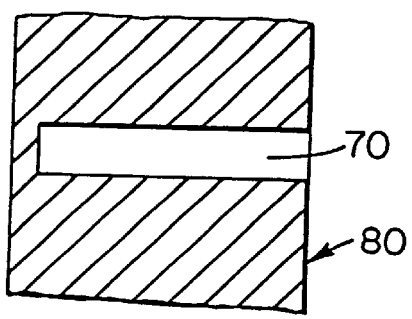
FIG. 7A is a partial sectional view showing a bore detail for an aperture of a spinnerette used in example 4.
Figure 7B:
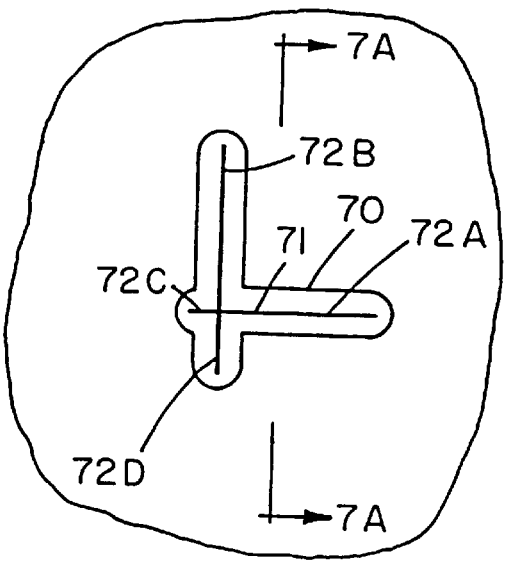
FIG. 7B is a plan view of a bore and an aperture of the spinnerette used in example 4.

FIG. 7A shows a partial side sectional view of a bore 70 for an aperture of the spinnerette of example 4 shown in FIG. 7B. The aperture is not shown.

Figure 7C:
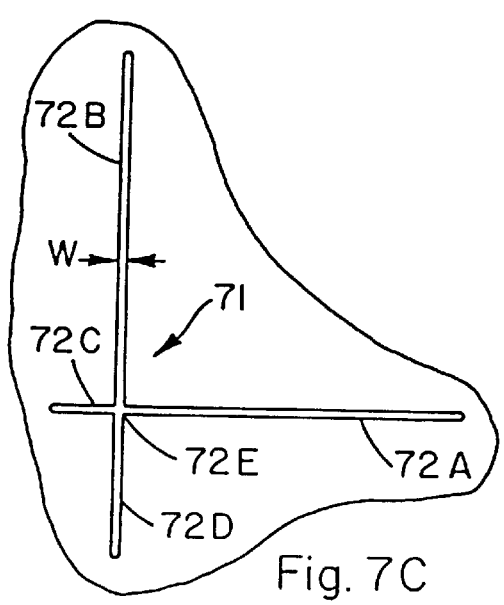
FIG. 7C is a schematic identifying relative dimensions of an aperture of the spinnerette used in example 4.

FIG. 7B shows the bore 70 and the aperture 71 of a spinnerette of example 4. FIG. 7B also shows the arms 72A, 72B, 72C, and 72D of the aperture 71. For the spinnerette used in example 4, the length 73 is about 0.62 inches, the length 74 is about 0.50 inches, the length 75 is about 0.065 inches, the length 77 is 0.80 inches, the length 76 is 0.93 inches, and the length 78 is 0.065 inches. The arms 72A, 72B, 72C, and 72D all extend from a common axis 72E as shown in FIG. 7C. Moreover, the arms 72A and 72C are co-linear, the arms 72B and 72D are co-linear, and the arms 72B and 72D are perpendicular to the arms 72A and 72C.

FIG. 7C is a schematic illustrating dimensions of the aperture 71. FIG. 7C shows the lengths of the arms 72A, 72B, 72C, and 72D as 183W, 196W, 40W, and 80W, respectively. W represents the width of each of the arms of the aperture 71. The width W is 0.067 millimeters (which is 2.6 mils) in aperture 71.

Figure 7D:
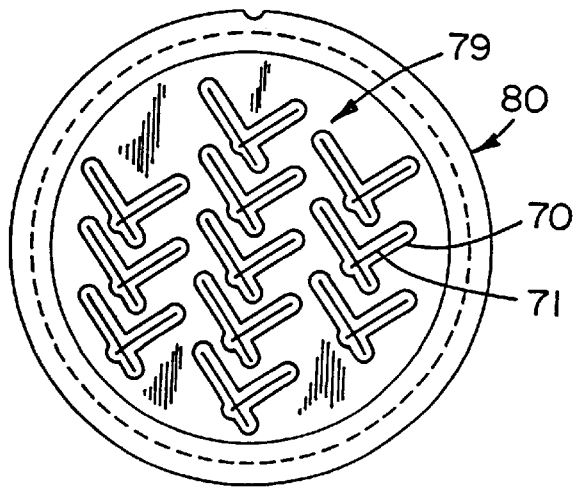
FIG. 7D is a plan view of an interior face of the spinnerette used in example 4 showing a bore and an aperture pattern.

FIG. 7D shows the spinnerette 80 having a pattern 79 of the bores 70 and the apertures 71 of example 4. There are eleven apertures 71 and a spinnerette face 80, and the apertures 71 are aligned in three rows in the spinnerette 80 to form the pattern 79.

Figure 8:
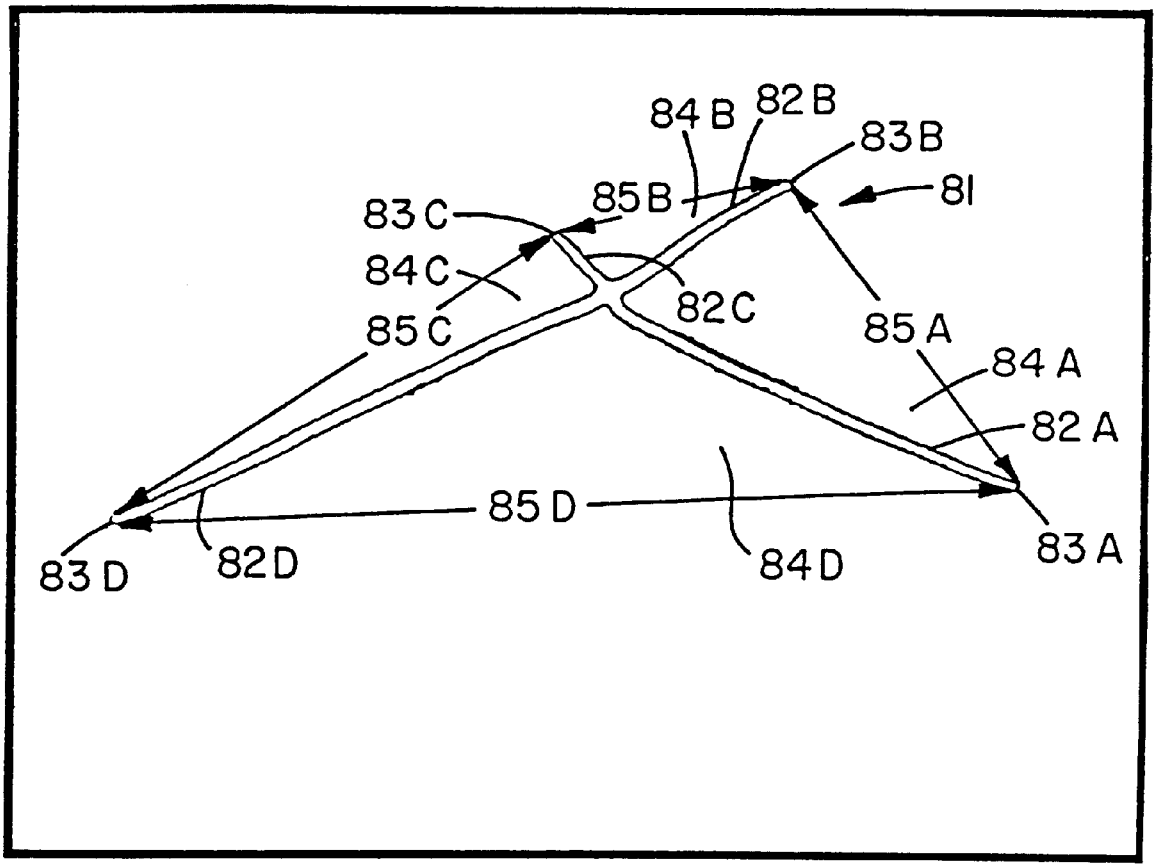
FIG. 8 is a photocopy of a photograph at a magnification of 158 of a cross-section of a fiber of example 4.

FIG. 8 shows a photocopy of a photograph taken at a magnification of 158 of a cross section 81 of a fiber of example 4 formed from the spinnerette shown in FIGS.

7A–7D. Cross-section 81 includes polymer arms 82A, 82B, 82C, and 82D. The polymer arms 82A–82D have distal tips 83A–83D, respectively. The polymer arms 82A–82D also define channels 84A–84D, as shown. The length between the distal tips 83A and 83B define the channel width 85A of the channel 84, which is also illustrated in FIG. 8. The channel width 85B is the length between the distal tips 83B and 83C. The channel width 85C is the length between the distal tips 83C and 83D. The channel width 85D is the length between the distal tips 83D and 83A. The fiber having the cross-section 81 shown in FIG. 8 is formed by extrusion from aperture of the spinnerette face 80 shown in FIG. 7D. The deviation of the angles between the polymer arms 82A–82D for the cross-section 81 from right angles is due to the extrusion process.

Figure 9A:
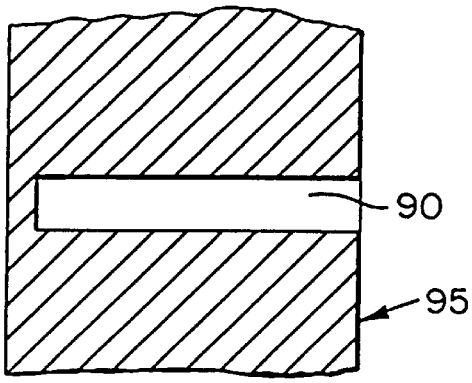
FIG. 9A is a partial sectional view showing a bore detail for an aperture of a spinnerette used in example 5.

FIG. 9A shows a bore 90 in a partial sectional view of the spinnerette used in example 5.

Figure 9B:
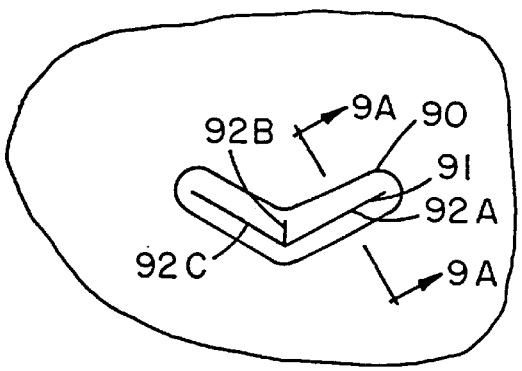
FIG. 9B is a plan view of a bore and an aperture of the spinnerette used in example 5.

FIG. 9B shows a plan view of the bore 90 and an aperture 91 of the spinnerette of example 5. The aperture 91 includes the arms 92A, 92B, and 92C.

Figure 9C:
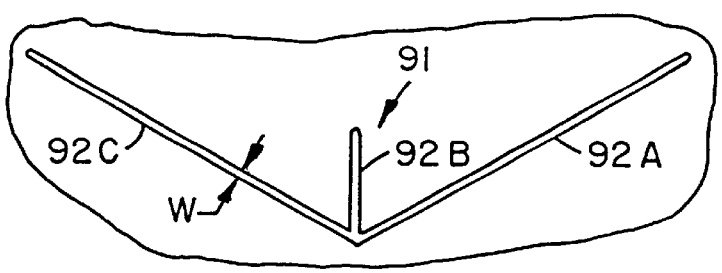
FIG. 9C is a schematic identifying the relative dimensions of an aperture of the spinnerette used in example 5.

FIG. 9C is a schematic identifying the relative dimensions of the aperture 91 of the spinnerette of example 5. FIG. 9C shows that the arms 92A and 92C define an angle of 120°, and that the arm 92B defines an angle of 60° with each of the arms 92A and 92C. Moreover, FIG. 9C shows that the arms 92A and 92C have lengths which are 100 times their widths, W, and that the arm 92B has a length that is 30 times its width, W. The width W in aperture 91 is 0.064 millimeters.

Figure 9D:
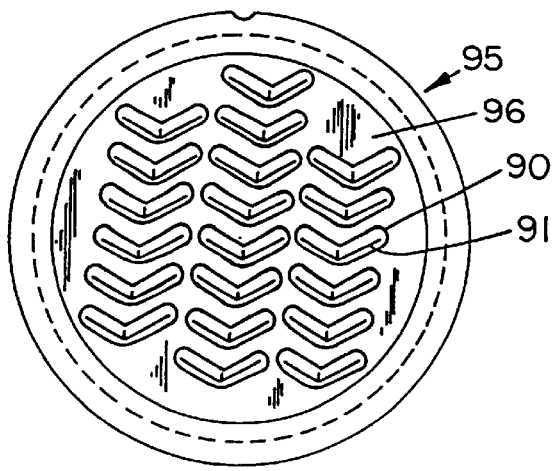
FIG. 9D is a plan view of an interior face of the spinnerette used in example 5 showing a bore and an aperture pattern.

FIG. 9D shows the spinnerette 95 used in example 5 having the face 96 and including twenty bores 90 in a pattern of three rows. The twenty apertures 91 shown in FIG. 9D are aligned in three rows such that locating points for the apertures in each row define a line.

FIG. 10 is a photocopy of a photograph taken at a magnification of 163 of a polymer cross-section 100 of a polymer fiber formed from the spinnerette 95 shown in FIGS. 9A–9D. The polymer cross-section 100 includes arms 101A, 101B, and 101C. The arms 101A, 101B, 101C, have distal tips 102A, 102B, and 102C, respectively. Arms 101A and 101B define channel 103 and arms 101B and 101C define channel 104. The length between distal tip 102A and 102B defines the channel width 103A. The length between the distal tip 102B and 102C defines the channel width 104A.

Figure 11A:
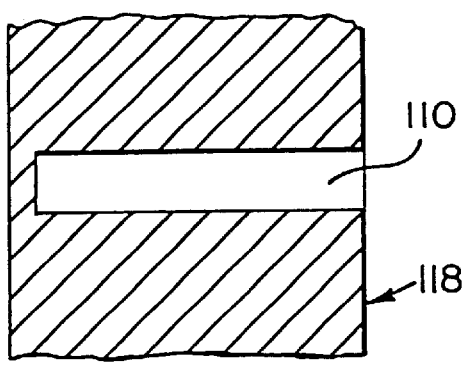
FIG. 11A is a partial sectional view showing a bore detail for an aperture of a spinnerette used in example 6.
Figure 11B:
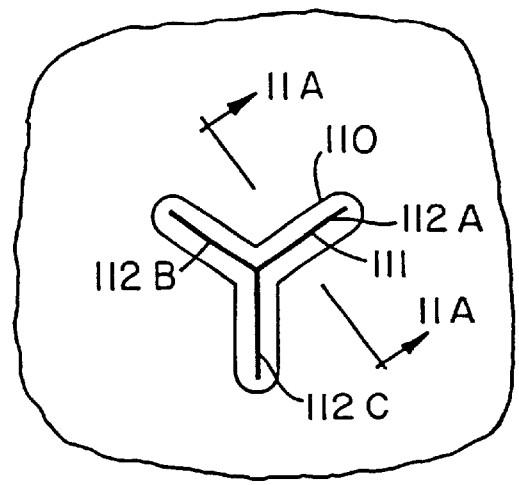
FIG. 11B is a plan view showing a bore and an aperture of the spinnerette used in example 6.

FIG. 11A is a partial sectional view showing the bore 110 for an aperture of the spinnerette 118 used in example 6.

Figure 11C:
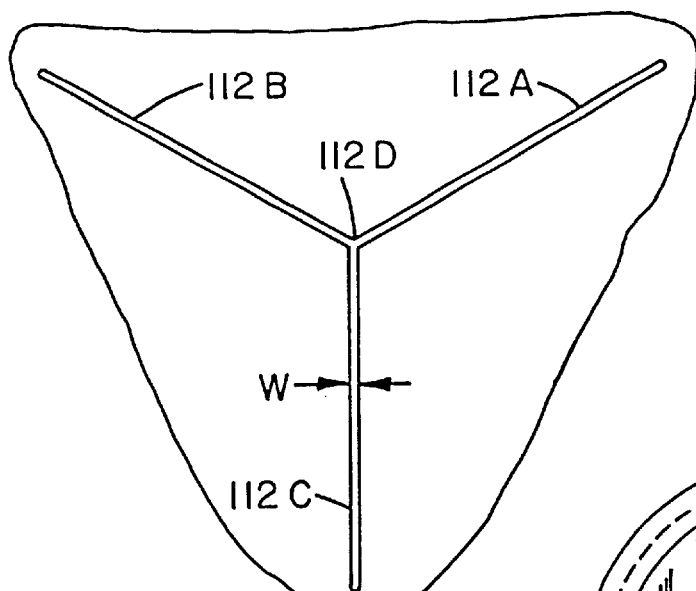
FIG. 11C is a schematic showing the relative dimensions of an aperture of the spinnerette used in example 6.

FIG. 11C is a schematic showing the dimension of aperture 111 of the spinnerette 118 used in example 6. FIG. 11C shows that the arms 112A, 112B, 112C all radiate from a common axis 112D and radiate at angles spaced by 120° from one another. FIG. 11C also shows that the arms 112A, 112B, and 112C have lengths that are 150 times their width, W. The width W is 0.067 millimeters in aperture 111.

Figure 11D:
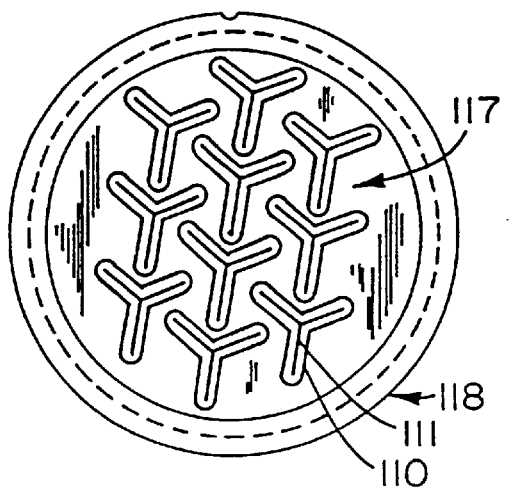
FIG. 11D is a plan view of an interior face of the spinnerette used in example 6 showing a bore and an aperture pattern.

FIG. 11D shows a spinnerette 118 used in example 6 having the bores 110 and the apertures 111 in the aperture pattern 117. The apertures 111 in the pattern 117 are aligned in three rows such that center points for apertures in each row define a line.

Figure 12:
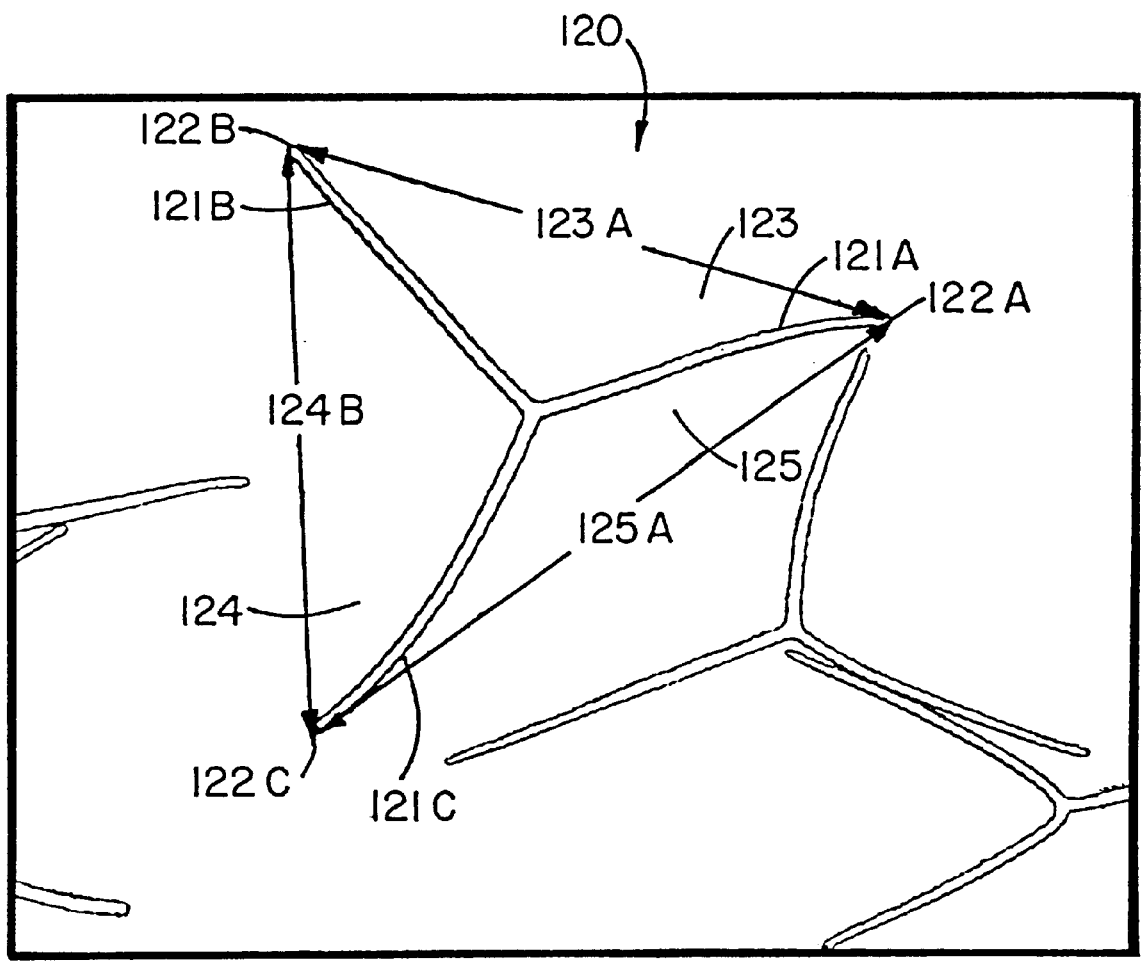
FIG. 12 is a photocopy of a photograph at a magnification of about 190 of a cross-section of a fiber of example 6.

FIG. 12 is a photocopy of a photograph at a magnification of about 190 of a polymer cross-section 120 of a fiber of example 6 formed using the spinnerette 118 shown in FIGS. 11A–11D. The polymer cross-section 120 includes the arms 121A, 121B, and 121C, which all radiate from a central point. The arms 121A, 121B, and 121C have distal tips 122A, 122B, and 122C, respectively. The arms 121A and 121B define channel 123. The arms 121B and 121C define the channel 124. Arms 121C and 121A define the channel 125. The length between the distal tips 122A and 122B defines the channel width 123A of channel 123. The length between the distal tips 122B and 122C defines the channel width 124B of the channel 124. The length between the distal tips 122C and 122A defines the channel width 125A of the channel 125. Channel 123 is defined by arms that define an angle of less than 120°. The channel 124 is also defined by arms that define an angle of less than 120°. The channel 125 is defined by arms that is define an angle of greater than 120°.

Figure 13A:
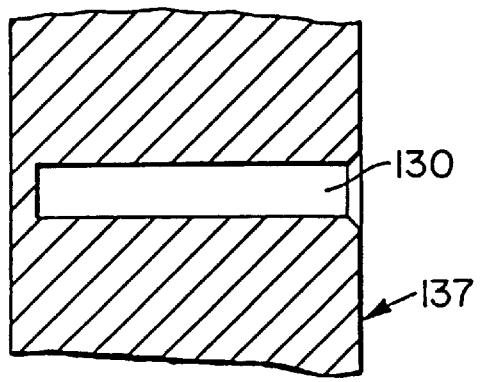
FIG. 13A is a partial sectional view showing a bore detail for an aperture of a spinnerette used in example 7.

FIG. 13A is a partial sectional view showing a bore 130 of the spinnerette 137 used in example 7.

Figure 13B:
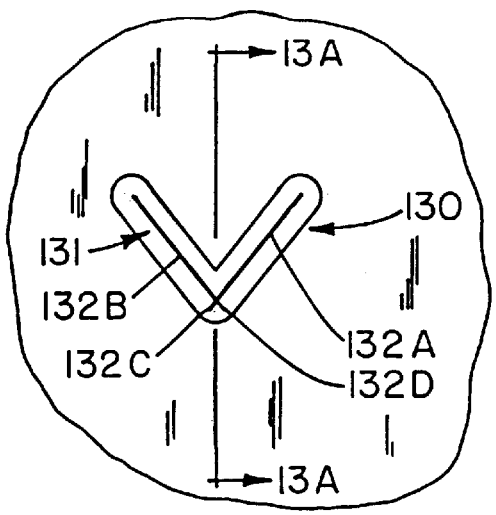
FIG. 13B is a plan view of a bore and an aperture of the spinnerette used in example 7.

FIG. 13B shows the bore 130 and an aperture 131 of the spinnerette 137 used in example 7 having arms 132A, 132B, 132C, and 132D.

Figure 13C:
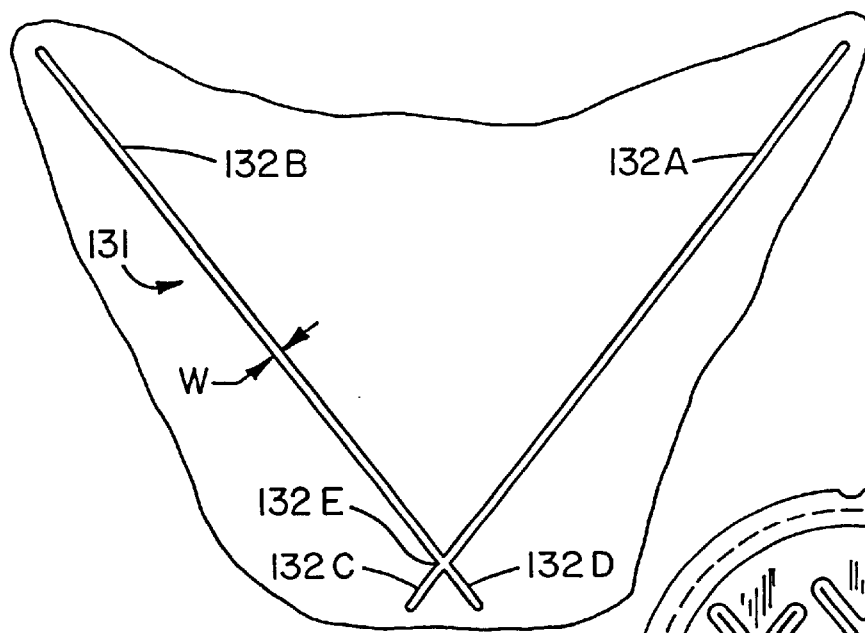
FIG. 13C is a schematic showing the relative dimensions of an aperture of the spinnerette used in example 7.

FIG. 13C is a schematic showing the dimensions of aperture 131 of example 7. FIG. 13C shows that the arms 132A and 132B have lengths that are 105 times their width, W, and that the arms 132C and 132D have lengths that are 15 times their width, W. In addition, FIG. 13C shows that arms 132A and 132B define an angle of 75° between them. The width W in aperture 131 is 0.084 millimeters. Arms 132A, 132B, 132C and 132D all radiate from a common axis 132E.

Figure 13D:
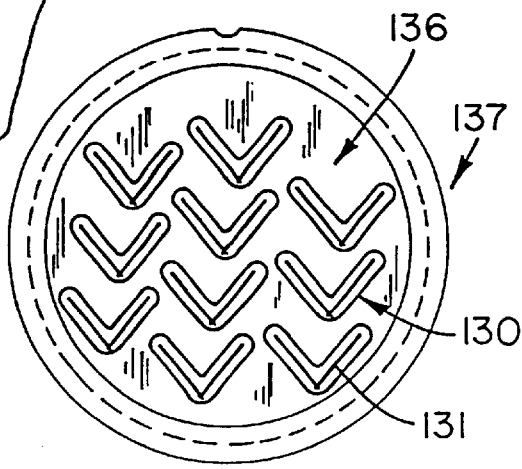
FIG. 13D is a plan view of an interior face of the spinnerette used in example 7 showing a bore and an aperture pattern.

FIG. 13D shows a spinnerette aperture pattern 136 including ten apertures 131 in the spinnerette 137. The apertures 131 in the spinnerette 137 are aligned so that all of the apertures 131 have the same orientation and form two rows of three apertures and one row of four apertures.

Figure 14:
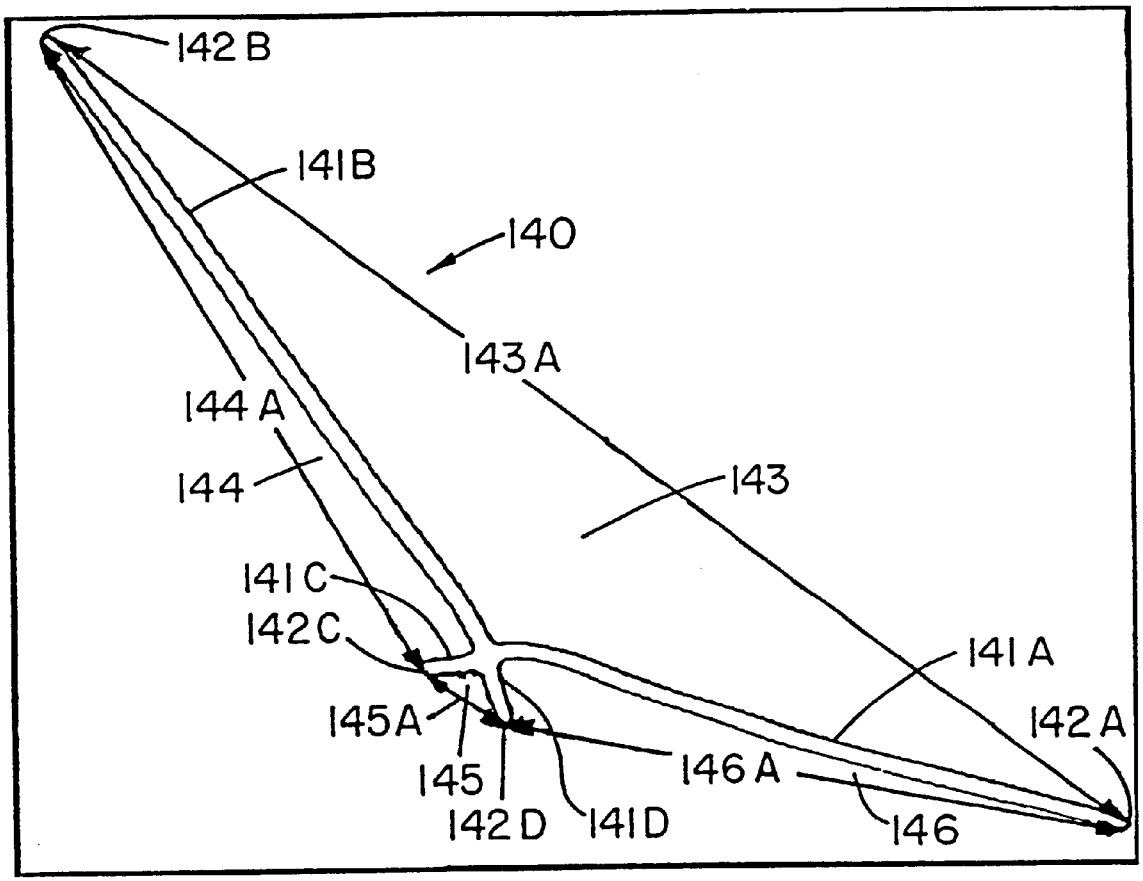
FIG. 14 is a photocopy of a photograph at a magnification of about 130 of a cross-section of a fiber of example 7.

FIG. 14 is a photocopy of a photograph at a magnification of about 130 of a polymer cross-section 140. The polymer cross-section 140 includes the arms 141A, 141B, 141C, and 141D. The arms 141A, 141B, 141C, and 141D have distal tips 142A, 142B, 142C, and 142D, respectively. The arms 141A and 141B are much longer than the arms 141C and 141D.

The arms 141A and 141B define a channel 143. The arms 141B and 141C define a channel 144. The arms 141C and 141D define a channel 145. The arms 141D and 141A define a channel 146. The width 143A of the channel 143 is defined by the length between the distal tips 142A and 142B. The width 144A of the channel 144 is defined by the length between the distal tips 142B and 142C. The width 145A of channel 145 is defined as the length between the distal tips 142C and 142D. The width 146A of the channel 146 is defined as the length between the distal tips 142D and 142A.

Figure 15A:
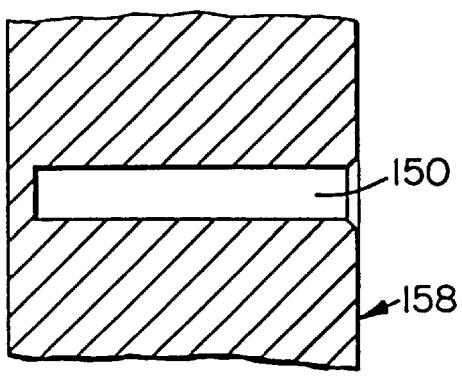
FIG. 15A is a partial sectional view of a bore detail for an aperture of a spinnerette used in example 8.
Figure 15B:
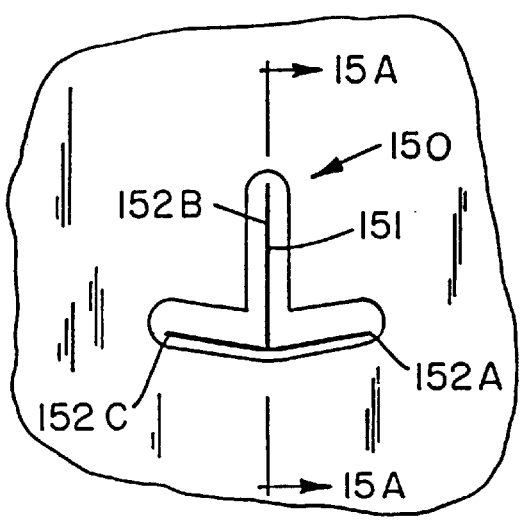
FIG. 15B is a plan view showing a bore and an aperture of the spinnerette used in example 8.

FIG. 15A is a partial sectional view of the spinnerette 158 used in example 8 showing the bore 150.

Figure 15C:
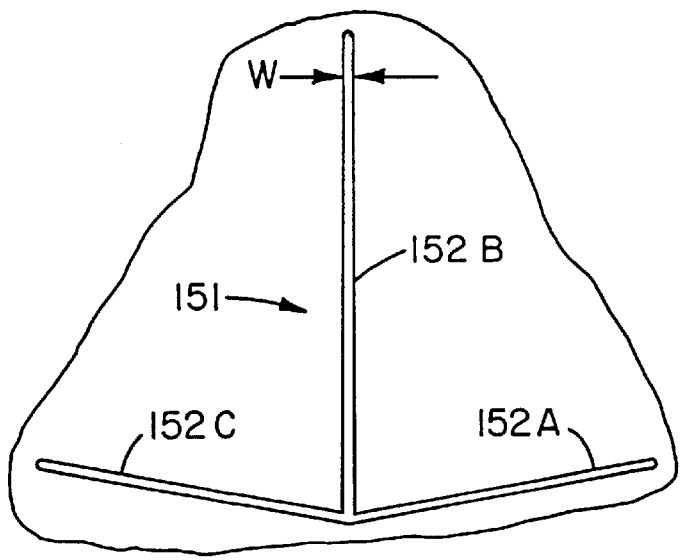
FIG. 15C is a schematic identifying the relative dimensions of the aperture of the spinnerette used in example 8.

FIG. 15C is a schematic identifying the relative dimensions of the aperture 151 in the spinnerette 158 used in example 8. FIG. 15C shows that the length of the arm 152A is 100 times its width, W, the length of the arm 152B is 160 times its width, W, and that the length of the arm 152C is 100 times its width, W. In addition, FIG. 15C shows that the arms 152A and 152C each form an angle of 80° with the arm 152B. The width W is 0.084 millimeters in the aperture 151. Arms 152A, 152B and 152C all radiate from a common axis 152D.

Figure 15D:
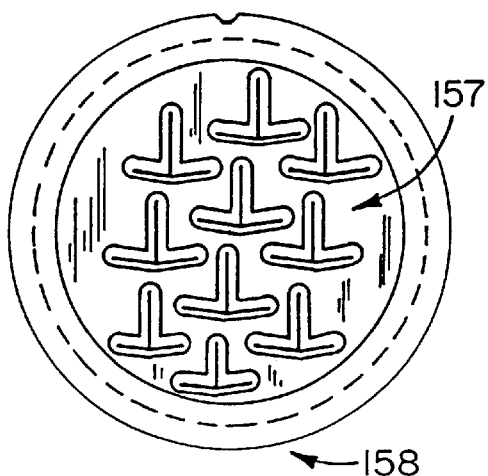
FIG. 15D is a plan view of an interior face of the spinnerette used in example 8 showing a bore and an aperture pattern.

FIG. 15D is a plan view showing the spinnerette 158 having the spinnerette aperture pattern 157 having ten apertures 151. All of the apertures 151 in the spinnerette aperture pattern 157 are oriented in the same direction.

Figure 16:
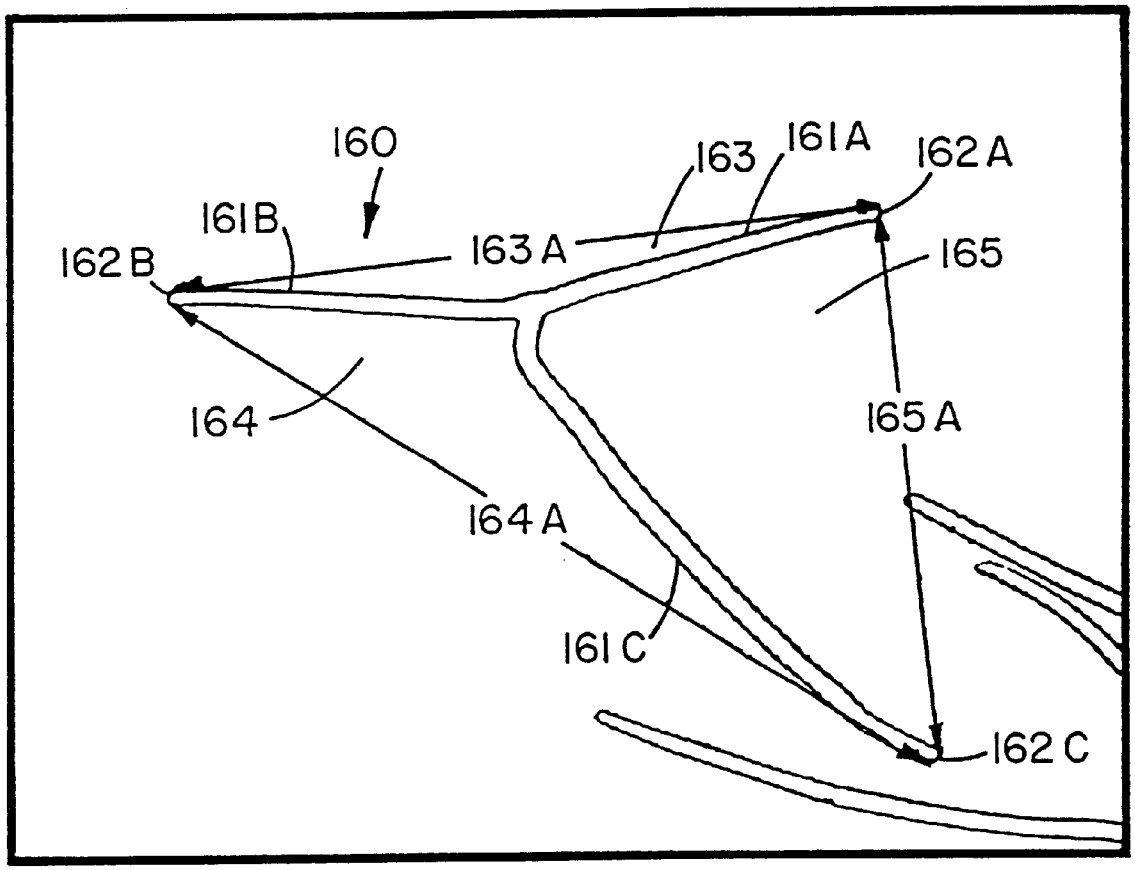
FIG. 16 is a photocopy of a photograph at a magnification of about 230 of a cross-section of a fiber of example 8.

FIG. 16 is a photocopy of a photograph taken at a magnification of about 230 of a polymer cross-section 160 of a fiber of example 8 formed using the spinnerette shown in FIGS. 15A–15D. The polymer cross-section 160 includes the arms 161A, 161B, and 161C. The arms 161A, 161B, and 161C each have distal tips 162A, 162B, and 162C. The arms 161A and 161B define the channel 163. The arms 161B and 161C define the channel 164. The arms 161C and 161A define the channel 165. The width 163A of the channel 163 is defined by the length between the distal tips 162A and 162B. The width 164A of the channel 164 is defined by the length between the distal tips 162B and 162C. The width 165A of the channel 165 is defined by the length between the distal tips 162C and 162A.

FIG. 17A is a partial sectional view of the spinnerette 181 used in example 9 showing the bore 170. The dimension 171 is 0.050 inches and bevel 172 is 0.010 inches at 45° for the spinnerette 181 used in example 9.

FIG. 17B is a plan view of the bore 170 and an aperture 173 of the spinnerette 181 used to make the fibers of example 9. The aperture 173 in the bore 170 defines a curved section 174 and the protrusions 175.

FIG. 17C shows that the radius at the center of the curved section of the aperture 173 is about 138 times the width W of the curved section of the aperture. FIG. 17C shows that the distance from the center point defined by the curved section 173 to the distal tips 179 of the protrusions 175 is about 143 times the width W of the curved section 174 of the aperture 173. In addition, FIG. 17C also shows that the protrusions 179 are spaced at 5° intervals from one another. The width W is 0.067 millimeters in the aperture 173.

FIG. 17D is a plan view showing the spinnerette 181 used in example 9 and the spinnerette aperture pattern 180. There are twelve bores 170 and apertures 173 in the aperture pattern 180. The twelve apertures are aligned along three rows. The center row is defined by six aligned apertures. The outer two rows are defined by three aligned apertures.

Figure 18:
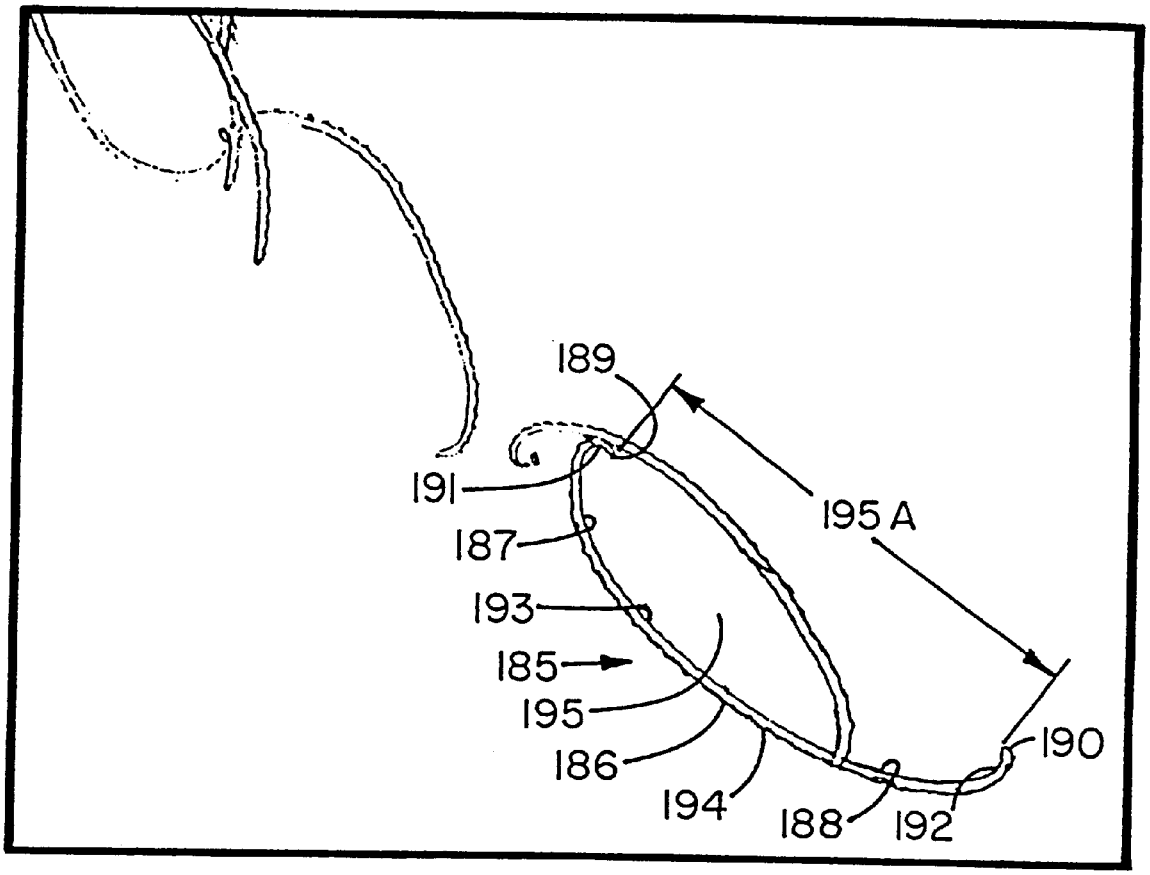
FIG. 18 is a photocopy of a photograph at a magnification of about 87 of a cross-section of a fiber of example 9.

FIG. 18 is a photocopy of a photograph at a magnification of about 87 of polymer cross-sections including the polymer cross-section 185 formed using the spinnerette shown in FIGS. 17A–17D. The polymer cross-section 185 does not have a planar wall. However, the polymer section 185 has a center section 186 with a first curvature, side sections 187 and 188 having a second curvature that is greater than the first curvature, and distal tips 189 and 190. Near the distal tips 189 and 190 are surfaces 191 and 192 the tangents to which intersect the inner surface 193. The surfaces 191 and 192 oppose the inner surface 193. The inner surface 193 is relatively smooth compared to the relatively rough outer surface 194. The roughness of the relatively rough surface 194 is due to the presence of the protrusions 175 in the aperture 173 during the extrusion from the spinnerette 181 during the spinning of the fiber of example 9. Although the surfaces 191 and 192 oppose the inner surface 193 in the fiber of example 9, that opposition is not necessary. That is, the outer ends of the polymer cross-section 185 may be oriented so that the surfaces 191 and 192 near the distal tips 189 and 190 of the polymer cross-section do not oppose other portions of the cross-section. The polymer cross-section 185 has a shape that looks like the letter "C". The surface 191 is continuous with the inner surface 193, and the inner surface 193 is continuous with the surface 192. The surfaces 191, 192, and 193 define the channel 195. The channel width 195A of the channel 195 is defined as the distance between the distal tips 189 and 190 of the polymer cross-section 185.

Figure 19:
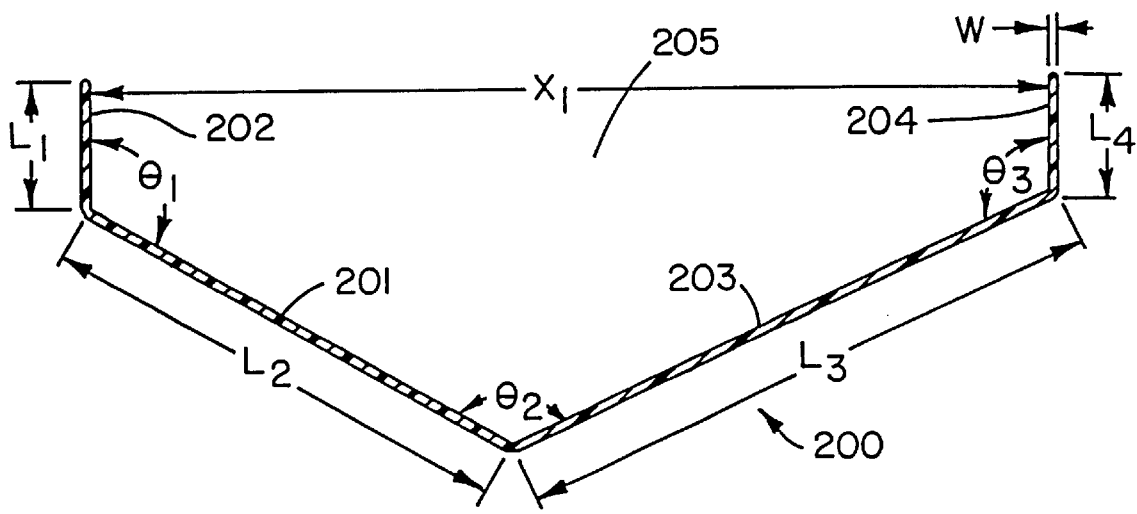
FIG. 19A is a schematic of a fiber cross-section of prophetic example 10 showing generalized dimensions of the cross-section.
FIG. 19B is a schematic of fiber cross-section of prophetic example 10 which will result from the spinnerette aperture shown in FIG. 19C.
FIG. 19C is a plan view of an aperture of a spinnerette of prophetic example 10.
Figure 19:
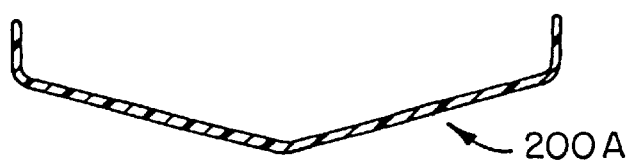
Figure 19:
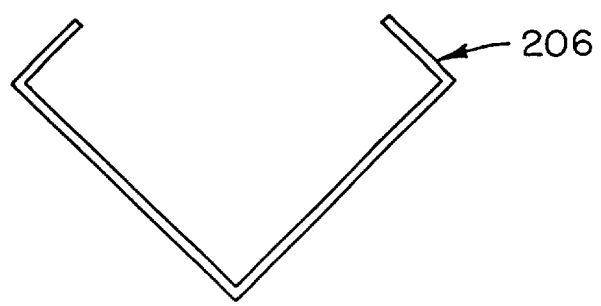

FIG. 19A shows the generalized version for the polymer cross-section 200 of a fiber of prophetic example 10. FIG. 19A includes the first arm inner section 201, the first arm outer section 202, the second arm inner section 203, and the second arm outer section 204. The length of the first arm inner section is shown as $L_2$, the length of the first arm outer section shown as $L_1$, the length of the second arm inner section is shown as $L_3$, and the length of the second arm outer section is shown as $L_4$. FIG. 19A also shows that the width of each of the arm sections is W, that the angle defined by the inner arm sections 201, 203 is $\theta_2$, that the angle defined by the first inner arm section 201 and the second inner arm section 202 is $\theta_1$, and that the angle defined by the second inner arm section 203 and the second outer arm section 204 is $\theta_3$. The arm sections 201, 202, 203, and 204 define the channel 205. The width of the channel 205 at its mouth is identified in FIG. 19A as $X_1$.

FIG. 19B is another schematic of a polymer cross-section 200A of a fiber of prophetic example 10 having different values for the parameters than the parameters shown for the cross-section 205 in FIG. 19A.

FIG. 19C shows a plan view of an aperture 206 of a spinnerette than can be used to make the polymer cross-sections 200 and 200A.

Preferably, for prophetic example 10, $\theta_1$, $\theta_2$, and $\theta_3$ are between 110° and 140°. Preferably, $L_2/W$ is greater than or equal to 5. Preferably $L_3/W$ is greater than or equal to 5. Preferably $L_1/W$ is less than or equal to 10. Preferably $L_4/W$ is less than or equal to 10. Preferably the bulk factor of the polymer fiber having the cross-section 200 is greater than or equal to 4. Preferably the width W of the polymer cross-section 200 is greater than or equal to 3 microns and is less than or equal to 15 microns. Preferably, the adhesion tension of distilled water on the surface of the polymer fiber having the cross-section 200 of prophetic example 10 is greater than 25 dynes per centimeter with distilled water.

More preferably, the angles $\theta_1$, $\theta_2$ and $\theta_3$ are all about 120°. More preferably, $X_1$ is greater than or equal to 250 microns, and even more preferably greater than 300 microns. More preferably, $L_2$ equals $L_3$ and $L_1$ equals $L_4$.

Preferably, $\theta_1$ and $\theta_3$ are each less than the quantity of 180° minus one half of $\theta_2$. This relationship provides the outer arms 202 and 204 angled towards one another such that the mouth of the channel 205 is narrower than the wide point of the cross-section. That narrowing at the mouth of the channel inhibits registration of adjacent fibers in which the inter-fiber capillaries are much less than the depth of the channel 205.

Moreover, each of the arm sections 201, 202, 203, and 204 may include protrusions having a width of about W and a length of protrusion extending no more than 3W. Moreover, the ratio of $L_2$ to $L_3$ should be between 0.5 and 2.0. Moreover, the ratio between $L_4$ and $L_1$ should be between 0.5 and 2.0.

The foregoing relationships between the angles $\theta_1$, $\theta_2$, and $\theta_3$, the lengths $L_1$, $L_2$, $L_3$, and $L_4$, and the width W, and the absolute values for the lengths and widths identified above are believed to provide fibers having novel large values for the maximum potential flux for bundles of fibers.

Figure 20:
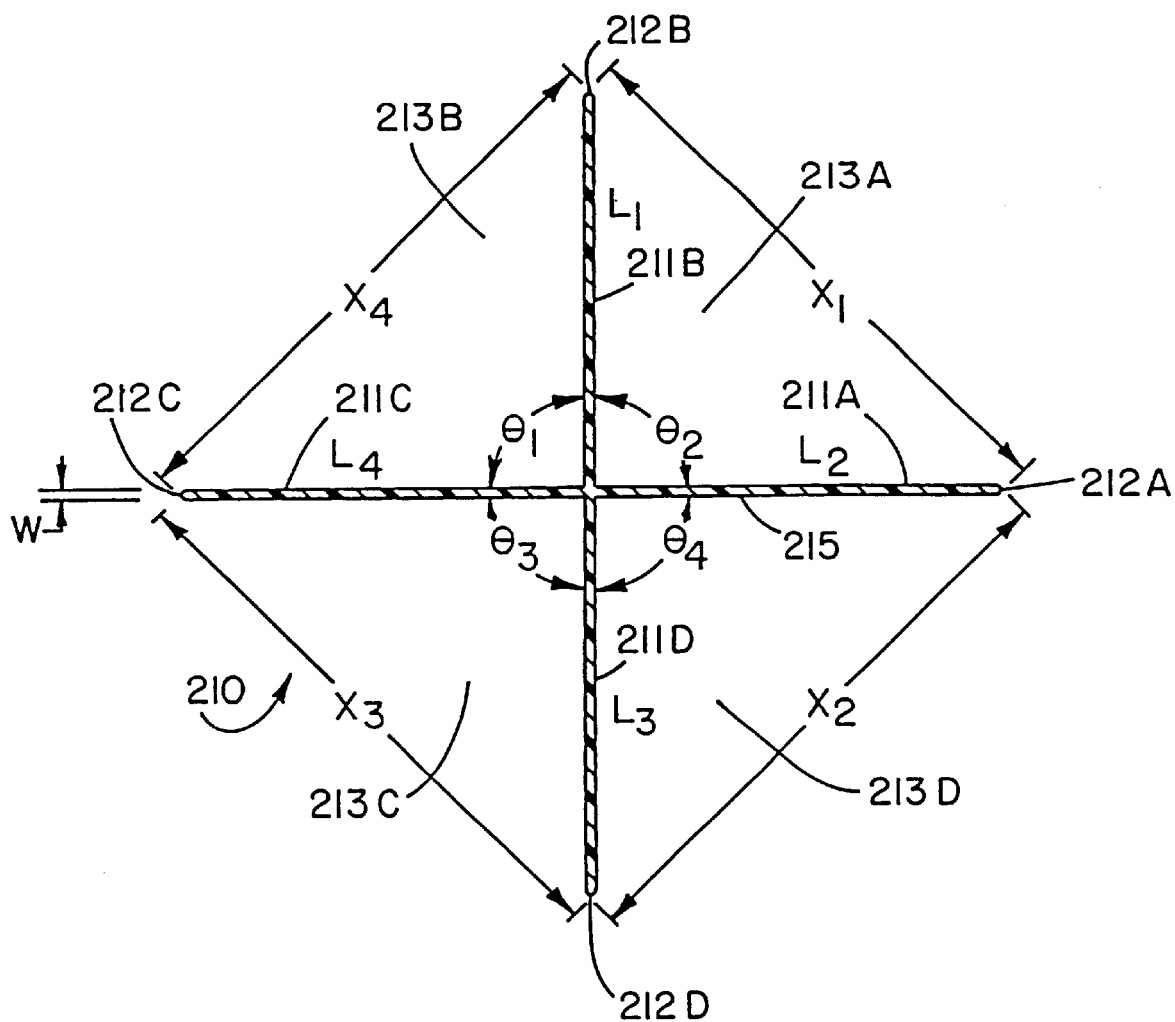
FIG. 20 is a schematic of a fiber cross-section showing generalized dimensions for the cross-section of a fiber of example 3.

FIG. 20 is a schematic showing the dimensions of the polymer cross-section 210 of another prophetic example having the generalized version of the cross-section 60 shown in FIG. 6 for the fiber of example 3. The polymer cross-section 210 includes the arms 211A, 211B, 211C, and 211D. The arms 211A, 211B, 211C, and 211D, have the distal tips 212A, 212B, 212C, and 212D. The arms 211A, 211B, 211C, 211D define the channels 213A, 213B, 213C, and 213D. The length of the arms 211A, 211B, 211C, and 211D are illustrated in FIG. 20 as $L_2$, $L_1$, $L_4$ and $L_3$ respectively. The channel width, which is defined as the width between the distal tips of the walls defining the channel are illustrated in FIG. 20 as $X_1$ for the channel 213A, $X_4$ for the channel 213B, $X_3$ for the channel 213C, and $X_2$ for the channel 213D. The width throughout the polymer cross-section 210 is defined as W.

Preferably, for the cross-section 210, the angles $\theta_1$, $\theta_2$, $\theta_3$, $\theta_4$ are all approximately 90°. Preferably, all four angles are between 70° and 110°. Preferably, the ratios of the lengths L to the width W is greater than 5 for $L_1$, $L_2$, $L_3$, and $L_4$. Preferably, at least one of the ratios between the lengths $L_1$ and $L_4$ to the width W is greater than 10. Preferably, the bulk factor of the fiber having the polymer cross-section 210 is greater than 4.0. Preferably, the width W is greater than 3 microns and less than or equal to 15 microns. Preferably, the adhesion tension with distilled water on the surface of the fiber having the cross-section 210 is greater than 25 dynes per centimeter. Preferably, the channel width $x_1$ is greater than 250 microns, and more preferably greater than about 300 microns. Preferably, the lengths $L_2$ equals the length $L_3$ and the length $L_1$ equals the length $L_4$.

Preferably, for the cross-section 210, the angles $\theta_1$ and $\theta_2$ are less than the quantity defined by 180° minus one half of the angle $\theta_2$. This relationship between $\theta_1$ and $\theta_2$ inhibits registration, thereby preventing capillaries that are too narrow.

In addition, each of the arms 211A, 211B, 211C, and 211D may have one or more protrusions there along in which each of the protrusions has a width of approximately W and is no more than about 3W long. In addition, the ratio of the length $L_2$ to the length $L_3$ and the ratio of the length $L_4$ to the length $L_1$ should be between about 0.5 and about 2.0.

Figure 21A:
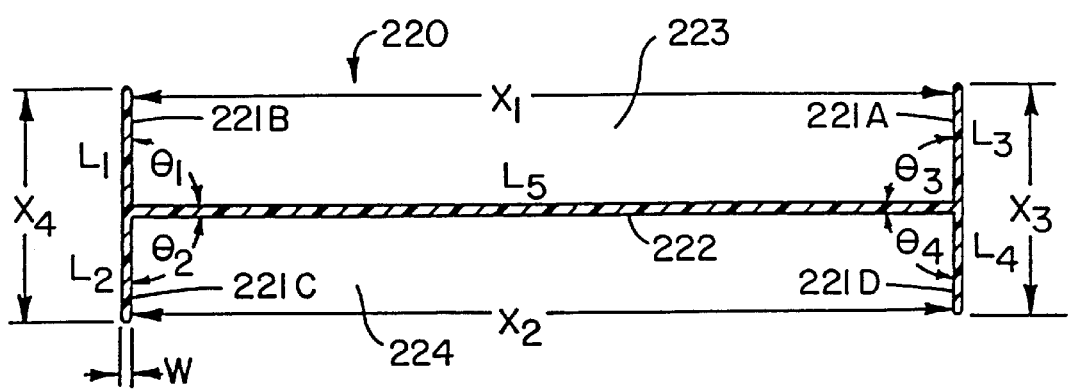
FIG. 21A is a schematic of a fiber cross-section of prophetic example 11 showing the generalized dimensions of the cross-section.

FIG. 21A shows the generalized version of the fiber cross-section 220 of prophetic example 11. Cross-section 220 includes the arms 221A, 221B, 221C, and 221D, and base 222. The base 222, the arm 221A, and the arm 221B define the channel 223. The base 222, the arm 221C, and the arm 221D define the channel 224. FIG. 21A illustrates the length of the base 222 as $L_5$, and the length of the arms 221A, 221B, 221C, and 221D, as $L_3$, $L_1$, $L_2$, $L_4$, respectively. FIG. 21A illustrates the angles between the base 222 and the walls 221A, 221B, 221C, and 221D as $\theta_3$, $\theta_1$, $\theta_2$, $\theta_4$, respectively, and defines the width of the fiber as W.

Preferably, the angles $\theta_1$, $\theta_2$, $\theta_3$, $\theta_4$ are greater than or equal to 60° and less than or equal to 120°. Preferably, the ratios of the lengths of each of the walls, $L_1$, $L_2$, $L_3$, $L_4$ to the length of the base $L_5$ is less than or equal to 0.3. Preferably, the ratio of the lengths of each of the walls $L_1$, $L_2$, $L_3$, $L_4$ to the width W is greater than or equal to 5. Preferably, the length of the base $L_5$ to the width W is equal to or greater than 10. Preferably, the width W is less than or equal to 15 microns, more preferably less than 10 microns, and still more preferably less than 5 microns, but wide enough to provide sufficient stiffness to the fibers' cross-sections so that the fibers' cross-sections do not substantially deform and collapse the capillaries due to the capillary forces pressing the fibers together. However, the thinnest structures which can be made using state of the art spinnerette technology and state of the art extrusion processes have shown no evidence of any such collapse under capillary forces. The thinnest structures that can be fabricated have widths W of about 3 microns. The thinner the width W the less polymer material is needed to provide the distribution function. The relationship of polymer material is represented in the $MPF_B$ through the $MPF_B$'s dependence upon the specific volume.

Figure 25:
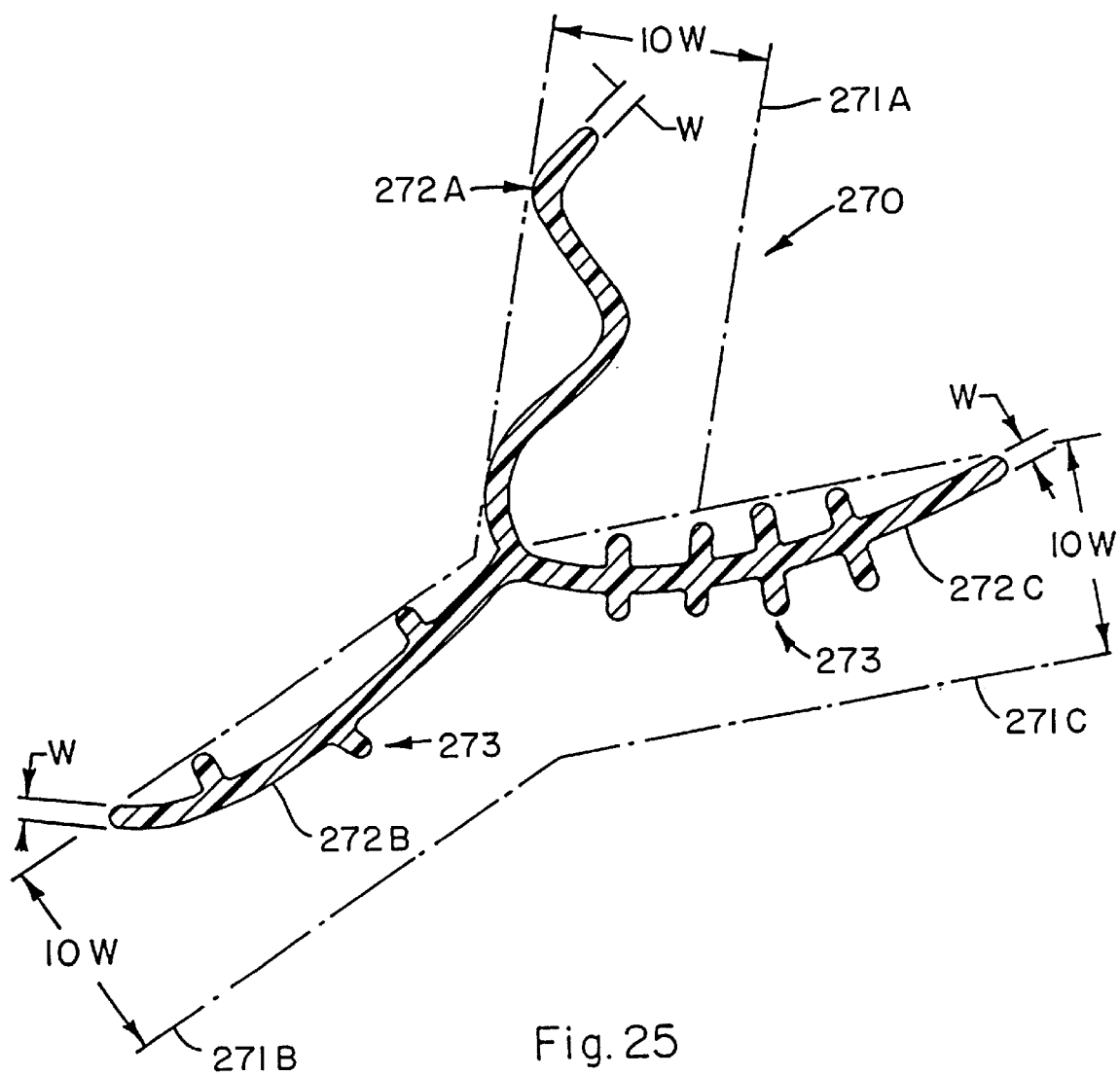
FIG. 25 is a schematic of a cross-section of a fiber of the invention showing additional features in the cross-sections of fibers of the invention.

Preferably, the adhesion tension of the surface of the fiber with distilled water is equal to or greater than 25 dynes/cm. More preferably, both of the channels' widths $X_2$ and $X_1$ are equal to or greater than 250 microns, and more preferably are equal to or greater than 300 microns. More preferably, $L_1$, $L_2$, $L_3$, $L_4$ are all approximately equal. Preferably, each of the ratios $L_1/_2$ and $L_3/L_4$ are equal to or greater than 0.5 and less than or equal to 2.0. Each of the arms 221A–221D may have protrusion of up to 3W long. Any such protrusion along with each arm of the fiber should preferably fit within a 10W wide pair of parallel lines delimiting the arm of the fiber, as shown in FIG. 25.

Figure 21B:
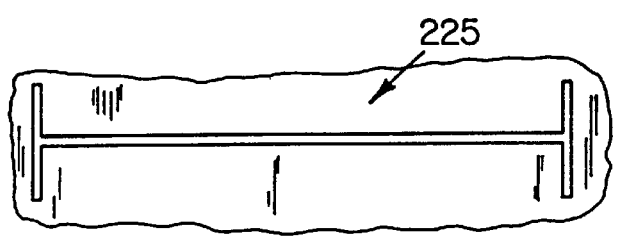
FIG. 21B is a schematic plan view of the shape of a spinnerette aperture the use of which will result in a fiber having the cross-section shown in FIG. 21C.

FIG. 21B is a schematic plan view of the shape of a spinnerette aperture 225 the use of which will result in a fiber having the cross-section 226.

Figure 21C:
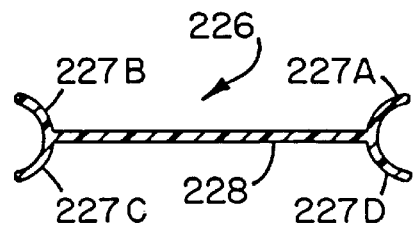
FIG. 21C is a schematic of a fiber cross-section of prophetic example 11 which will form when using the spinnerette aperture shown in FIG. 21B.

FIG. 21C shows the fiber cross-section 226 of the prophetic example 11. The curvature of the outer arms 227A, 227B, 227C, and 227D away from the base 228 results from the surface tensions during the extrusion process.

Figure 21D:
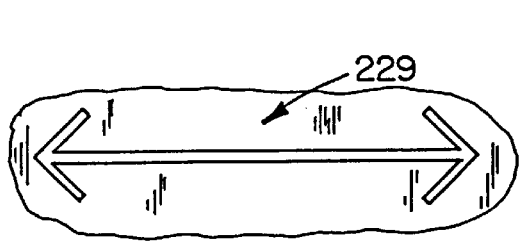
FIG. 21D is a schematic plan view of an aperture of a spinnerette for use in prophetic example 11 which will produce a fiber whose shape is similar to the shape shown in FIG. 21A with all of the θ angles being 90°.

FIG. 21D is a schematic plan view showing the shape of a spinnerette aperture 229 the use of which will result in a fiber having the cross-section 220 shown in FIG. 21A with the $\theta$ angles all being 90°.

Figure 21E:
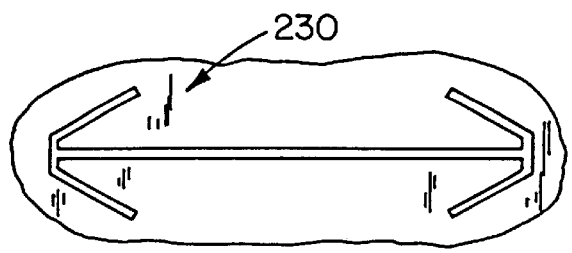
FIG. 21E is a plan view of an aperture of a spinnerette for prophetic example 11 which will produce a fiber whose shape is similar to the shape shown in FIG. 21A with all of the θ angles being 90°.

FIG. 21E is a schematic plan view showing the shape of the spinnerette aperture 230 the use of which will result in a fiber having the cross-section 220 shown in FIG. 21A with the $\theta$ angles all being 90°.

Figure 21F:
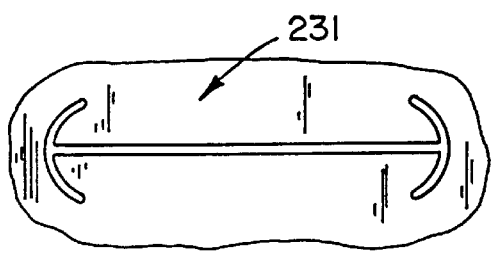
FIG. 21F is a schematic plan view of an aperture of a spinnerette for prophetic example 11 which will produce a fiber whose shape is similar to the shape shown in FIG. 21A with all of the θ angles being 90°.

FIG. 21F is a schematic plan view showing the shape of the spinnerette aperture 231 the use of which will result in a fiber having the cross-section 220 shown in FIG. 21A with the $\theta$ angles all being 90°.

Figure 21G:
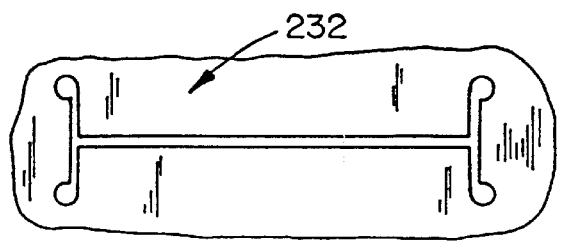
FIG. 21G is a plan view of an aperture of a spinnerette for prophetic example 11 which will produce a fiber whose shape is similar to the shape shown in FIG. 21A with all of the θ angles being 90°.

FIG. 21G is a schematic plan view showing the shape of the spinnerette aperture 232 the use of which will result in a fiber having the cross-section 220 shown in FIG. 21A with the $\theta$ angles all being 90°.

Figure 22A:
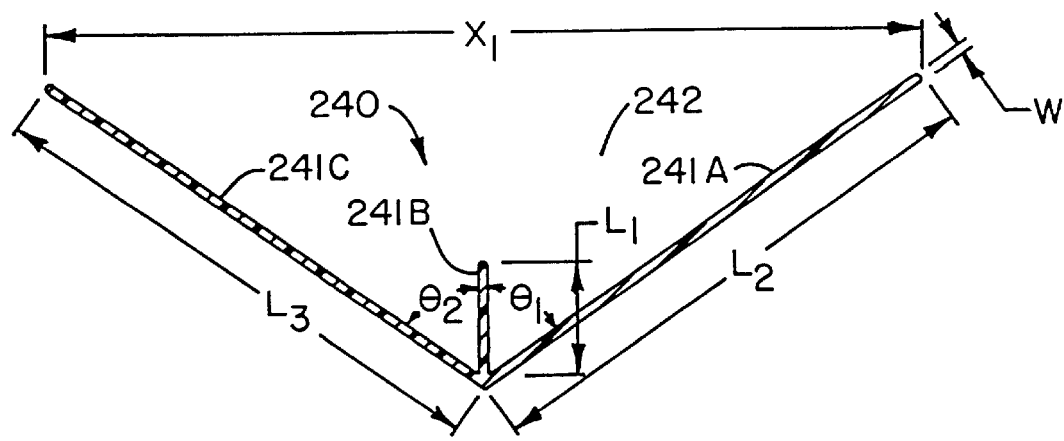
FIG. 22A is a schematic of a cross-section of a fiber showing generalized dimensions of cross-sections of the fibers of example 5.

FIG. 22A is a schematic of a cross-section 240 of a fiber showing the generalized version of the dimensions of cross-sections of the fibers of example 5. The cross-section 240 includes the arms 241A, 241B, and 241C whose lengths $L_1$, $L_2$, and $L_3$ are illustrated in FIG. 22A. The arms 241A and 241C have distal ends which define the channel 242 having the channel width $X_1$ illustrated in FIG. 22A. The arms 241A and 241B define the angle $\theta_1$ and the arms 241B and 241C define the angle $\theta_2$.

The fibers having the cross-sections 240 preferably have the angles $\theta_1$ plus $\theta_2$ being greater than or equal to 90° and less than or equal to 170°. Preferably, the ratio of each of the lengths $L_1$ and $L_2$ to the width W is equal to or greater than 5, and at least one of these two ratios is equal to or greater than 10. Preferably, at least one of the ratios of $L_3/L_1$ and $L_2/L_1$ is equal to or greater than 5. Preferably, the bulk factor of the fiber is equal to or greater than 3.0. Preferably, the width W is less than or equal to 15 microns, more preferably less than 10 microns, and still more preferably less than 5 microns, and the adhesion tension is equal to or greater than 25 dynes/cm with distilled water.

Additional distinguishing characteristics of fibers defined by the generalized cross-section 240 of FIG. 22A are that $X_1$ is greater than about 250 microns, and more preferably greater than about 300 microns, that the sum of $\theta_1$ plus $\theta_2$ is between 100° and 140°, that $\theta_1$ is about equal to $\theta_2$, and that the ratio of $L_2/L_3$ is between about 0.5 and 2.0.

Moreover, the fibers defined by the generalized cross-section in FIG. 22A may have one or more protrusions along their length. Each such protrusion may be approximately W wide and no more than 3W long. Further, the arms having the protrusion should fit within a 10W wide corridor, as shown in FIG. 25.

Figure 22B:
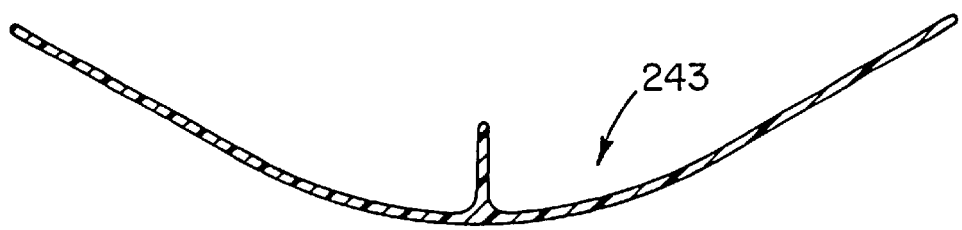
FIG. 22B is a schematic of a cross-section of a fiber having the generalized shape of fibers of example 5 and that will result from the spinnerette aperture shown in FIG. 22C.
Figure 22C:
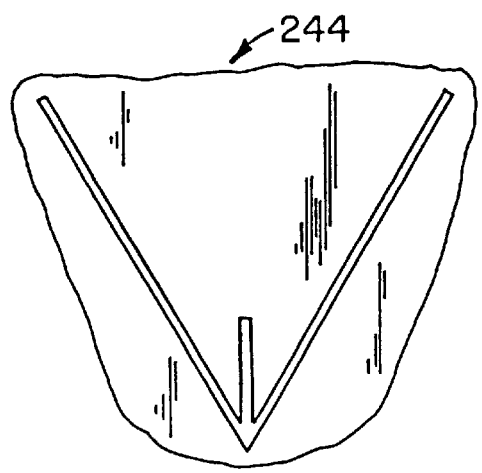
FIG. 22C is a schematic of an aperture of a spinnerette the use of which will result in a fiber having the cross-section shown in FIG. 22B.

FIG. 22B shows the prophetic fiber cross-section 243 which will result from use of the spinnerette aperture 244 shown in FIG. 22C because of the effects of surface tension on the molten polymer.

FIG. 22C shows the spinnerette aperture 244.

Figure 23:
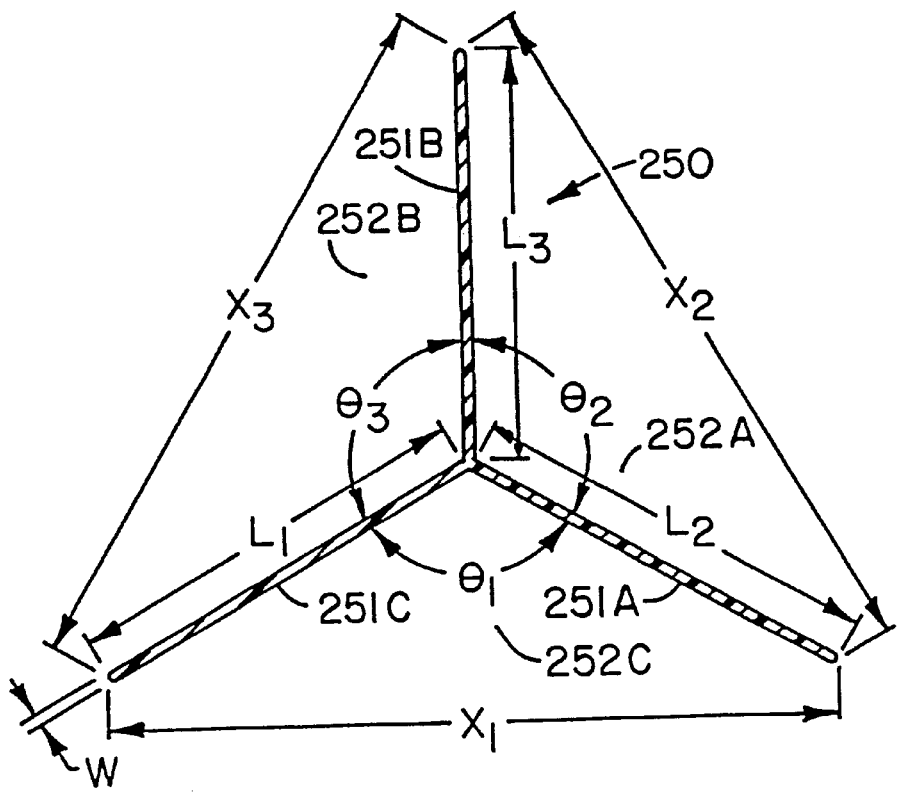
FIG. 23 is a schematic of a cross-section of a fiber having the generalized shape of fibers of example 6.

FIG. 23 shows the generalized cross-section 250 of the fiber cross-section of example 6.

The cross-section 250 shown in FIG. 23 includes the arms 251A, 251B, and 251C. The arms 251A and 251B define the channel 252A. The arms 251B and 251C define channel 252B. The arms 251C and 251A define the channel 252C. The width of the channels 252A, 252B, and 252C, are illustrated as $X_2$, $X_3$, and $X_1$, respectively. The length of the arms 251A, 251B, and 251C, are illustrated as $L_2$, $L_3$, $L_1$, respectively. The walls 251A and 251B define the angle $\theta_2$. The walls 251B and 251C define the angle $\theta_3$. The walls 251C and 251A define the angle $\theta_1$.

Preferred characteristics for the generalized cross-section 250 are that the angles $\theta_1$, $\theta_2$ and $\theta_3$ are between 110° and 130°, that the ratios for each of $L_1$, $L_2$, and $L_3$, to the width W are equal to or greater than 5, that at least one of the ratios of $L_2$ and $L_3$ to the width W is greater than 10, that the bulk factor is equal to or greater than 4, that the width W is less than or equal to 15 microns, more preferably less than 10 microns, and still more preferably less than 5 microns, and that the adhesion tension of the surface of the fiber with distilled water is equal to or greater than 25 dynes per centimeter.

Additional distinguishing characteristics of the fibers defined by the generalized cross-section 250 in FIG. 23 are that $X_1$ is greater than about 250 microns, and more preferably greater than about 300 microns, that $\theta_1$ and $\theta_2$ and $\theta_3$ are each approximately equal to 120°, and that the ratio of $L_2$ and $L_3$ is greater than about ½ and less than about 2.

Moreover, the fibers defined by the generalized cross-section 250 in FIG. 23 may have one or more protrusions along their length. Each such protrusion may be approximately W wide and no more than 3W long. Further, any such protrusions along the arms of the fiber should fit within a 10W wide corridor along the length of each arm, as shown in FIG. 25.

Figure 24:
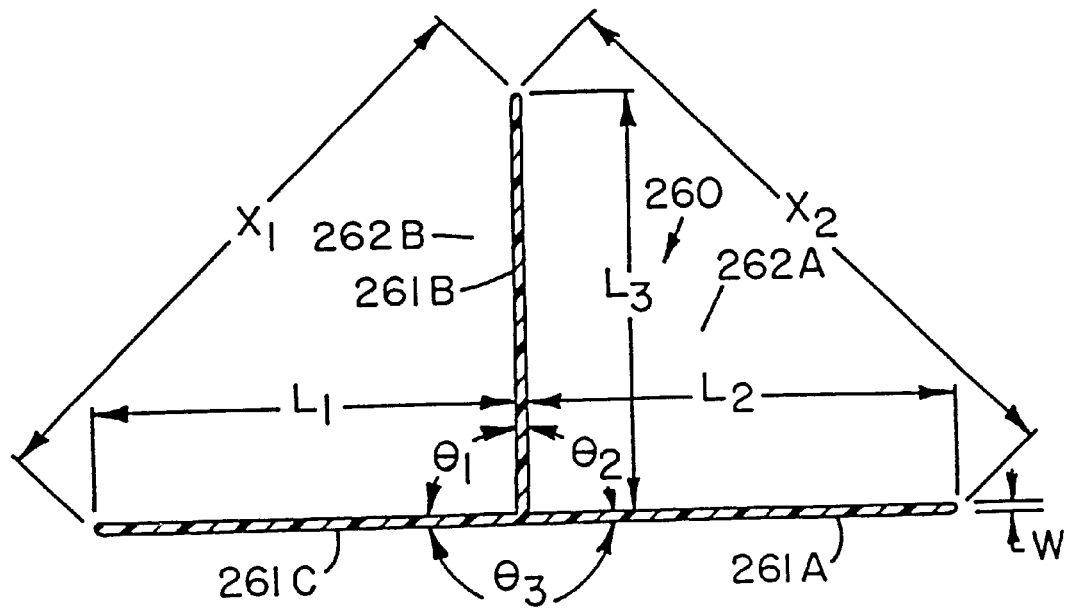
FIG. 24 is a schematic of a cross-section of a fiber having the generalized shape of fibers of example 8.

FIG. 24 shows a generalized version 260 of the cross-section of the fibers of example 8. The cross-section 260 includes the walls 261A, 261B, and 261C having the illustrated lengths $L_2$, $L_3$, and $L_1$, respectively. The walls 261A and 261B define the angle $\theta_2$. The walls 261B and 261C define the angle $\theta_1$. The walls 261C and 261A define the angle $\theta_3$. The walls 261A and 261B define the channel 262A. The walls 261B and 261C define the channel 262B.

For the generalized cross-section 260, preferably $\theta_1$ and $\theta_2$ are between 80° and 100°, and more preferably between 85° and 100°. Preferably $\theta_3$ is between about 170° and 200°. Preferably, the ratios of each of the lengths $L_1$, $L_2$, and $L_3$ to the width W are greater than or equal to 5, and more preferably at least one of these ratios is also greater than or equal to 10. Further, it is preferred that the bulk factor is greater than about 3.0, the width W is between about three and about 15 microns, and that the adhesion tension of the surface of the fibers with distilled water is greater than about 25 dynes per centimeter.

Additional distinguishing characteristics of the fibers defined by the generalized cross-section 260 are that $X_1$ and $X_2$ are both greater than about 250 microns, and more preferably greater than about 300 microns, that the lengths $L_1$, $L_2$, and $L_3$ are equal to one another, that the ratio of the length $L_1$ to $L_2$ is between about one half and about two, that the ratio of the length $L_3$ to $L_2$ is between about 0.02 and 10.

Moreover, the fibers defined by the generalized cross-section 260 may have one or more protrusions along their length. Each such protrusion may be approximately W wide and no more than 3W long. Further, the arms having the protrusions should fit within a 10W wide corridor, as shown in FIG. 25. FIG. 25 shows the generalized fiber cross-section 270 and the 10W wide corridors 271A, 271B and 271C. The cross-section 270 includes the arms 272A, 272B, and 272C. Further, the arms 272B and 272C have protrusions 273. Each of the arms 270A, 272B, and 272C is delimited by a 10W wide corridor, where W is the width of each of the arms.

FIG. 25 shows each arm of a fiber including its protrusions fitting within a 10W wide corridor as required by the criteria for the generalized cross-section discussed hereinabove. All three of the arms shown in FIG. 25 fit within the 10W width criteria.

FIGS. 26A–B illustrate the definition of the single fiber bulk factor.

FIG. 26A shows the fiber cross-section 280 which is used to define the procedure for determining the single fiber bulk factor. The single fiber bulk factor is defined as the cross-sectional area of the channels divided by the cross-sectional area of the fiber.

The fiber cross-section 280 has the width W and includes the arms 282A, 282B, and 282C, which have the distal tips 283A, 283B, and 283C. The arms 282A, 282B, and 282C define the cross-sectional channel areas 281A, 281B, and 281C. The cross-sectional channel areas 281A, 281B, and 281C are defined by the straight line segments tangent to the distal tips of the arms and the surfaces of the arms.

A determination, in arbitrary units, of the cross-sectional area of the channels provides an area of 225, and a determination of the cross-sectional area of the fiber in the cross-section 280 provides an area of 60. Therefore, the single fiber bulk factor for the cross-section 280 is 225/60= 3.8.

FIG. 26B shows the fiber cross-section 290 and the cross-sectional area of the channel 291 in hashing. Determination, in arbitrary units, of the area of the cross-section of the channels 291 and the area of the cross-section 290 of the fiber provides 225 and 44 in arbitrary units. Therefore, the single fiber bulk factor for FIG. 26B is 5.1.

Figure 30A:
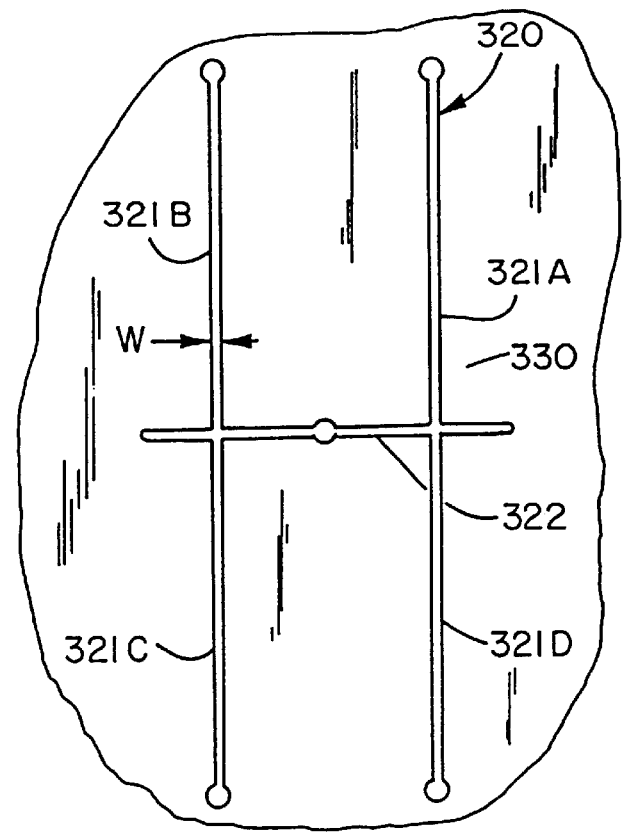
FIG. 30A is a schematic showing the dimensions of an aperture of a spinnerette used in comparative example 12.

FIG. 30A shows the dimensions of the aperture 320 of the spinnerette 330 used in comparative example 12. The aperture 320 includes the arms 321A, 321B, 321C, 321D, and the base 322. FIG. 30A illustrates the relative dimensions in which the arms 321A are fifty times the width W of the aperture and the base 322 is forty times the width W of the aperture. The width W is 0.100 millimeters in the aperture 320. The aperture was cut using a conventional YAG laser machining system. The machining of the apertures of the spinnerettes disclosed herein can be accomplished using conventional laser machining systems.

Figure 30B:
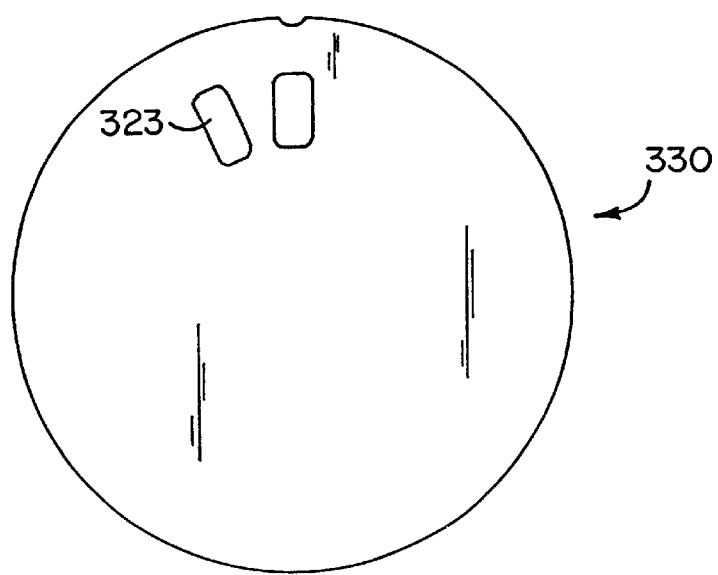
FIG. 30B is a schematic illustrating a face of the spinnerette used in comparative example 12 showing an arrangement of bores and apertures.

FIG. 30B schematically illustrates the spinnerette 330 used in comparative example 12 showing the placement of bores 323 spaced at 22.50 from one another in a circular pattern in the spinnerette 330.

Figure 31:
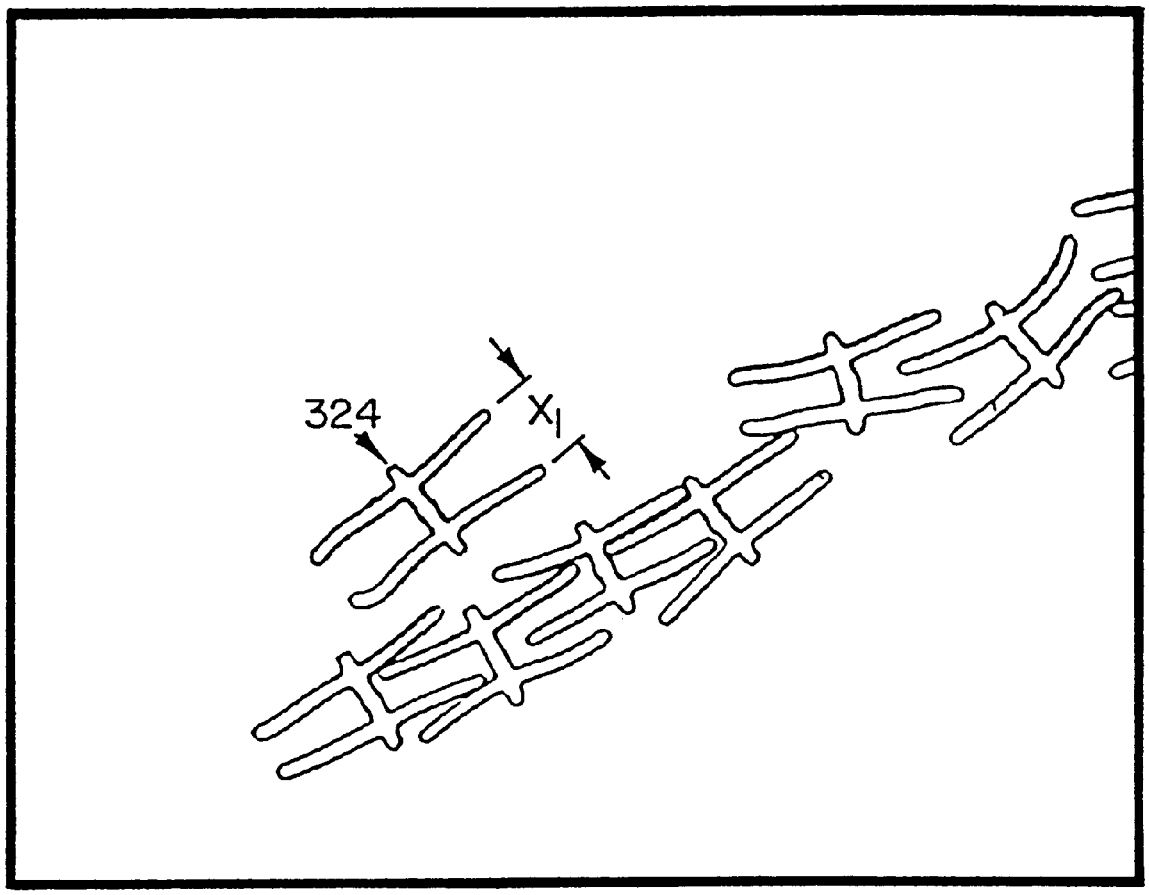
FIG. 31 is a photocopy of a photograph at a magnification of about 270 of a cross-section of comparative example 12.

FIG. 31 shows magnified views of cross-sections 324 of fibers of comparative example 12.

FIG. 32A is a side sectional view of a bore 331 having a blank thickness 331A that is 0.050 inch of the spinnerette 340 used in comparative example 13.

FIG. 32B shows an aperture 332 of the bore 331 of the spinnerette 340 used in comparative example 13.

FIG. 32C is a magnified view of the aperture 332 showing the-relative dimensions of the aperture 332. The aperture 332 has a width W, and the lengths 333, 334, 335, 336, 337, and 338 which are respectively 67W, 33.5W, 134W, 67W, 38.5W, and 77W. The width W is 0.084 millimeters in the aperture 332.

FIG. 32D shows the spinnerette 340 including the arrangement of the bores 331. The thirty-seven bores 331 are arranged in seven rows.

Figure 33:
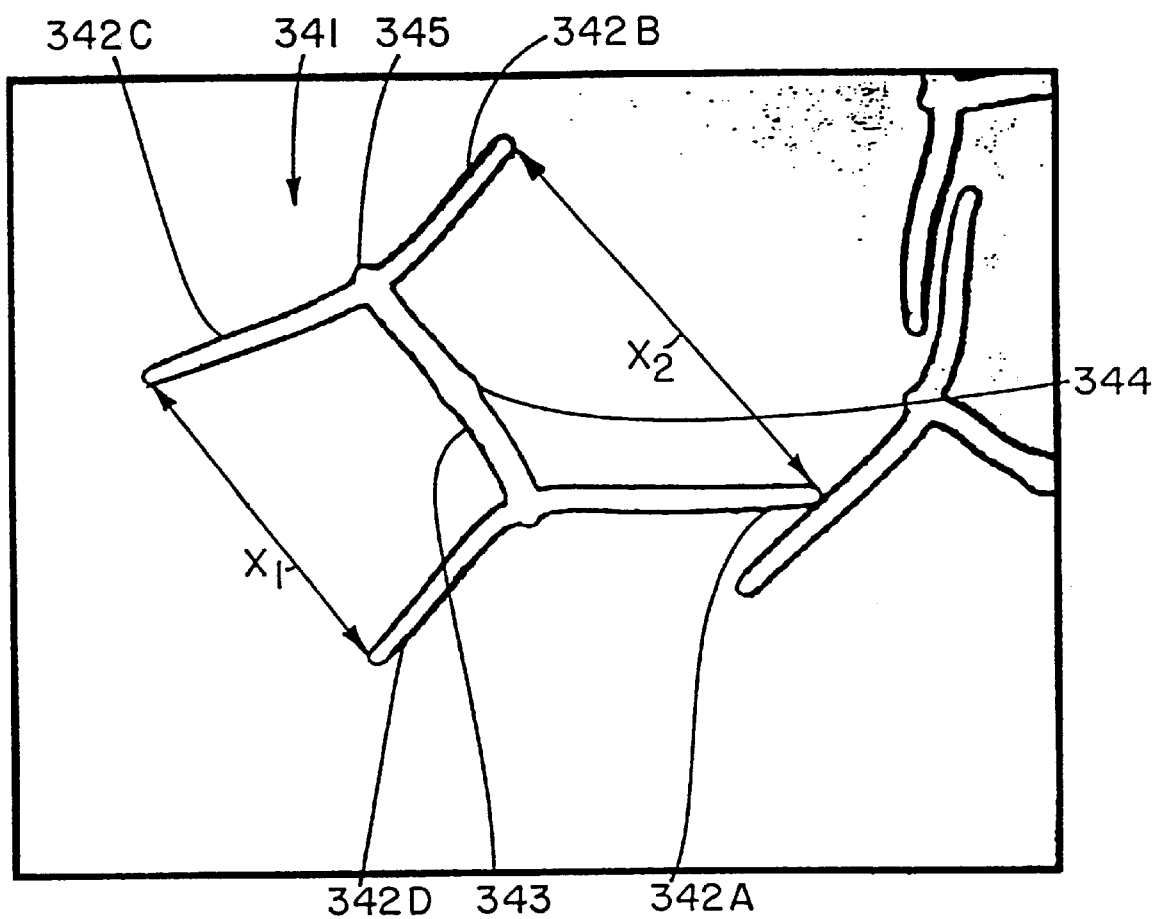
FIG. 33 is a photocopy of a photograph at a magnification of about 420 of a cross-section of a fiber of example 13.

FIG. 33 shows a cross-section 341 of a fiber of comparative example 13. The cross-section 341 includes the arms 342A, 342B, 342C, and 342D, and the base 343. There are small projections 344 projecting from the center of the base 343. There are projections 345 projecting away from the base 344 and away from the surface of the walls. The cross-section 341 is generally "H" shaped and defines two channels.

Figure 34:
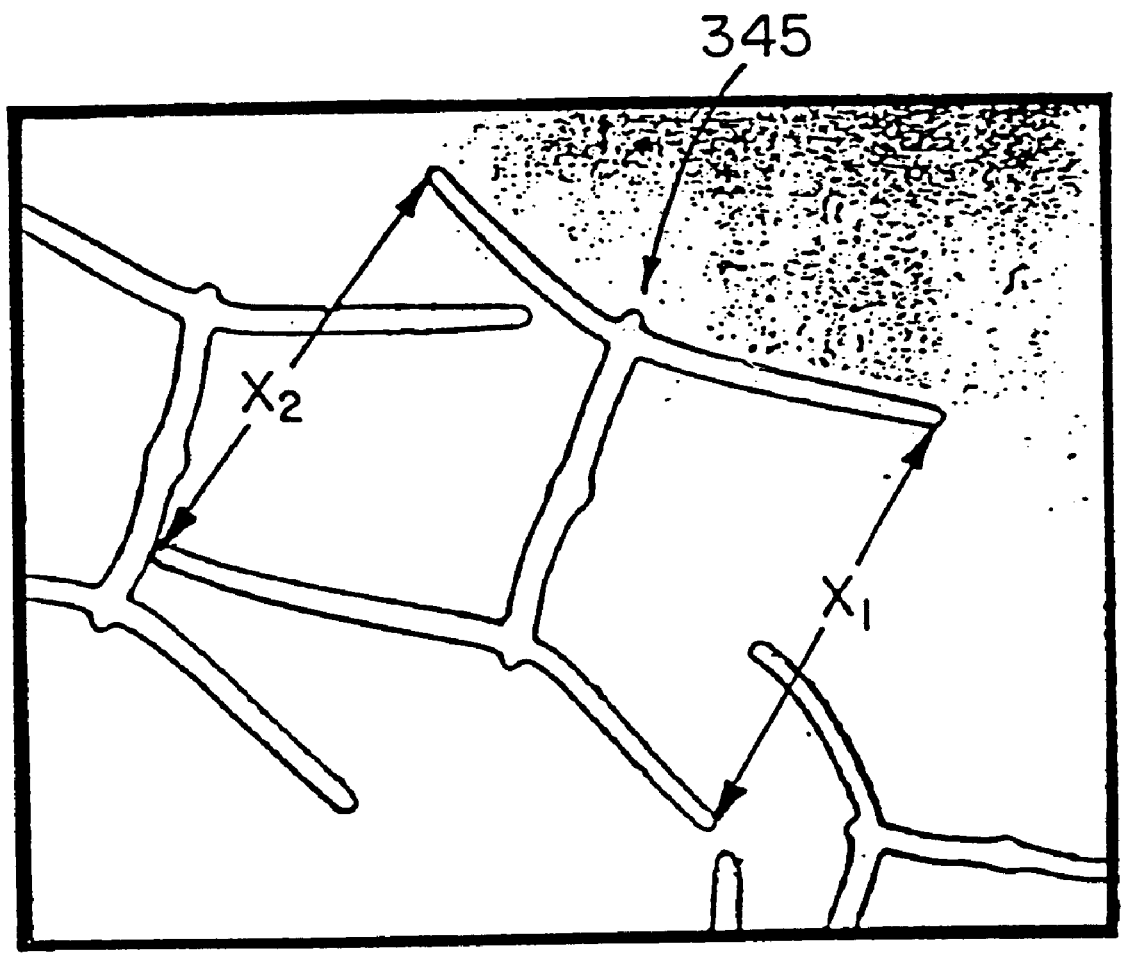
FIG. 34 is a photocopy of a photograph of a cross-section at a magnification of about 330 of a cross-section of a fiber of example 14.

FIG. 34 shows a cross-section 345 of a fiber of comparative example 14. The shape of the cross-section 345 of comparative example 14 is similar to the shape of the cross-section 341 of comparative example 13.

FIGS. 35–37C show cross sections used in defining the procedure for determining the capillary channel area for flow for a single fiber. The capillary channel area for flow is an approximation, based upon the forces on the liquid and the geometry of the fibers, of the cross-sectional area along which the liquid flows. Capillary channels on the surfaces of fibers are those channels where capillary forces are large compared to gravity.

Channel width dimensions less than about 250 microns are required for capillary forces to be large compared to gravity. There are basically two types of cross-sectional geometries of channels, which are substantially parallel walled channels and substantially "V" shaped channels.

Figure 35:
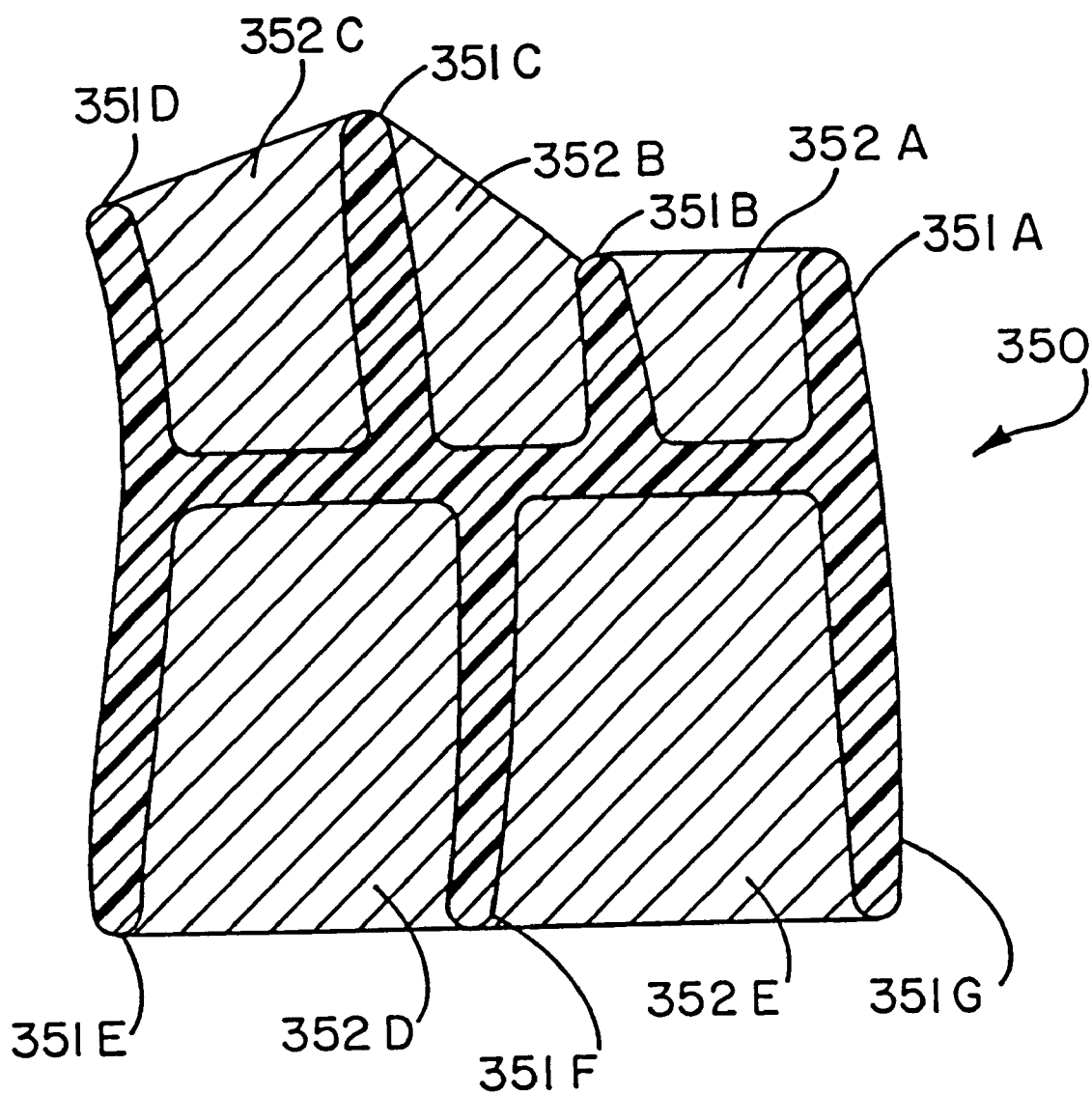
FIG. 35 is a schematic of a cross-section of a fiber used for illustrating the determination of capillary channel area for flow for cross-sections having channels having essentially parallel channel walls separated by less than 150 microns.

For all channels that have a channel width at the mouth of the channel of less than 150 microns, a straight line is drawn that closes the mouth of the channel. The enclosed channel area is defined as the capillary channel area for flow. FIGS. 35 and 37A illustrate capillary channel area for flow for fibers the widths of the channels of which are less than 150 microns. FIGS. 36A–C, 37B, and 37C illustrate the capillary channel area for flow for various shaped channels that are wider than 150 microns. The general principles relating to FIGS. 35–37C can be used to define the capillary channel area for flow for any channel's cross-section. In general, all surfaces of the cross-section that define an angle of less than or equal to 120° and that can be closed by 150 micron long line segments are closed, and the sum of the area of the closed section is defined as the capillary channel area for flow. Exclusion of areas having surfaces that define an angle of greater than 120° excludes shallow regions that do not define channels deep enough to substantially affect the transport of a liquid along the fiber.

FIG. 35 shows a cross-section 350 of a fiber that includes arms 351A–351G and a base (unnumbered). The arms 351A–351G form channels 352A–352E. The two arms defining each one of the channels 352A–352E are less than 150 microns apart from one another. The capillary channel area for flow for the fiber having the cross-section 350 is indicated by the hashed regions of the channels 352A–352E. The capillary channel area for flow is the area bounded by the walls of the channels and a straight line segment connecting the distal tips of the walls of the channels.

Figure 36A:
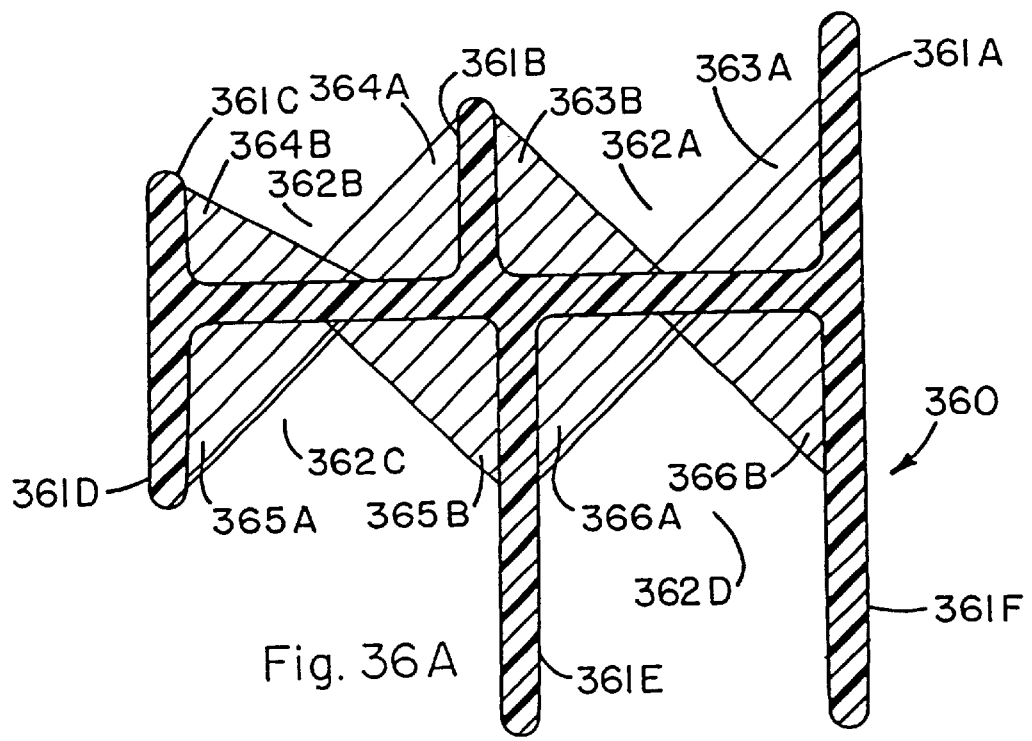
FIG. 36A is a schematic of a cross-section of a fiber useful for illustrating the determination of capillary channel area for flow for fiber cross-sections having walls defining channels separated by greater than 150 microns.
Figure 37A:
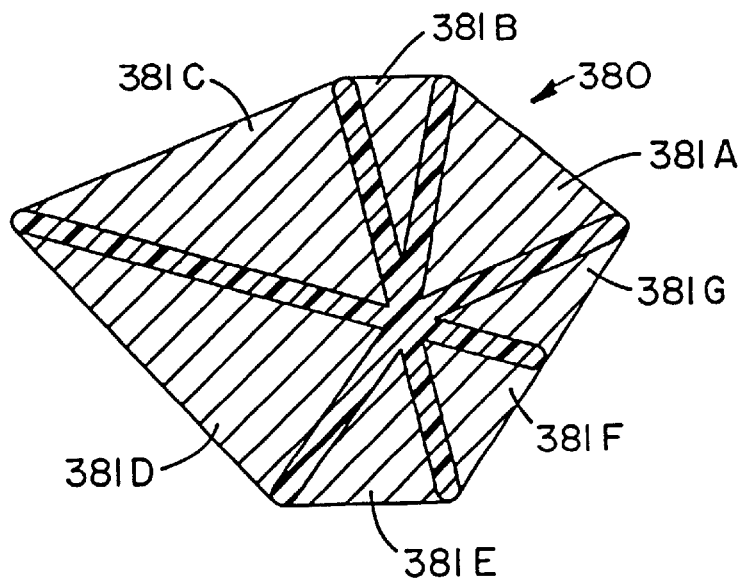
FIG. 37A is a schematic of a cross-section of a fiber useful for illustrating the determination of the capillary channel area for flow for "V" shaped channels whose channel walls define an angle of less than 120° and have widths at the mouths of less than 150 microns.

FIG. 36A shows a cross-section 360 of a fiber having arms 361A–361F that define channels 362A–362D. The widths of the channels 362A–362D are greater than 150 microns. The hashed regions 363A and 363B define the capillary channel area for flow of the channel 362A. The hashed regions 364A and 364B define the capillary channel area for flow of the channel 362B. The hashed regions 365A and 365B define the capillary channel area for flow of the channel 362C. The hashed regions 366A and 366B define the capillary channel area for flow of the channel 362D. The hashed regions in FIG. 36A indicating the capillary channel area for flow in each of the channels are defined by a 150 micron long line segment positioned (1) so that the ends of the line segment contact the surface of the fiber and (2) so that the line segment is perpendicular to a bisector of the angle between the arms and the base that define the channel. The capillary channel areas for flow shown in FIG. 36A are defined by the one hundred fifty micron long line segments and the surface of the arm and the surface of the base.

Figure 36B:
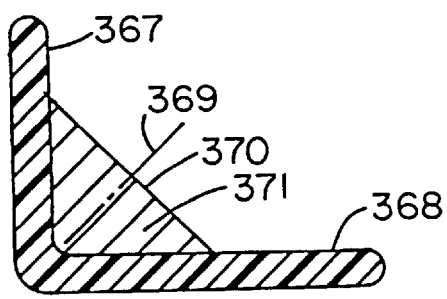
FIG. 36B is a schematic of a cross-section of a fiber useful for flow for illustrating determination of capillary channel area for flow for large channels.

FIG. 36B shows an arm section 367 of a cross-section of a fiber and an arm section 368 of the cross-section of the fiber. The arm sections 367 and 368 form a right angle. FIG. 36B illustrates a bisector 369 of the right angle and a 150 micron long line segment 370. The 150 micron long line segment 370 is positioned in accordance with the procedure for defining capillary channel area for flow so that the line segment is perpendicular to the bisector 369. The area 371 between the arm sections 367, 368, and the line segment 370 is the capillary channel area for flow for the portion of the cross-section of the fiber shown in FIG. 36B.

Figure 36C:
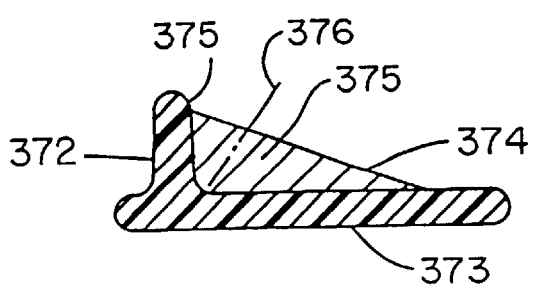
FIG. 36C is a schematic of a cross-section of a fiber useful for illustrating determination of capillary channel area for flow for large channels having a long wall and a short wall.

FIG. 36C shows a portion of a cross-section of a fiber which includes a short arm section 372 the length of which is 50 microns and a long arm section 373 the length of which is greater than 150 microns. FIG. 36C shows a 150 micron long line segment 374 one end of which is in contact with the distal tip 375 of the short arm section 372 and the other end of which in contact with the long arm section 373 to define a capillary channel area for flow 375. The line segment 374 is not perpendicular to the bisector 376. When one section of the fiber defining a wall of a channel is so short that it would not contact a 150 micron line that is perpendicular to the bisector of the angle between the wall and the base of the channel, the procedure for determining capillary channel area for flow places one end of the 150 micron long line segment at the distal tip of the short channel wall and the other end of the line segment along the opposing wall of the channel.

FIG. 37A shows a cross-section 380 of a fiber having "V" shaped channels in which the walls of the channels define an angle less than 120° and the widths at the mouths of the channels are less than 150 microns. The capillary channel areas for flow 381A–381G are each defined by the area between two opposing arms of the cross-section 380 that form walls of a channel and a line segment contacting the distal tips of the two arms. In each case, the line segment is less than 150 microns long.

Figure 37B:
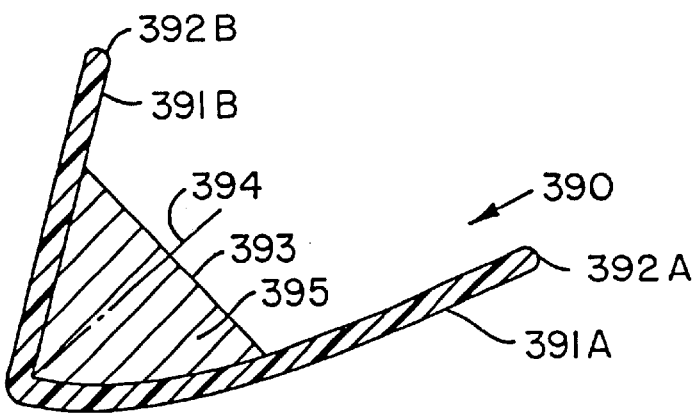
FIG. 37B is a schematic of a cross-section of a fiber useful for illustrating the determination of capillary channel area for flow for channels whose walls define an angle of less than 120° and which have a width at the mouth of greater than 150 microns.

FIG. 37B shows a cross-section 390 of a fiber forming a "V" shaped channel and which includes arms 391A and 391B. The distal tips 392A and 392B of the arms 391A and 391B are greater than 150 microns apart. FIG. 37B shows the 150 micron long line segment 393 which is perpendicular to the bisector 394 of the angle defined by the arms 391A and 391B. The line segment is positioned so that its ends contact the walls of the channel. The capillary channel area for flow 395 is defined by the 150 micron long line segment 393 and the arms 391A and 391B.

Figure 37C:
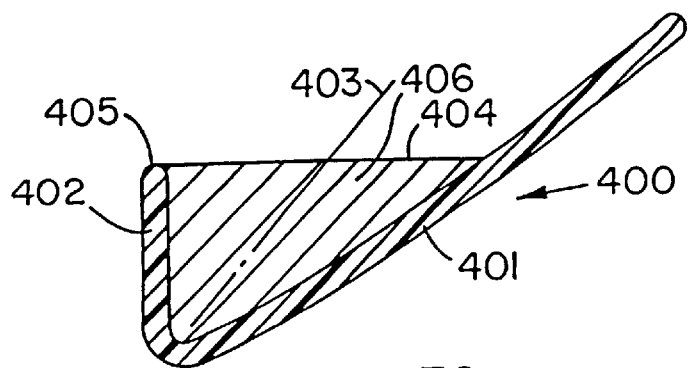
FIG. 37C is a schematic of a cross-section of a fiber useful in illustrating the determination of capillary channel area for flow for channels whose walls define an angle of less than 120°, which have a width at the mouth greater than 150 microns, and which have one channel wall shorter than the other channel wall.

FIG. 37C shows a cross-section 400 of a fiber forming a distorted "V" shape that includes the long arm 401 and the short arm 402. FIG. 37C shows the bisector 403 of the angle defined by the arms 401 and 402. A 150 micron long line segment perpendicular to the bisector 403 would not have ends contacting the short arm of 402 and the long arm 401. The 150 micron long line segment 404 is positioned so that one of its ends contacts the distal tip 405 of the short arm 402 and the other end contacts the long arm 401. The capillary channel area for flow 406 is defined by the line segment 404, the short arm 402, and the portion of the long arm 401 that connects the short arm and the point of contact at segment 404.

Figure 38A:
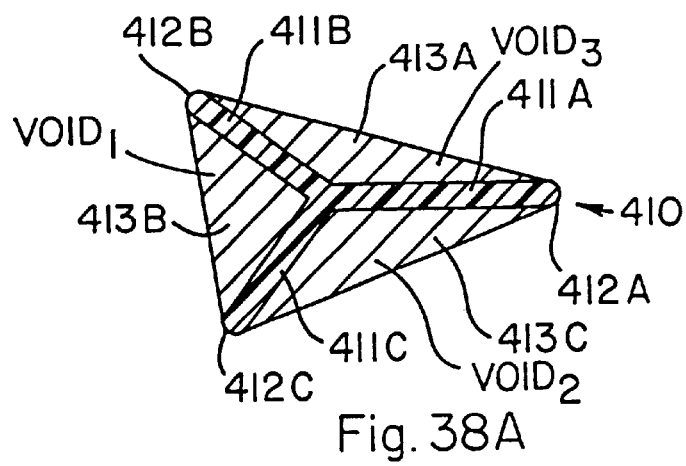
FIG. 38A is a schematic of a cross-section of a fiber useful in illustrating the determination of single fiber bulk factor.
Figure 38B:
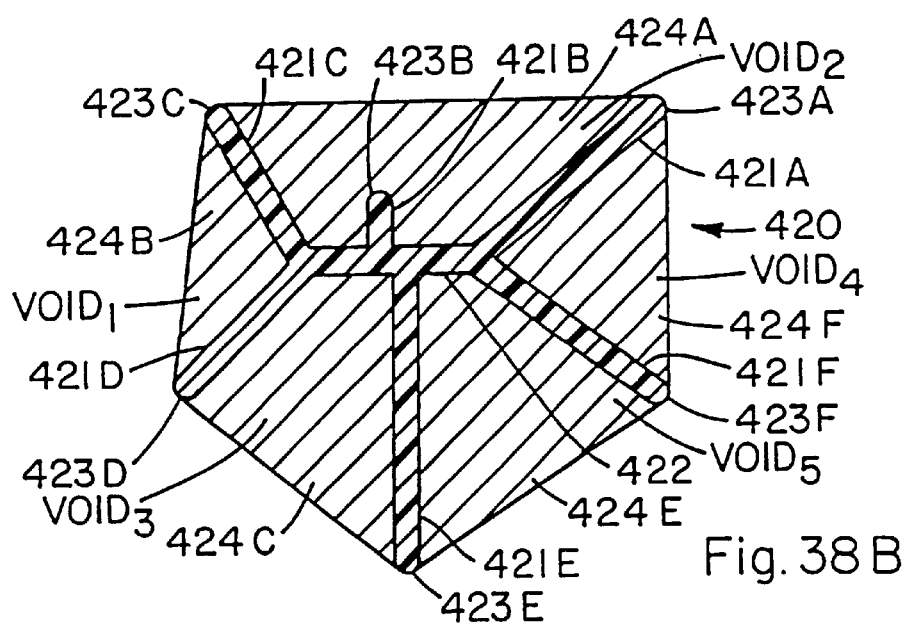
FIG. 38B is a schematic of a cross-section of a fiber useful in illustrating the determination of single fiber bulk factor.

FIGS. 38A and 38B show cross-sections illustrating the procedure for defining the single fiber bulk factor (bulk factor). The bulk factor is defined by the sum of the cross-sectional areas of the voids divided by the cross-sectional area of the fiber.

FIG. 38A shows a cross-section 410 of a fiber having arms 411A, 411B, and 411C. The arms 411A, 411B, and 411C have distal tips 412A, 412B, and 412C. The area defined by straight line segments between the distal tips 412A, 412B, and 412C and the arms 411A, 411B, and 411C defines the void cross-sectional areas 413A, 413B, and 413C. For the cross-section shown in FIG. 38A, the bulk factor equals the sum of the void areas (413A plus 413B plus 413C) divided by the area of the fiber's cross-section 410.

FIG. 38B shows a cross-section 420 including the arms 421A–421F and the base 422. The arms 421A–421F have distal tips 423A–423F. The area defined by a line that contacts the distal tips of two of the arms and does not contact any other portion of the cross-section 420 defines the void areas 424A–C, 424E, 424F. The bulk factor of the cross-section 420 is the sum of the void areas (of 424A plus 424B plus 424C plus 424E plus 424F) divided by the area of-the cross-section 420 of the fiber. For the cross-section 420 shown in FIG. 38B, the bulk factor=[(Void$_1$+Void$_2$+Void$_3$+Void$_4$+Void$_5$)/(Dark Area)] where the terms Void$_1$, Void$_2$, Void$_3$, Void$_4$, and Void$_5$ are illustrated in FIG. 38B. Note that the arm 421B shown in FIG. 38B does not define separate void areas on either side of it because a line tangent to the distal tip 423B and tangent to the distal tip of either of the adjacent arms 423A or 423C would also contact additional regions of the cross-section 420.

Figure 39:
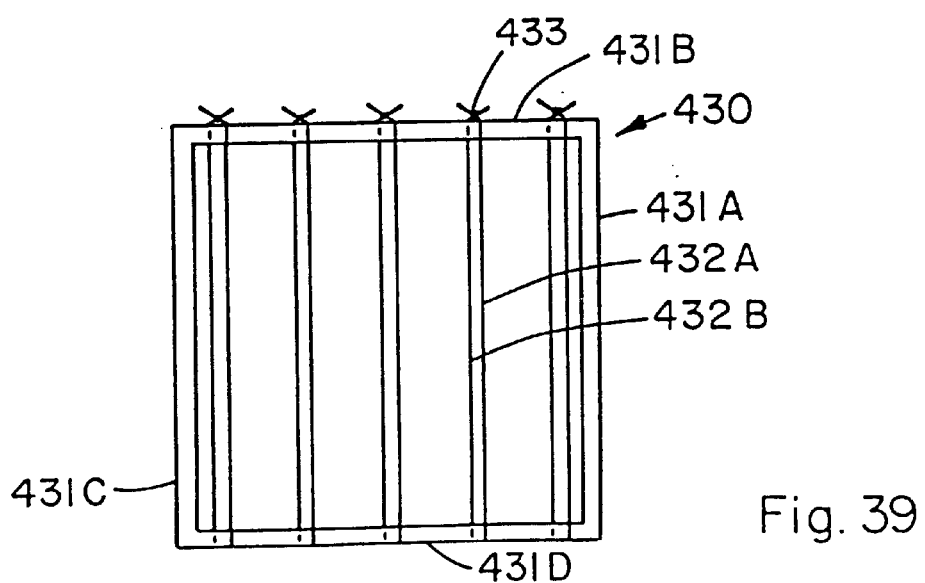
FIG. 39 is a schematic illustrating a metal/plastic harp having loops of fibers tied there around that is useful in illustrating the determination of vertical rise.

FIG. 39 shows a metal or plastic harp 430 defined by rims 431A–431D. A fiber having a portion 432A on the front side of the harp and a portion 432B on the back side of the harp is wrapped around the harp and knotted at the knot 433 at the top of the harp. Additional fibers (unnumbered) are wrapped around the harp as illustrated in FIG. 39. The length of the harp between the rims 431B and 431D is illustrated as 25 centimeters in FIG. 39. Instead of the single fiber 432A, 432B, one or more bundles of fibers could be wrapped around the harp. The same vertical rise test procedure applies to single fibers and bundles of fibers. The bundle of fibers that is used is typically the total number of fibers in the strand of yarn, as the yarn was produced. This may vary from 3 to 100 or more.

The vertical rise test procedure involves taking individual fibers or strands and tying multiple closed loops of the fibers or strands around the metal/plastic harp 430 as shown in FIG. 39.

With the laboratory at approximately 70° F. (21.1° C.) and 65% relative humidity, the harp is placed in a beaker containing Syltint® Red or Red Test Solution. The height up the harp to which the liquid moves above the liquid level in the beaker after 15 minutes is recorded to the nearest 0.1 cm. Sixteen strands or fibers are typically wound on the harp and the average height of the rise of the liquid for the sixteen strands is determined.

Liquid Acquisition/Distribution Structures

FIGS. 40A–B, 41A–C, 43A–B, 44, and 47–50 show the liquid acquisition/distribution and absorbent product structures of the invention.

FIG. 40A shows a liquid acquisition/distribution structure 440 having a top layer 441, a liquid distribution structure 442, and a flow resistance layer 443.

FIG. 40B pictorially shows the distribution of the liquid 446 due to a liquid insult 444 insulting the absorbent product 445. The liquid 446 of the insult 444 traverses the top layer 441 and contacts the liquid distribution structure 442. The liquid distribution structure 442 distributes the liquid 446 parallel to the top layer 441, and communicates the liquid to the absorbent core 447 at a plurality of distinct locations 448A–448I via lower liquid resistance regions. The absorbent product 445 has the back layer 449.

Figure 41A:
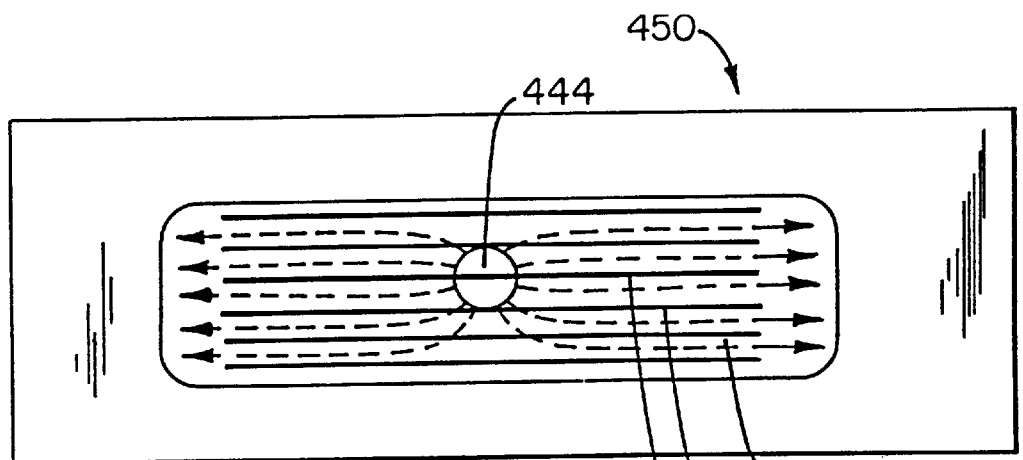
FIGS. 41A–C are top views of various alternative embodiments of the basic liquid acquisition/distribution structures of FIGS. 40A–40B showing different liquid distribution structures.

FIG. 41A is a top view of a liquid acquisition/distribution structure 450 of the present invention showing the insult 444 and the fibers 445A, 445B, and 445C of the liquid distribution structure. The fibers 445A, 445B, and 445C are aligned in the same direction in order to transport the liquid from the insult 444 along the axis of the bundles of the fibers, as illustrated by the arrows in FIG. 41A.

Figure 41B:
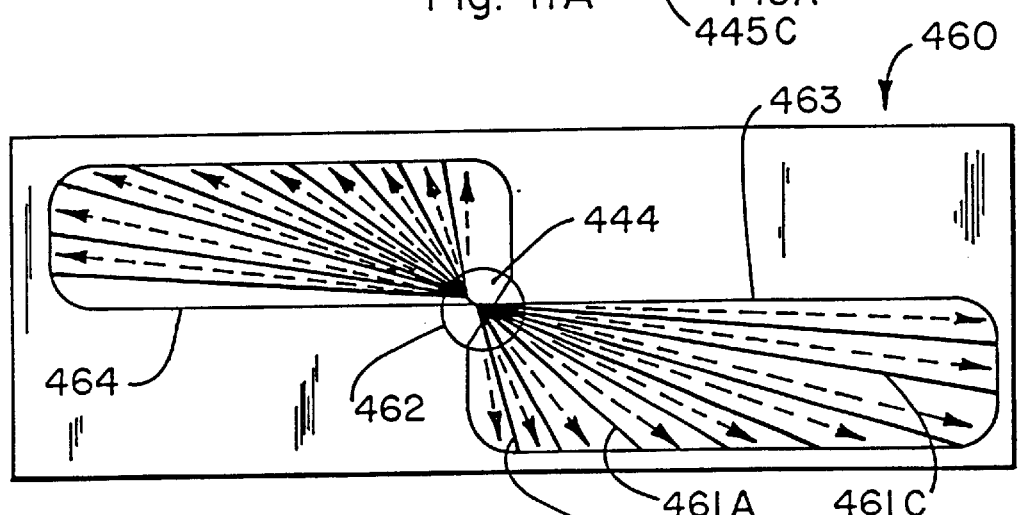

FIG. 41B shows a liquid acquisition/distribution structure 460 in which the fibers 461A, 461B, and 461C fan out from the region 462 of the liquid insult 444 in order to distribute the liquid from the insult 444 along the fanned out regions 463 and 464.

Figure 41C:
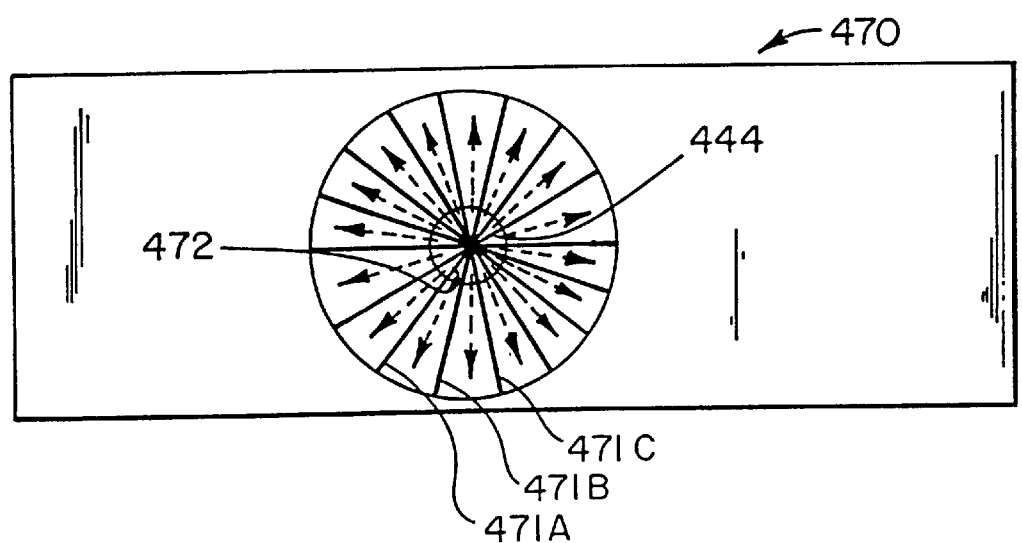

FIG. 41C shows the liquid acquisition/distribution structure 470 in which the fibers 471A, 471B, and 471C fan out from the region 472 where the liquid insult 444 occurs. The fibers of the liquid acquisition/distribution structure 470 extend radially in a circular pattern from the region 472 in order to distribute the liquid radially outward in all directions.

Figure 42:
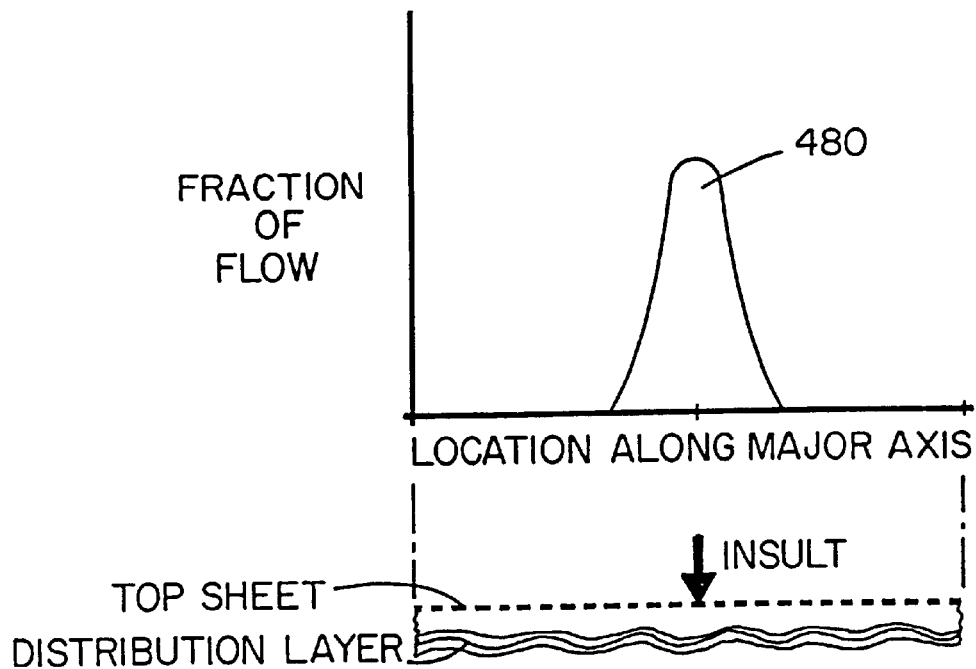
FIGS. 42A–D are graphical representations of the distribution of liquid flow into various layers of the absorbent product of the invention.
Figure 42:
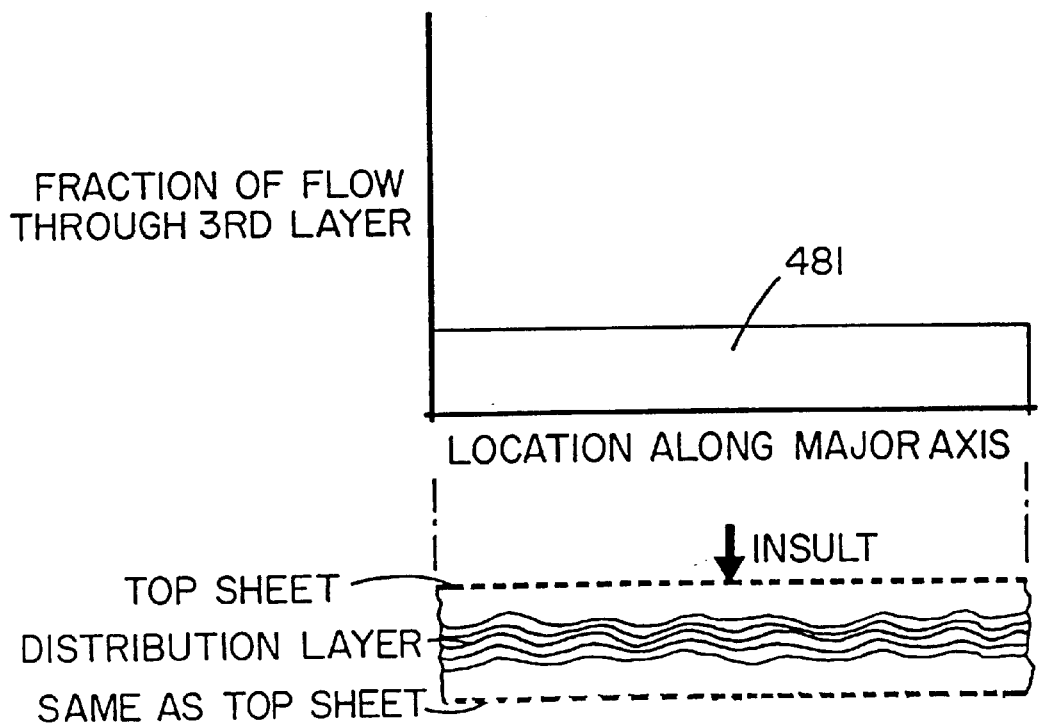
Figure 42:
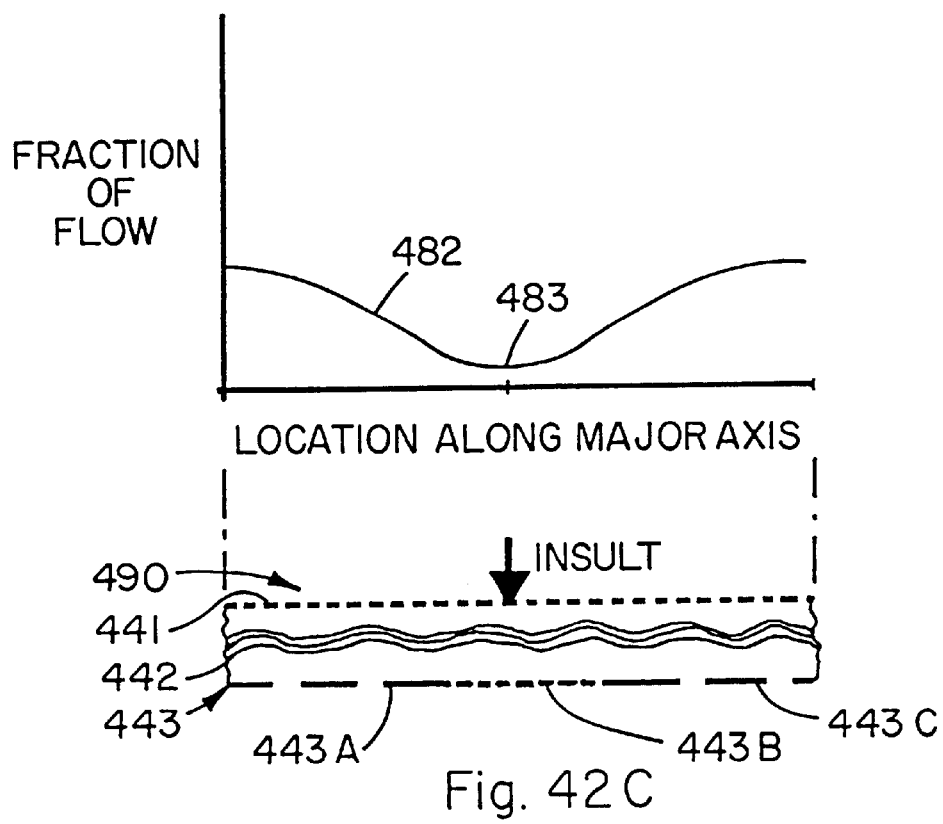
Figure 42:
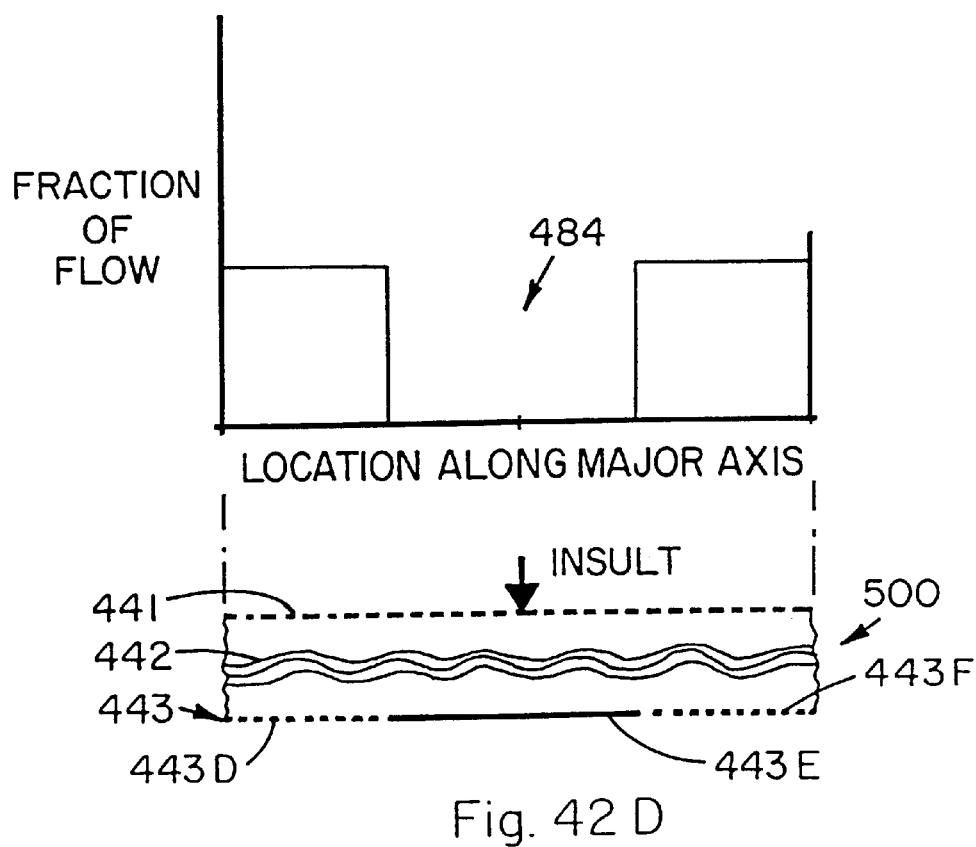

FIG. 42A includes a graph showing fractions of the flow versus the location of the flow along the major axis of an absorbent product and a schematic of the acquisition/distribution structure illustrating the location of the insult in the top layer. FIG. 42A shows that the distribution 480 of the liquid along the top layer is distributed close to the location of the insult on the top sheet.

FIG. 42B includes a graph showing the uniform distribution of the liquid along the major axis of the absorbent product through the liquid flow resistance layer (which is the third layer of the liquid acquisition/distribution structure). FIG. 42B shows that the liquid acquisition/distribution structure functions to spread out the initial liquid distribution 480 to the distribution 481.

FIG. 42C includes a graph showing the distribution of the liquid through the liquid resistance layer 443 along the major axis of the absorbent product for an alternative liquid acquisition/distribution structure 490. The acquisition/distribution structure 490 includes a top layer 441, a distribution layer 442, and an inhomogeneous liquid flow resistance layer 443. The inhomogeneous resistance layer 443 includes the low resistance areas 443A and 443C, and the high resistance area 443B. The high resistance area 443B provides more resistance to the flow of liquid across that area of the liquid resistance layer 443 than the low resistance areas 443A and 443C. The presence of the high resistance area 443 reduces the flow through the high resistance area 443 relative to the low resistance areas 443A and 443C resulting in the depression 483 of the distribution 482 in the region of the high resistance area 443B.

FIG. 42D includes a graph showing the distribution of the liquid through the liquid flow resistance layer 443 versus the location along the major axis of the absorbent product for the alternative liquid acquisition/distribution structure 500. The liquid acquisition/distribution structure 500 includes the permeable areas 443D and 443F and the impermeable area 443E. The impermeable area 443E prevents any transmission of the liquid resulting in the zero fraction of flow through the high resistance layer 443 in the region of the impermeable area 443E shown in the distribution area 484.

FIG. 43A shows an absorbent product 510 comprising the liquid acquisition/distribution structure 511, and the absorbent core 512. FIG. 43A illustrates with arrow heads where the transmission of liquid from the liquid acquisition/distribution structure 511 to the absorbent core 512 occurs. Along the periphery of the absorbent core 512 in the regions 514, 515, the liquid is communicated directly to the absorbent core 512 after having been diverted by the high resistance layer 517. The resistance layer 517 substantially or completely prevents the liquid from going through the resistance layer 517.

FIG. 43B shows an absorbent product 520 including a liquid acquisition/distribution structure 521 and an absorbent core 522 in which the high resistance layer 523 of the liquid acquisition/distribution structure 521 separates the absorbent core 522 from the liquid distribution layer 524 throughout the absorbent product.

FIG. 44A shows a top plan view of an absorbent product 520 indicating a region 521 in the absorbent product that contains the liquid acquisition/distribution structure 523 shown in FIG. 44B.

FIG. 44B shows the liquid acquisition/distribution structure 523 including the top layer 524, the liquid distribution structure or layer 525 and the liquid resistance layer 526.

The liquid distribution structure or layer 525 consists of a plurality of aligned fibers spread out in the form of a layer. The width 527 of the distribution layer 525 depends upon the desired absorbent product and the intended insult. Typically, the width 527 of the distribution layer 525 in the region where the insult is intended will be at least as wide as the intended insult, which is typically between about 2 and 10 centimeters.

Figure 45B:
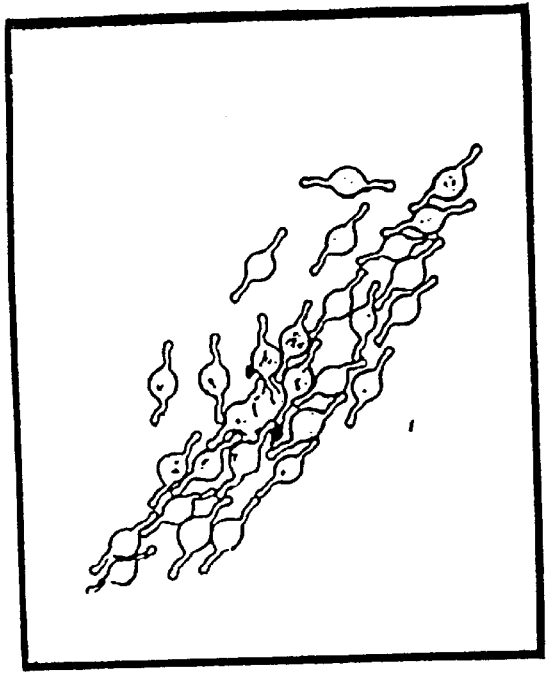
FIG. 45B is a photocopy of a photograph of a magnified cross-section of a fiber bundle of example 18.
Figure 45D:
FIG. 45D is a photocopy of a photograph of a magnified cross-section of a fiber bundle of example 20.
Figure 45A:
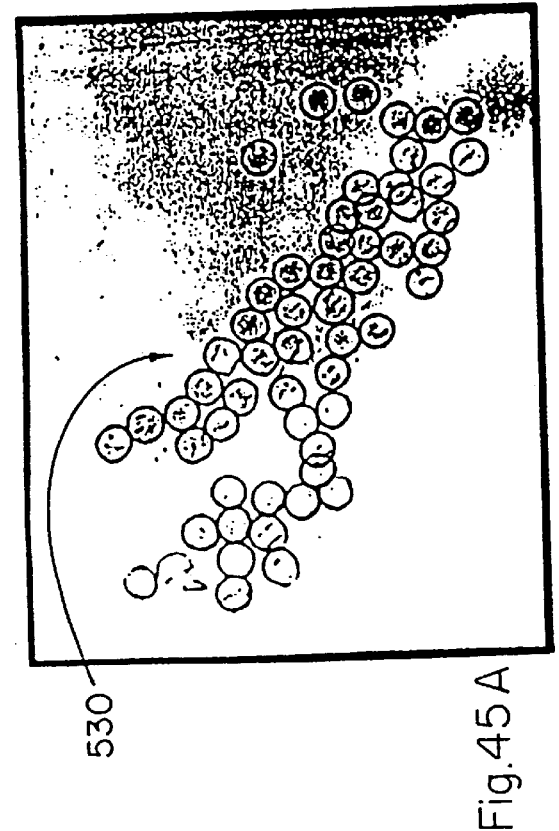
FIG. 45A is a photocopy of a photograph of a magnified cross-section of a fiber bundle of example 15.

FIG. 45A is a photocopy of a photograph of a magnified cross-section of the bundle 530 of the fibers used in the distribution structure in example 15. Those fibers have round cross-sections. These fibers are not the preferred fibers.

FIG. 45B shows a distribution of the cross-sections of fibers used in the distribution structure in example 18.

Figure 45C:
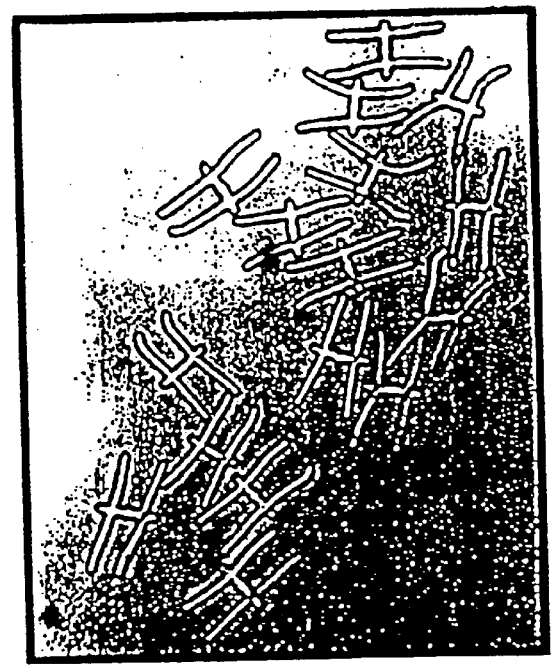
FIG. 45C is a photocopy of a photograph of a magnified cross-section of a fiber bundle of example 19.

FIG. 45C shows the cross-section of a bundle of the fibers used in the distribution structure in example 20.

FIG. 45D shows the cross-section of a bundle of the fibers used in the distribution structure in example 19.

Figure 46:
FIG. 46A is a photocopy of a photograph of a magnified cross-section of a fiber bundle of example 21.
FIG. 46B is a photocopy of a photograph of a magnified cross-section of a fiber bundle of example 22.
Figure 46:
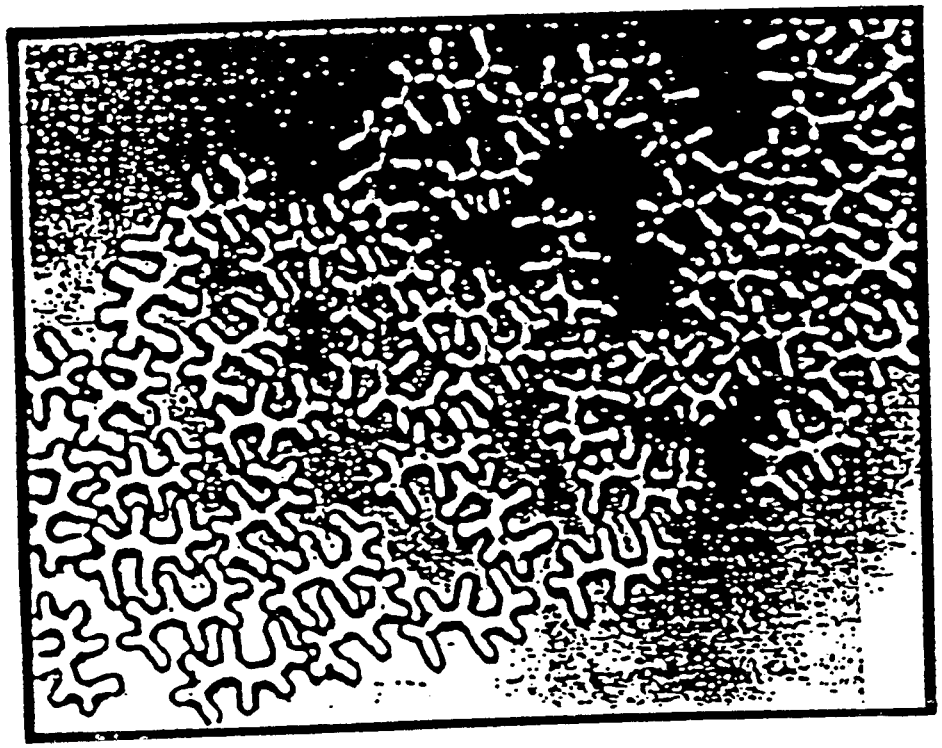
Figure 47:
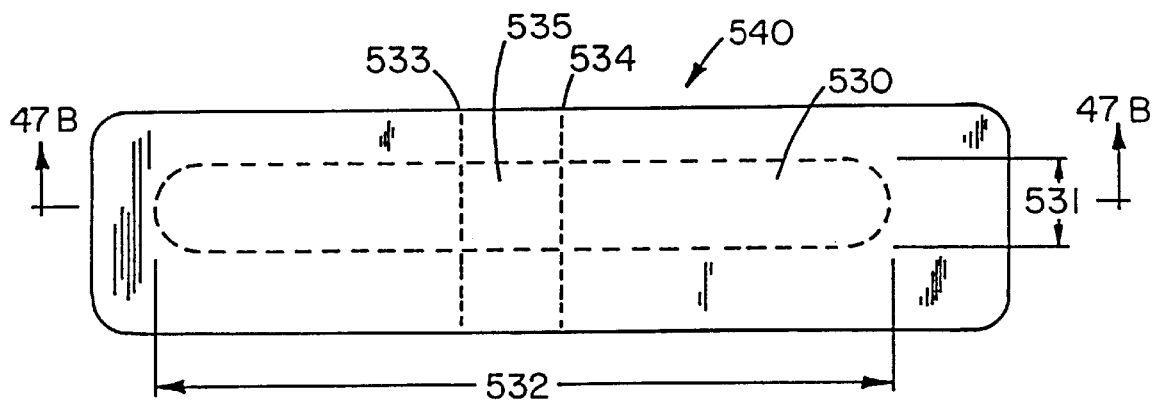
FIG. 47A is a top plan of a liquid acquisition/distribution structure used in example 28.
FIG. 47B is a side sectional view of a liquid acquisition/distribution structure used in example 28.
Figure 47:
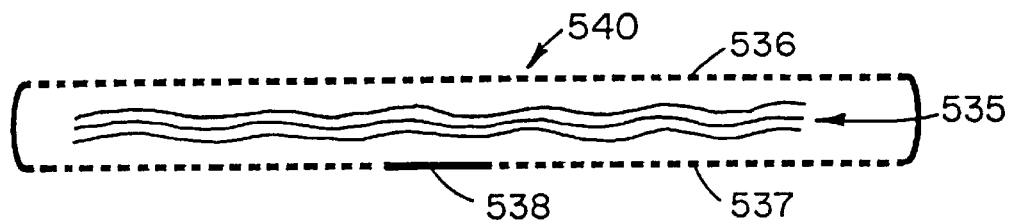

FIG. 46A shows a cross-section of a bundle of the fibers used in the distribution structure in example 21.

FIG. 46B shows a cross-section of a bundle of the fibers used in the distribution structure in example 22.

FIG. 47A shows a top plan view of an acquisition/distribution structure used in example 28 which includes the region 530 included in the distribution layer. The region 530 has a width 531 of 2 centimeters and a length 532 of 16 centimeters. Further, dashed lines 533 and 534 indicate the length of a 4 centimeter wide insult region 535.

FIG. 47B shows a section of the acquisition/distribution structure 540 used in example 28 including the distribution of fiber bundle layer 535, a top layer 536, and a liquid resistance layer 537. The liquid resistance layer 537 includes a liquid impermeable section 538. In the liquid acquisition/distribution 540 used in example 28, the top layer 536 and bottom layer 537 are formed from Dri-weave® (a perforated polyethylene film) and the impermeable section 538 is formed from a liquid impermeable polymer film.

Figure 48:
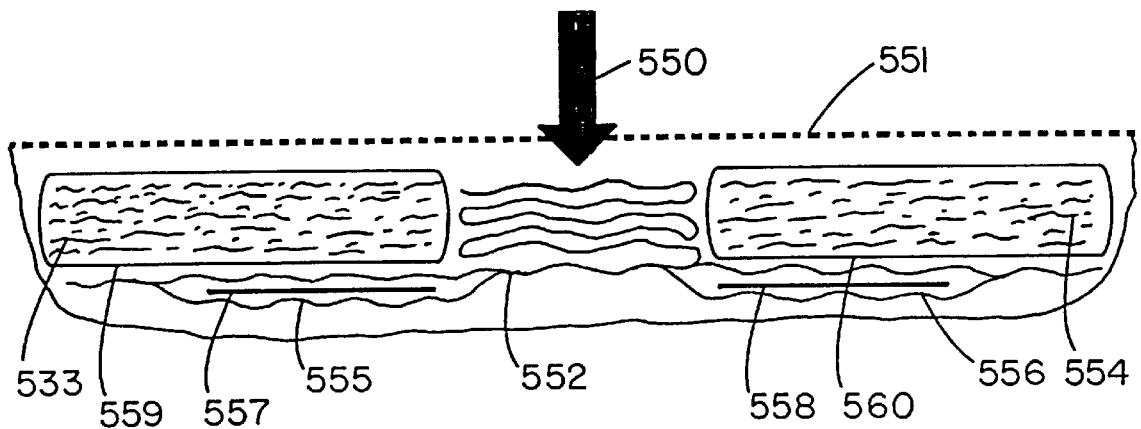
FIG. 48 is a side view of an alternative embodiment of the liquid acquisition/distribution structure of the present invention.

FIG. 48 is a schematic side section view of an alternative absorbent product of the invention showing a liquid insult 550, a top sheet 551 directly above a liquid acquisition/distribution structure 552, and the absorbent cores 553 and 554. Adjacent to liquid acquisition/distribution structure 552 and on either side thereof are absorbent cores 553 and 554. The liquid acquisition/distribution structure extends to regions 555 and 556 that are beneath the absorbent cores. Liquid resistance layers 557 and 558 at least partially between the absorbent cores and the liquid distribution layers sections 555 and 556 allow the liquid in the distribution layer 552 to spread out so that the liquid impinges the absorbent core along a substantial length of the bottom surfaces 559 and 560 of the absorbent cores. Portions of the distribution layer may be between the flow resistance layer and the absorbent core in order to improve the distribution of the liquid. Thus, the distribution layer may be split into two layers, and each of the two layers extends under a different one of the two absorbent cores.

The distribution layer may be formed from a helically crimped spontaneously wettable fiber tow or the bundled tows described herein that are divided into two sections on each end of the distribution structure. These two sections are separated by the liquid resistance layers 557, 558, which may be formed form thin plastic film. This separation of parts of the distribution layer by the liquid resistance layers 557, 558 allows part of the liquid to be transferred from the insult region to the absorbent material close to the insult region (fibers on top of the liquid resistance layers 557, 558) and part of it to be transferred to the extremity of the pad (carried by the fibers on the bottom of the liquid resistance layers 557, 558). The resistance layers 557 and 558 could also be made from the same material as that of the top layer (e.g. Dri-weave®) and could extend the full length of the absorbent cores 553 and 554.

The structure of FIG. 48 may be used in any absorbent article. Obviously, the size of the pieces required depends on the article of choice (i.e. feminine napkin or diaper, etc.). The specific volume of the spontaneously wettable tow in the insult region should be between 5 and 75 cc/gm. The absorbent core storage material is fluff pulp although blends of fluff and SAP or chemically treated cellulose may also be used.

Figure 49:
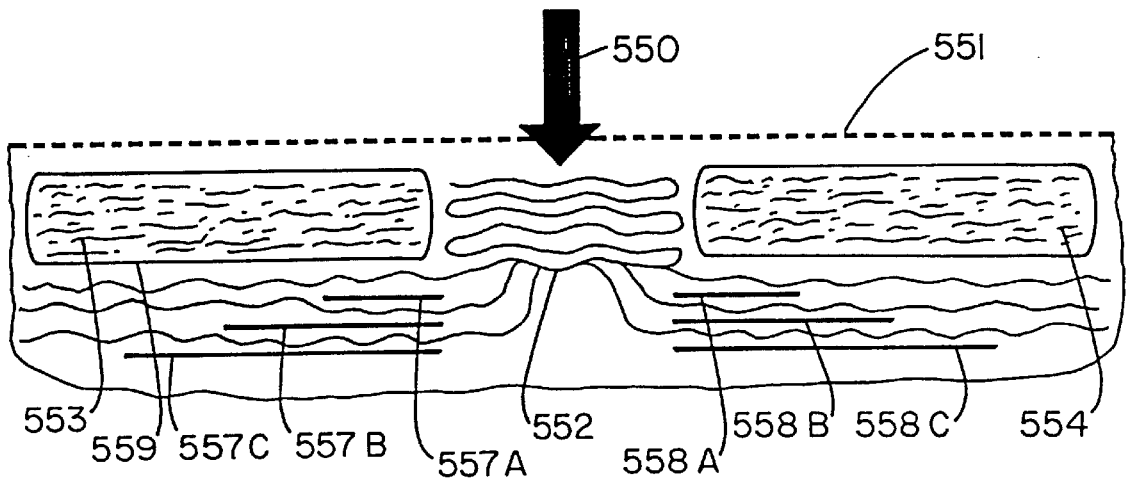
FIG. 49 is a side view of another alternative embodiment of a liquid acquisition/distribution structure of the present invention.

FIG. 49 shows another alternative embodiment of the absorbent product of the present invention in which there are three flow resistance layers below each of the absorbent cores. The liquid resistance layers 557A, 557B, and 557C extend various lengths beneath the absorbent core in order to more uniformly distribute the liquid to the bottom surface 559 of the absorbent core 553. Further, the bottom liquid resistance layer 557C may be liquid impermeable in order to prevent liquid from escaping from the absorbent product. Significantly, the distribution structure of the absorbent product shown in FIG. 49 splits into three separate layers separated by the layered liquid resistance layers beneath each absorbent core in order to provide uniform distribution of the liquid to the bottom surface of each absorbent core.

Figure 50:
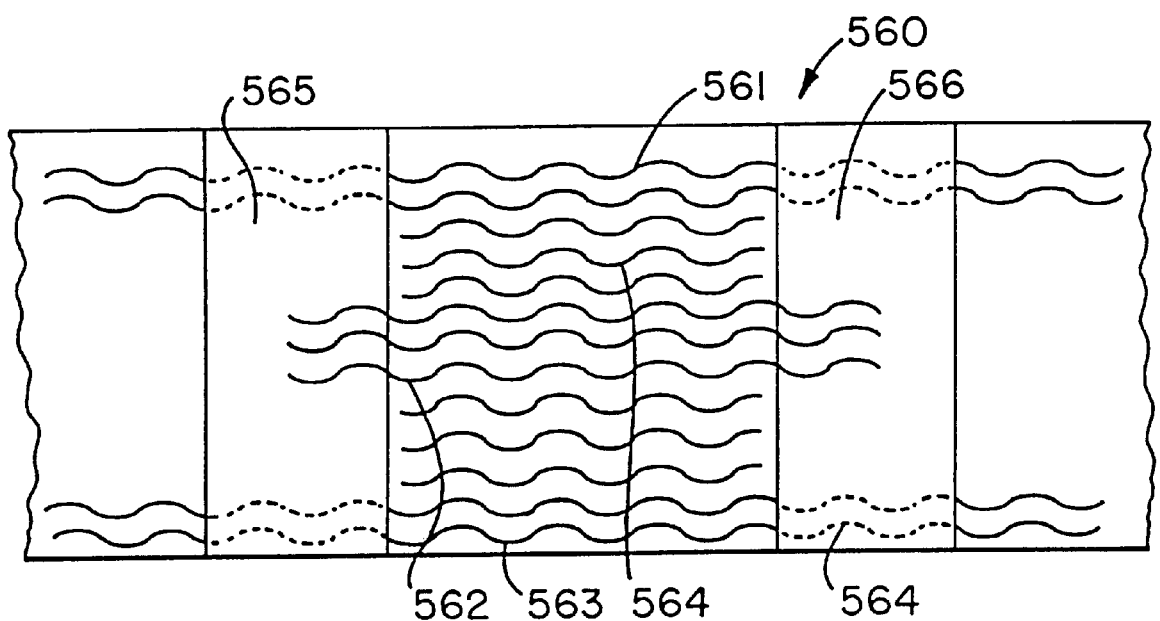
FIG. 50 is a top view of yet another alternative embodiment of a liquid acquisition/distribution structure of the present invention.

FIG. 50 shows still another alternative liquid acquisition/distribution structure 560 which includes an insult region 561, and a distribution structure that distributes the liquid away from the insult region 561. The liquid acquisition/distribution structure 560 includes the tows, 562, 563, 564 that have different lengths. The tows 562 extend from the insult region 561 to points directly above the liquid flow resistance layers 565, 566. The tows 564 extend substantially only the length of the insult region 561. The tows 563 extend underneath the liquid flow resistance layers 561 and 565, and extend beyond the ends of those layers.

The different length tows are useful in distributing liquid to different distances away from the insult region 561 in order to make the distribution of the liquid to the absorbent core (not shown in FIG. 50) more uniform. Variations may be made by using pieces of thin film that are curved instead of straight. The curvature of the films can control access to various locations in the absorbent core material.

In still another variation, there are three tows in the distribution structure and the central tow may be about three times the size of the other two tows. The larger central tow provides a raised portion in the structure which provides a better anatomical fit when the structure is used in a feminine napkin.

Figure 51A:
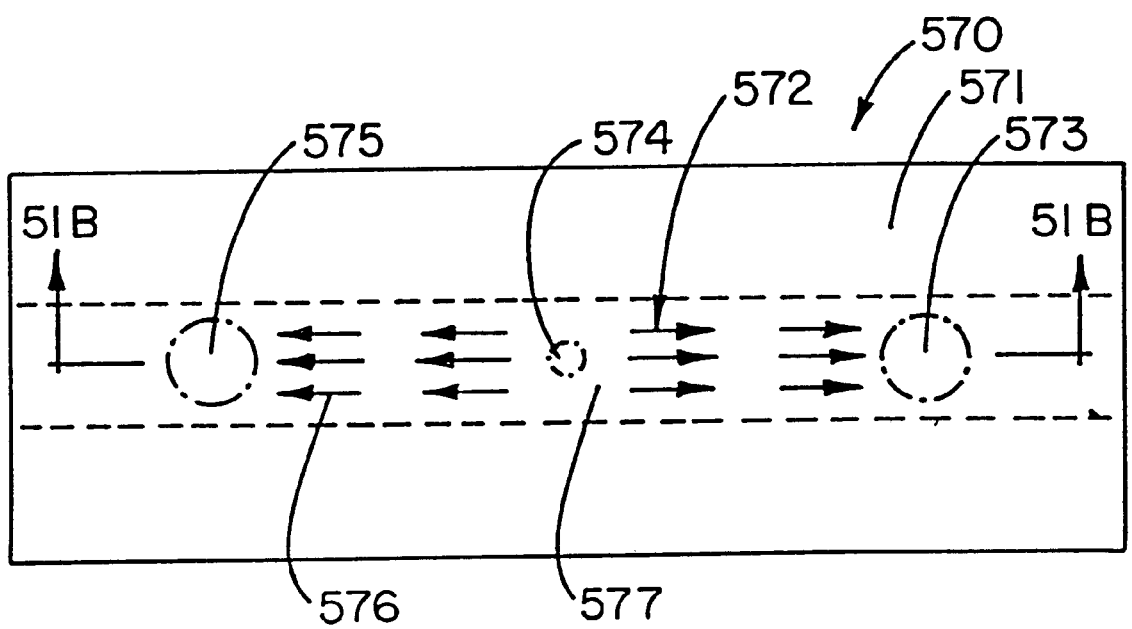
FIG. 51A is a schematic top plan view of an absorbent article of example 29.

FIG. 51A is a schematic top plan view of an absorbent article of prophetic example 29 showing the absorbent article 570's top layer 571 and indicating the location of the distribution layer 572, the location of the aperture or low resistance regions 573, 574, and 575 of the resistance layer 577 (see FIG. 51B), and including the arrows 576 illustrating an intended liquid flow pattern from the region of the top layer 571 above the aperture 574.

Figure 51B:
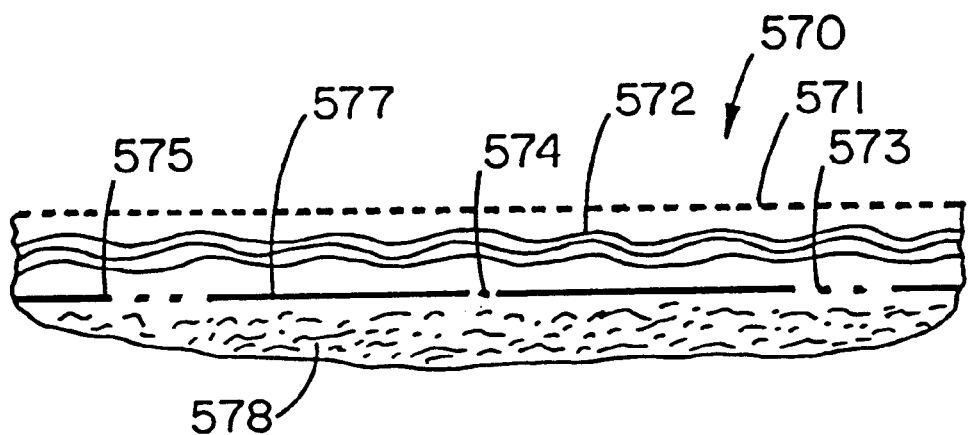
FIG. 51B is a partial side sectional view of the absorbent article of example 29.

FIG. 51B is a partial side sectional view of the absorbent article 570 showing the absorbent core 578 below the resistance layer 577. The apertures 573 and 575 are larger than the aperture 574. The absorbent article is designed to receive a liquid insult above the aperture 574, and to evenly distribute the liquid to the core through the three apertures 573, 574, and 575. Additional apertures may be provided in the resistance layer 577 in order to provide a more uniform distribution of liquid to the absorbent core 578.

EXAMPLES 1–14

FIBERS, BUNDLES AND SPINNERETTES

Example 1
(110/125/125 Y, PET, EGAN)

Example 1 describes the production of an undrawn continuous filament yarn useful in bundle structures for enhanced transport of liquids. The yarn is composed of 10 individual fibers, each having a Y-shaped cross-section with three equal arms and included angles of 110°, 125°, and 125°. The resulting fiber has three channels, two of which are approximately equal in width and area, with the third channel being slightly less in width and area.

Poly(ethylene terephthalate), (PET), polymer having an inherent viscosity (IV) of 0.75 and containing 0.2 percent titanium dioxide (TiO2) was used in preparing this yarn. Throughout the specification all IV values are measured in a 60/40 parts by weight solution of phenol/tetrachloroethane at 25° C. and at a concentration of about 0.5 gram of polymer in 100 mL of the solvent. The polymer was dried to a moisture level of less than or equal to 0.005 weight percent in a Patterson Conaform dryer at 120° C. for a period of at least 8 hours. The polymer was extruded at 280° C. using an Egan extruder having a 1.5 inch (38.1 millimeter) diameter screw of length to diameter ratio of 28:1. The polymer was spun through a spinnerette, numbered as I-1195, containing 10 individual orifices. The details of each orifice and the general layout of the spinnerette holes are shown in FIGS. 1A–1C.

The fiber, which had an IV of 0.69, was spun in a spinning cabinet having a cross flow air quench system using room temperature air at a velocity of about 51.8 meters/min. The individual fibers averaged 123 dpf. The yarn was taken up on a Leesona winder at 1000 meters per minute.

Spinning lubricant LK-5598-E10 was applied to the fiber at a level of 0.77 percent using a ceramic kiss roll just below the cabinet exit. LK-5598-E10 is a 10 weight percent solids water dispersion of the following components: 10 weight percent solution of poly[polyethyleneglycol (1400) terephthalate], 44.1 weight percent solids polyethylene glycol (400) monolaurate (oxyethylene fatty acid ester), 44.1 weight percent solids polyethylene glycol (600) monolaurate (oxyethylene fatty acid ester), and 1.8 weight percent solids 4-cetyl, 4-ethyl morpholinium ethosulfate (alkyl quaternary ammonium salt of inorganic ester).

A typical fiber cross-section for a fiber of example 1 is shown in FIG. 2. The generalized version of the shape of the cross-section is shown in FIG. 23. The fiber's cross-section properties were measured using fiber photomicrographs and a standard image analysis procedure. Liquid movement properties of fiber bundles and single fibers were measured using a special fiber wetting instrument shown in FIG. 27. This instrument is equipped with a video camera system capable of tracking the advancing liquid/air interface and determining the initial wetting velocity. Yarn specific volume was measured using a test method described earlier. Single Fiber Bulk Factor was calculated according to the method described above. The 8-fiber bundle maximum potential flux $MPF_8$ is calculated according to methods described in conjunction with FIG. 27. Single fiber Specific Capillary Volume (SCV), Specific Capillary Surface Area (SCSA) and slenderness ratio are calculated according to methods described in U.S. Pat. No. 5,200,248. Single fiber maximum potential flux $MPF_{SF}$ is calculated according to methods described in connection with FIG. 27. Average denier per filament was determined from the laboratory fiber cross-sectional area and the polymer density. The "X Factor" is calculated according to the method described in U.S. Pat. No. 5,268,229.

Fiber and liquid movement properties are as follows:

| | | |
|---|---|---|
| X-Factor | 1.21 | dimensionless |
| Denier per filament | 123 | dpf |
| Channel width (avg.), channel 1 ($x_1$, FIG. 2) | 332 | microns |
| Channel width (avg.), channel 2 ($x_2$, FIG. 2) | 537 | microns |
| Specific volume @ 0.05 gram/denier tension | 5.58 | cc/gm |
| Single fiber area | 10,311 | microns$^2$ |
| Single fiber total channel area | 80,770 | microns$^2$ |
| Single fiber channel area for flow | 10,492 | microns$^2$ |
| Single fiber percent channels <300 micron width | 0 | percent |
| Single fiber bulk factor | 7.83 | dimensionless |
| Single fiber total perimeter | 1811 | microns |
| Single fiber specific capillary volume | 3.21 | cc/gm |
| Single fiber specific capillary surface area | 577 | cm$^2$/gm |
| Single fiber slenderness ratio | 25.3 | dimensionless |
| Specific liq. movement force | 0.0458 | dyne/den |
| Single fiber initial liquid velocity | 34.1 | mm/sec |
| 8-fiber bundle initial liquid velocity | 70.0 | mm/sec |
| 8-fiber bundle maximum potential flux | 0.2701 | cc/(den*hr) |
| Single fiber maximum potential flux | 0.0210 | cc/(den*hr) |
| Single fiber vertical rise after 15 min | 3.65 | cm |
| Bundle vertical rise after 15 min | 6.04 | cm |
| $MPF_B/MPF_{SF}$ | 12.8 | dimensionless |
| $VR_B/VR_{SF}$ | 1.66 | dimensionless |

FIG. 23 shows a generalized version of the fiber cross-sections.

Example 2
(KNOBBY U, PET, HX)

This example describes the production of an undrawn continuous filament yarn not very useful in bundle structures for enhanced transport of liquids. The yarn is composed of 22 individual fibers, each having a "knobby" rectangular U-shaped cross-section. The base of the rectangular U is longer than the two equal arms forming the sides of the U, and the arms extend from the base at included angles generally greater than 90°. The fiber has a single large channel.

Poly(ethylene terephthalate), (PET), polymer having an IV of 0.70 and containing 0.2 percent titanium dioxide ($TiO_2$) was used in preparing this yarn. The polymer was dried to the same moisture level using the same equipment as in example 1. The polymer was extruded at 270° C. through a Hills R & D Extruder (designated HX) having a one inch (25.4 millimeter) diameter screw of length to diameter ratio of 24:1. The polymer was spun through a spinnerette, numbered I-1111, containing 22 individual orifices. The details of each orifice and the general layout of the spinnerette holes are shown in FIGS. 3A–3C.

The fiber, which had and IV of 0.63, was spun in a spinning cabinet having a cross flow air quench system using room temperature air at a velocity of 12.8 meters/min. Spinning lubricant LK-5598-E10, the same as in example 1, was applied to the fiber at a level of 0.63 percent using a ceramic kiss roll just below the cabinet exit. The individual fibers were 96 dpf. The yarn was taken up on a Leesona winder at 1000 meters per minute. A typical fiber cross-section is shown in FIG. 4. Fiber cross-section properties and liquid movement properties for single fibers and 8-fiber fiber bundles were measured using the same methods as described in example 1.

Fiber and liquid movement properties are as follows:

| | | |
|---|---|---|
| X-Factor | 1.52 | dimensionless |
| Denier per filament | 96 | dpf |
| Channel width (avg.), channel 1 ($x_1$, FIG. 4) | 365 | microns |
| Specific volume @ 0.05 gram/denier tension | 2.70 | cc/gm |
| Single fiber fiber area | 8,046 | microns$^2$ |
| Single fiber total channel area | 24,352 | microns$^2$ |
| Single fiber MPF effective channel area | 9,140 | microns$^2$ |
| Single fiber percent channels <300 micron width | 0 | percent |
| Single fiber bulk factor | 3.03 | dimensionless |
| Single fiber total perimeter | 1379 | microns |
| Single fiber specific capillary volume | 0.60 | cc/gm |
| Single fiber specific capillary surface area | 878 | cm$^2$/gm |
| Single fiber slenderness ratio | 85.7 | dimensionless |
| Specific liq. movement force | 0.0447 | dyne/den |
| Single fiber initial liquid velocity | 22.3 | mm/sec |
| 8-fiber bundle initial liquid velocity | 54.0 | mm/sec |
| 8-fiber bundle maximum potential flux | 0.0839 | cc/(den*hr) |
| Single fiber maximum potential flux | 0.0154 | cc/(den*hr) |
| $MPF_B/MPF_{SF}$ | 5.46 | dimensionless |
| Single fiber vertical rise after 15 min | 2.58 | cm |
| Bundle vertical rise after 15 min | 12.9 | cm |
| $VR_B/VR_{SF}$ | 4.98 | dimensionless |

This bundle is not a good liquid mover.

Example 3

(PLUS, PET, EGAN)

This example describes the production of an undrawn continuous filament yarn useful in bundle structures for enhanced transport of liquids. The yarn is composed of 13 individual fibers, each having a plus-shaped cross-section consisting of two opposing pairs of arms that form four 90° included angles. Each opposing pair of arms is of equal length, but the two pairs are of different length. The average width and area of the four resulting channels are approximately equal.

Poly(ethylene terephthalate), (PET), polymer having an IV of 0.76 and containing 0.2 percent titanium dioxide ($TiO_2$) was used in preparing this yarn. The polymer was dried to the same moisture level using the same equipment as in example 1. The polymer was extruded at 280° C. using the same extruder as in example 1. The polymer was spun through a spinnerette, numbered I-1199, containing 13 individual orifices. The details of each orifice and the general layout of the spinnerette holes are shown in FIGS. 5A–5D.

The fiber, which had an IV of 0.68, was spun in the same spinning cabinet as in example 1. The cross flow quench velocity was 36.6 meters/min. Spinning lubricant LK-5598-E10, the same as in example 1, was applied to the fiber at a level of 0.99 percent using the same equipment as in example 1. The individual fibers averaged 138 dpf. The yarn was taken up on a Leesona winder at 500 meters per minute.

A typical fiber cross-section is shown in FIG. 6. The general version of this shape is shown in FIG. 20. Fiber cross-section properties and liquid movement properties for single fibers and 8-fiber fiber bundles were measured using the same methods as described in example 1.

Fiber and liquid movement properties are as follows:

| | | |
|---|---|---|
| X-Factor | 1.26 | dimensionless |
| Denier per fiber | 38 | dpf |
| Channel width (avg.), channel 1 ($x_1$, FIG. 6) | 333 | microns |
| Specific volume @ 0.05 gram/denier tension | 4.28 | cc/gm |
| Single fiber fiber area | 11,570 | microns$^2$ |
| Single fiber total channel area | 77,083 | microns$^2$ |
| Single fiber capillary channel area for flow | 22,156 | microns$^2$ |
| Single fiber percent channels <300 micron width | 0 | percent |
| Single fiber bulk factor | 6.66 | dimensionless |
| Single fiber total perimeter | 1953 | microns |
| Single fiber specific capillary volume | 2.77 | cc/gm |
| Single fiber specific capillary surface area | 1121 | cm$^2$/gm |
| Single fiber slenderness ratio | 19.0 | dimensionless |
| Specific liq. movement force | 0.0441 | dyne/den |
| Single fiber initial liquid velocity | 42.7 | mm/sec |
| 8-fiber bundle initial liquid velocity | 68.9 | mm/sec |
| 8-fiber bundle maximum potential flux | 0.1942 | cc/(den*hr) |
| Single fiber maximum potential flux | 0.0607 | cc/(den*hr) |
| $MPF_B/MPF_{SF}$ | 3.20 | dimensionless |
| Single fiber vertical rise after 15 min | 5.85 | cm |
| Bundle vertical rise after 15 min | 7.88 | cm |
| $VR_B/VR_{SF}$ | 1.35 | dimensionless |

FIG. 20 shows a generalized version of this cross-section.

Example 4
(SKEWED PLUS, PET, EGAN)

This example describes the production of an undrawn continuous filament yarn useful in bundle structures for enhanced transport of liquids. The yarn is composed of 11 individual fibers, each having a skewed plus-shaped cross-section consisting of four arms of generally unequal length that meet to form four approximately 90° included angles. This results in four channels having generally unequal widths and unequal areas.

Poly(ethylene terephthalate), (PET) polymer having an IV of 0.76 and containing 0.2 percent Titanium dioxide ($TiO_2$) was used in preparing this yarn. The polymer was extruded at 280° C. using the same extruder as in example 1. The polymer was spun through a spinnerette, numbered I-1198, containing 11 individual orifices. The details of each orifice and the general layout of the spinnerette holes are shown in FIGS. 7A–7D.

The fiber, which had an IV of 0.67, was spun in the same spinning cabinet as example 1. The cross flow quench velocity was 21.3 meters/min. Spinning lubricant LK-5598-E10, the same as in example 1, was applied to the fiber at a level of 0.80 percent using the same equipment as in example 1. The individual fibers averaged 123 dpf. The yarn was taken up on a Leesona winder at 700 meters per minute.

A typical fiber cross-section is shown in FIG. 8. The general shape is shown FIG. 20. Fiber cross-section properties and liquid movement properties for single fibers and 8-fiber fiber bundles were measured using the same methods as described in example 1.

Fiber and liquid movement properties are as follows:

| | | |
|---|---|---|
| X-Factor | 1.22 | dimensionless |
| Denier per filament | 123 | dpf |
| Channel width (avg.), channel 1 ($x_1$, FIG. 8) | 358 | microns |
| Channel width (avg.), channel 2 ($x_2$, FIG. 8) | 125 | microns |
| Channel width (avg.), channel 3 ($x_3$, FIG. 8) | 347 | microns |
| Channel width (avg.), channel 4 ($x_4$, FIG. 8) | 624 | microns |
| Specific volume @ 0.05 gram/denier tension | 4.83 | cc/gm |
| Single fiber fiber area | 10,313 | $microns^2$ |
| Single fiber total channel area | 63,911 | $microns^2$ |
| Single fiber capillary channel area for flow | 14,890 | $microns^2$ |
| Single fiber percent channels <300 micron width | 25 | percent |
| Single fiber bulk factor | 6.20 | dimensionless |
| Single fiber total perimeter | 1897 | microns |
| Single fiber specific capillary volume | 2.21 | cc/gm |
| Single fiber specific capillary surface area | 726 | $cm^2/gm$ |
| Single fiber slenderness ratio | 18.8 | dimensionless |
| Specific liq. movement force | 0.0480 | dyne/den |
| Single fiber initial liquid velocity | 38.2 | mm/sec |
| 8-fiber bundle initial liquid velocity | 73.0 | mm/sec |
| 8-fiber bundle maximum potential flux | 0.2378 | cc/(den*hr) |
| Single fiber maximum potential flux | 0.0334 | cc/(den*hr) |
| $MPF_B/MPF_{SF}$ | 7.12 | dimensionless |
| Single fiber vertical rise after 15 min | 4.51 | cm |
| Bundle vertical rise after 15 min | 8.91 | cm |
| $VR_B/VR_{SF}$ | 1.98 | dimensionless |

Example 5
(Orig. Wing, PP, Egan)

This example describes the production of an undrawn continuous filament yarn useful in bundle structures for enhanced transport of liquids. The yarn is composed of 20 individual fibers, each having a wing-shaped cross-section formed by two arms of equal length. The smaller included angle between these arms is bisected by a third shorter arm that results in two channels of approximately equal size and area.

Polypropylene, (PP), polymer having melt flow rate (MFR) of 18 grams of polymer per 10 minutes was used in preparing this yarn. MFR determination is per ASTM Test Method D-1238 at 230° C. using a die diameter of 2.095 mm and length of 8 mm. The polymer was spun through a spinnerette, numbered I-1187, containing 20 individual orifices. The details of each orifice and the general layout of the spinnerette holes are shown in FIGS. 9A–9D.

The fiber was spun in the same spinning cabinet as example 1. The cross flow quench velocity was about 5.8 meters/min. Spinning lubricant LK-5598-E10, the same as in example 1, was applied to the fiber at a level of 1.89 percent using the same equipment as in example 1. The individual fibers averaged 90.3 dpf. The yarn was taken up on a Leesona winder at 250 meters per minute.

A typical fiber cross-section is shown in FIG. 10. The general shapes are shown in FIGS. 22A, 22B, and 24. Fiber cross-section properties and liquid movement properties for single fibers and 8-fiber fiber bundles were measured using the same methods as described in example 1.

Fiber and liquid movement properties are as follows:

| | | |
|---|---|---|
| X-Factor | 1.23 | dimensionless |
| Denier per filament | 90.3 | dpf |
| Channel width (avg.), channel 1 ($x_1$, FIG. 10) | 387 | microns |
| Specific volume @ 0.05 gram/denier tension | 4.20 | cc/gm |
| Single fiber fiber area | 11,028 | $microns^2$ |
| Single fiber total channel area | 45,316 | $microns^2$ |
| Single fiber capillary channel area for flow | 10,195 | $microns^2$ |
| Single fiber percent channels <300 micron width | 0 | percent |
| Single fiber bulk factor | 5.11 | dimensionless |
| Single fiber total perimeter | 2086 | microns |
| Single fiber specific capillary volume | 2.15 | cc/gm |
| Single fiber specific capillary surface area | 1269 | $cm^2/gm$ |
| Single fiber slenderness ratio | 49.1 | dimensionless |
| Specific liq. movement force | 0.0716 | dyne/den |
| Single fiber initial liquid velocity | 23.9 | mm/sec |
| 8-fiber bundle initial liquid velocity | 56.5 | mm/sec |
| 8-fiber bundle maximum potential flux | 0.1407 | cc/(den*hr) |
| Single fiber maximum potential flux | 0.0194 | cc/(den*hr) |

|  |  |  |
|---|---|---|
| $MPF_B/MPF_{SF}$ | 7.25 | dimensionless |
| Single fiber vertical rise after 15 min | 0.83 | cm |
| Bundle vertical rise after 15 min | 9.74 | cm |
| $VR_B/VR_{SF}$ | 11.7 | dimensionless |

FIG. 22 shows a generalized version of this fiber cross-section.

Example 6
(BALANCED Y, PET, EGAN)

This example describes the production of an undrawn continuous fiber yarn useful in bundle structures for enhanced transport of liquids. The yarn is composed of 10 individual fibers, each having a generally symmetric Y-shaped cross-section consisting of three arms having generally the same average equal length that meet to form three approximately equal 120° included angles. This results in three channels having generally equal widths and equal areas.

Poly(ethylene terephthalate), (PET), polymer having an IV of 0.77 and containing 0.2 percent Titanium dioxide ($TiO_2$) was used in preparing this yarn. The polymer was dried to the same moisture level using the same extruder as in example 1. The polymer was spun through a spinnerette, numbered I-1208, containing 10 individual orifices. The details of each orifice and the general layout of the spinnerette holes are shown in FIGS. 11A–11D.

The fiber, which had an IV of 0.75, was spun in the same spinning cabinet as in example 1. The cross flow quench velocity was about 16.8 meters/min. Spinning lubricant LK-5598-E10, the same as in example 1, was applied to the fiber at a level of 0.36 percent using the same equipment as in example 1. The individual fibers averaged 77 dpf. The yarn was taken up on a Leesona winder at 1000 meters per minute.

A typical fiber cross-section is shown in FIG. 12. Fiber cross-section properties and liquid movement properties for single fibers and 8-fiber fiber bundles were measured using the same methods as described in example 1.

Fiber and liquid movement properties are as follows:

|  |  |  |
|---|---|---|
| X-Factor | 1.09 | dimensionless |
| Denier per fiber | 77 | dpf |
| Channel width (avg.), channel 1 ($x_1$, FIG. 12) | 390 | microns |
| Specific volume @ 0.05 gram/denier tension | 7.22 | cc/gm |
| Single fiber fiber area | 6,464 | microns$^2$ |
| Single fiber total channel area | 63,657 | microns$^2$ |
| Single fiber capillary channel area for flow | 9490 | microns$^2$ |
| Single fiber percent channels <300 micron width | 0 | percent |
| Single fiber bulk factor | 5.11 | dimensionless |
| Single fiber total perimeter | 1519 | microns |
| Single fiber specific capillary volume | 1.64 | cc/gm |
| Single fiber specific capillary surface area | 980 | cm$^2$/gm |
| Specific liq. movement force | 0.0613 | dyne/den |
| Single fiber initial liquid velocity | 27.6 | mm/sec |
| 8-fiber bundle initial liquid velocity | 69.7 | mm/sec |
| 8-fiber bundle maximum potential flux | 0.3603 | cc/(den*hr) |
| Single fiber maximum potential flux | 0.0246 | cc/(den*hr) |
| $MPF_B/MPF_{SF}$ | 14.7 | dimensionless |
| Single fiber vertical rise after 15 min | 2.85 | cm |
| Bundle vertical rise after 15 min | 6.64 | cm |
| $VR_B/VR_{SF}$ | 2.33 | dimensionless |

FIG. 23 shows a generalized version of the fiber cross-section.

Example 7
(CROSSED V, PET, EGAN)

This example describes the production of an undrawn continuous fiber yarn useful in bundle structures for enhanced transport of liquids. The yarn is composed of 10 individual fibers, each having a V-shaped cross-section consisting of two long arms of generally equal length that cross to form one large dominant channel, two additional moderately large channels of generally equal area and width that are adjacent to the large dominant channel, and one small channel opposite the large dominant channel. The included angles of the large dominant channel and smallest channel are approximately equal and the included angles of the two channels adjacent to the largest channel are approximately equal.

Poly(ethylene terephthalate), (PET), polymer having an IV of 0.77 and containing 0.2 percent Titanium dioxide ($TiO_2$) was used in preparing this yarn. The polymer was dried to the same moisture level using the same equipment as in example 1. The polymer was extruded at 281° C. using the same extruder as in example 1. The polymer was spun through a spinnerette, numbered I-1206, containing 10 individual orifices. The details of each orifice and the general layout of the spinnerette holes are shown in FIGS. 13A–13D.

The fiber, which had an IV of 0.75, was spun in the same spinning cabinet as in example 1. The cross flow quench velocity was about 16.8 meters/min. Spinning lubricant LK-5598-E10, the same as in example 1, was applied to the fiber at a level of 0.76 percent using the same equipment as in example 1. The individual fibers averaged 169 dpf. The yarn was taken up on a Leesona winder at 450 meters per minute.

A typical fiber cross-section is shown in FIG. 14. Fiber cross-section properties and liquid movement properties for single fibers and 8-fiber fiber bundles were measured using the same methods as described in example 1.

Fiber and liquid movement properties are as follows:

|  |  |  |
|---|---|---|
| X-Factor | 1.14 | dimensionless |
| Denier per fiber | 169 | dpf |
| Channel width (avg.), channel 1 ($x_1$, FIG. 14) | 375 | microns |
| Channel width (avg.), channel 2 ($x_2$, FIG. 14) | 58 | microns |
| Channel width (avg.), channel 3 ($x_3$, FIG. 14) | 837 | microns |
| Specific volume @ 0.05 gram/denier tension | 3.19 | cc/gm |
| Single fiber fiber area | 14,181 | microns$^2$ |

-continued

| | | |
|---|---|---|
| Single fiber total channel area | 87,066 | microns$^2$ |
| Single fiber capillary channel area for flow | 8,795 | microns$^2$ |
| Single fiber percent channels <300 micron width | 25 | percent |
| Single fiber bulk factor | 6.14 | dimensionless |
| Single fiber total perimeter | 2334 | microns |
| Single fiber specific capillary volume | 0.67 | cc/gm |
| Single fiber specific capillary surface area | 688 | cm$^2$/gm |
| Specific liq. movement force | 0.0430 | dyne/den |
| Single fiber initial liquid velocity | 26.1 | mm/sec |
| 8-fiber bundle initial liquid velocity | 73.2 | mm/sec |
| 8-fiber bundle maximum potential flux | 0.1424 | cc/(den*hr) |
| Single fiber maximum potential flux | 0.00981 | cc/(den*hr) |
| MPF$_B$/MPF$_{SF}$ | 14.5 | dimensionless |
| Single fiber vertical rise after 15 min | 1.71 | cm |
| Bundle vertical rise after 15 min | 7.45 | cm |
| VR$_B$/VR$_{SF}$ | 4.36 | dimensionless |

Example 8

(TEE, PET, EGAN)

This example describes the production of an undrawn continuous fiber yarn useful in bundle structures for enhanced transport of liquids. The yarn is composed of 10 individual fibers, each having a T-shaped cross-section consisting of two arms of generally equal length forming the bar or top of the T and a third longer arm forming the long or body member of the T. The two arms forming the top of the T are of generally the same length. The two included angles between the body of the T and the arms forming the top of the T are approximately equal and are generally somewhat greater than 90°, resulting in a large included angle between the arms forming the top of the T. This results in the formation of two channels having relatively large widths and areas and a third channel having a relatively large channel width but considerably less area.

Poly(ethylene terephthalate), (PET), polymer having an IV of 0.77 and containing 0.2 percent Titanium dioxide (TiO$_2$) was used in preparing this yarn. The polymer was dried to the same moisture level using the same equipment as in example 1. The polymer was extruded at 280° C. using the same extruder as in example 1. The polymer was spun through a spinnerette, numbered I-1205, containing 10 individual orifices. The details of each orifice and the general layout of the spinnerette holes are shown in FIGS. 15A–15D.

The fiber, which had an IV of 0.75, was spun in the same spinning cabinet as in example 1. The cross flow quench velocity was about 16.8 meters/min. Spinning lubricant LK-5598-E10, the same as in example 1, was applied to the fiber at a level of 0.73 percent using the same equipment as in example 1. The individual fibers averaged 160 dpf. The yarn was taken up on a Leesona winder at 500 meters per minute.

A typical fiber cross-section is shown in FIG. 16. Fiber cross-section properties and liquid movement properties for single fibers and 8-fiber fiber bundles were measured using the same methods as described in example 1.

Fiber and liquid movement properties are as follows:

| | | |
|---|---|---|
| X-Factor | 1.07 | dimensionless |
| Denier per fiber | 160 | dpf |
| Channel width (avg.), channel 1 (x$_1$, FIG. 16) | 473 | microns |
| Channel width (avg.), channel 2 (x$_2$, FIG. 16) | 572 | microns |
| Specific volume @ 0.05 gram/denier tension | 5.93 | cc/gm |
| Single fiber fiber area | 13,478 | microns$^2$ |
| Single fiber total channel area | 106,592 | microns$^2$ |
| Single fiber capillary channel area for flow | 13,365 | microns$^2$ |
| Single fiber percent channels <300 micron width | 0 | percent |
| Single fiber bulk factor | 7.91 | dimensionless |
| Single fiber total perimeter | 2130 | microns |
| Single fiber specific capillary volume | 1.91 | cc/gm |
| Single fiber specific capillary surface area | 416 | cm$^2$/gm |
| Specific liq. movement force | 0.0412 | dyne/den |
| Single fiber initial liquid velocity | 36.5 | mm/sec |
| 8-fiber bundle initial liquid velocity | 71.3 | mm/sec |
| 8-fiber bundle maximum potential flux | 0.2950 | cc/(den*hr) |
| Single fiber maximum potential flux | 0.0219 | cc/(den*hr) |
| MPF$_B$/MPF$_{SF}$ | 13.4 | dimensionless |
| Single fiber vertical rise after 15 min | 3.83 | cm |
| Bundle vertical rise after 15 min | 5.19 | cm |
| VR$_B$/VR$_{SF}$ | 1.36 | dimensionless |

FIG. 24 shows a generalized version of this fiber cross-section.

Example 9

(C, PET, EGAN)

This example describes the production of an undrawn continuous fiber yarn useful in bundle structures for enhanced transport of liquids. The yarn is composed of 11 individual fibers, each having a C-shaped cross-section. This results in one major channel formed by the C shape.

Poly(ethylene terephthalate), (PET), polymer having an IV of 0.77 and containing 0.2 percent Titanium dioxide (TiO$_2$) was used in preparing this yarn. The polymer was dried to the same moisture level using the same equipment as in example 1. The polymer was extruded at 283° C. using the same extruder as in example 1. The polymer was spun through a spinnerette, numbered I-1200, containing 11 individual orifices. The details of each orifice and the general layout of the spinnerette holes are shown in FIGS. 17A–17D.

The fiber, which had an IV of 0.75, was spun in the same spinning cabinet as in example 1. The cross flow quench velocity was about 16.7 meters/min. Spinning lubricant LK-5598-E10, the same as in example 1, was applied to the fiber at a level of 0.61 percent using the same equipment as in example 1. The individual fibers averaged 156 dpf. The yarn was taken up on a Leesona winder at 500 meters per minute.

A typical fiber cross-section is shown in FIG. 18. Fiber cross-section properties and liquid movement properties for single fibers and 8-fiber fiber bundles were measured using the same methods as described in example 1.

Fiber and liquid movement properties are as follows:

| | | |
|---|---|---|
| X-Factor | 1.20 | dimensionless |
| Denier per fiber | 156 | dpf |
| Channel width (avg.), channel 1 ($x_1$, FIG. 18) | 686 | microns |
| Specific volume @ 0.05 gram/denier tension | 3.56 | cc/gm |
| Single fiber fiber area | 13,133 | microns$^2$ |
| Single fiber total channel area | 111,081 | microns$^2$ |
| Single fiber capillary channel area for flow | 5,608 | microns$^2$ |
| Single fiber percent channels <300 micron width | 0 | percent |
| Single fiber bulk factor | 8.46 | dimensionless |
| Single fiber total perimeter | 2055 | microns |
| Single fiber specific capillary volume | 0.74 | cc/gm |
| Single fiber specific capillary surface area | 458 | cm$^2$/gm |
| Specific liq. movement force | 0.0408 | dyne/den |
| Single fiber initial liquid velocity | 22.9 | mm/sec |
| 8-fiber bundle initial liquid velocity | 72.8 | mm/sec |
| 8-fiber bundle maximum potential flux | 0.1632 | cc/(den*hr) |
| Single fiber maximum potential flux | 0.0593 | cc/(den*hr) |
| $MPF_B/MPF_{SF}$ | 27.6 | dimensionless |
| Single fiber vertical rise after 15 min | 1.49 | cm |
| Bundle vertical rise after 15 min | 5.96 | cm |
| $VR_B/VR_{SF}$ | 4.00 | dimensionless |

Example 10

This example pertains to the fibers described in FIGS. 19A–19C. These fibers bundles can be made on equipment described in example 1 and under similar spinning conditions. Bundles of these fibers behave similarly to those shown in the other examples.

Cross sections of the type shown in FIG. 19A can be difficult to make because the melt surface tension tends to straighten out unbalanced intersections.

For example, to make the shallow channel polymeric structure with the section shown in FIG. 19B, the steep channel spinnerette aperture shown in FIG. 19C is required.

The specific shape required depends on the polymer being extruded, the extrusion conditions, and the quenching conditions. Thus trial and error is required to specify the exact spinnerette hole shape required.

This is true also for the fibers with the shapes shown in FIGS. 22A–22B which require a spinnerette having the aperture shown in FIG. 22C.

Example 11

This example discloses fibers of the type shown in FIG. 21A. These fibers/bundles can be made on equipment described in example 1 and under similar spinning conditions. Bundles of these fibers behave similarly to those shown in the other examples.

There is surprising difficulty in producing these types of fibers without having a pronounced curl in the sides of the "H" as shown in FIG. 21C, because of the surface tension of the molten polymer.

These fibers have a reduced specific volume as compared to fibers with straight vertical arms. This curvature is caused by the massive shortening of the "bar" of the "H" because of surface tension. This "shortening" pulls at the center of the vertical walls during quenching and thereby produces the "C" shaped vertical bar. This condition is corrected by designing a spinnerette having the apertures shown in FIGS. 21D–21G.

Obviously, the amount of the correction (i.e., bend in the arms of the spinnerette) required depends on the specific design being used and the size and spinning conditions of the desired fiber. Therefore, some trial and error is required.

Bundles of these fibers behave similarly to those in the other examples.

Comparative Example 12
(H, PET, EGAN)

This example describes the production of an undrawn continuous fiber yarn useful in bundle structures for enhanced transport of liquids. The yarn is composed of 16 individual fibers, each having an "H"-shaped cross-section consisting of four arms of generally equal length and a crossbar connecting the arms to form the H. The four arms join the crossbar to form two major channels that are generally rectangular in shape and that are approximately equal in area and channel width. Each of the channels contains two included angles that are approximately 90° each.

Poly(ethylene terephthalate), (PET), polymer having an IV of 0.89 and containing 0.2 percent Titanium dioxide ($TiO_2$) was used in preparing this yarn. The polymer was dried to the same moisture level using the same equipment as in example 1. The polymer was extruded at 296° C. using the same extruder as in example 1. The polymer was spun through a spinnerette, numbered I-1011, containing 16 individual orifices. The details of each orifice and the general layout of the spinnerette holes are shown in FIGS. 30A–30B.

The fiber, which had an IV of 0.68, was spun in the same spinning cabinet as in example 1. The cross flow quench velocity was about 33.6 meters/min. spinning lubricant LK-5598-E10, the same as in example 1, was applied to the fiber at a level of 0.82 percent using the same equipment as in example 1. The individual fibers averaged 44.8 dpf. The yarn was taken up on a Leesona winder at 500 meters per minute.

A typical fiber cross-section is shown in FIG. 31. Fiber cross-section properties and liquid movement properties for single fibers and 8-fiber fiber bundles were measured using the same methods as described in example 1.

Fiber and liquid movement properties are as follows:

| | | |
|---|---|---|
| X-Factor | 1.78 | dimensionless |
| Denier per fiber | 44.8 | dpf |
| Channel width (avg.), channel 1 ($x_1$, FIG. 31) | 37 | microns |
| Specific volume @ 0.05 gram/denier tension | 2.35 | cc/g |
| Single fiber fiber area | 3,767 | microns$^2$ |
| Single fiber total channel area | 5,845 | microns$^2$ |
| Single fiber capillary channel area for flow | 5,405 | microns$^2$ |
| Single fiber percent channels <300 micron width | 100 | percent |
| Single fiber bulk factor | 1.55 | dimensionless |
| Single fiber total perimeter | 744 | microns |
| Single fiber specific capillary volume | 1.11 | cc/gm |

| | | |
|---|---|---|
| Single fiber specific capillary surface area | 747 | cm²/gm |
| Single fiber slenderness ratio | 19.8 | dimensionless |
| Specific liq. movement force | 0.0515 | dyne/den |
| Single fiber initial liquid velocity | 31.9 | mm/sec |
| 8-fiber bundle initial liquid velocity | 50.0 | mm/sec |
| 8-fiber bundle maximum potential flux | 0.0637 | cc/(den*hr) |
| Single fiber maximum potential flux | 0.0277 | cc/(den*hr) |
| $MPF_B/MPF_{SF}$ | 2.30 | dimensionless |
| Single fiber vertical rise after 15 min. | 5.46 | cm |
| Bundle vertical rise after 15 min. | 12.4 | cm |
| $VR_B/VR_{SF}$ | 2.27 | dimensionless |

Notice that bundles of this fiber do not meet our limitation of exceeding 0.14 (cc/den*hr) in the 8-fiber $MPF_B$ test even though the individual fibers are excellent wetters.

Comparative Example 13
(H, PET, EGAN)

This example describes the production of an undrawn continuous fiber yarn useful in bundle structures for enhanced transport of liquids. The yarn is composed of 32 individual fibers, each having an H-shaped cross-section consisting of four arms of generally equal length and a crossbar connecting the arms to form the H. The four arms join the crossbar to form two major channels that are generally rectangular in shape and that are approximately equal in area and channel width. Each of the channels contains two included angles that are approximately 90° each.

Poly(ethylene terephthalate), (PET), polymer having an IV of 0.76 and containing 0.2 percent Titanium dioxide ($TiO_2$) was used in preparing this yarn. The polymer was dried to the same moisture level using the same equipment as in example 1. The polymer was extruded at 283° C. using the same extruder as in example 1. The polymer was spun through an oval spinnerette, numbered I-1148, containing 32 individual orifices. The details of each orifice and the general layout of the spinnerette holes are shown in FIGS. 32C.

The fiber, which had an IV of 0.63, was spun in the same spinning cabinet as in example 1. The cross flow quench velocity was about 42.7 meters/min. Spinning lubricant LK-5598-E10, the same as in example 1, was applied to the fiber at a level of 1.02 percent using the same equipment as in example 1. The individual fibers averaged 31.6 dpf. The yarn was taken up on a Leesona winder at 1000 meters per minute.

A typical fiber cross-section is shown in FIG. 33. Fiber cross-section properties and liquid movement properties for single fibers and 8-fiber fiber bundles were measured using the same methods as described in example 1.

Fiber and liquid movement properties are as follows:

| | | |
|---|---|---|
| X-Factor | 1.39 | dimensionless |
| Denier per fiber | 31.6 | dpf |
| Channel width (avg.), channel 1 ($x_1$, FIG. 33) | 124 | microns |
| Specific volume @ 0.05 gram/denier tension | 4.39 | cc/gm |
| Single fiber fiber area | 2,659 | microns² |
| Single fiber total channel area | 11,119 | microns² |
| Single fiber capillary channel area for flow | 12,153 | microns² |
| Single fiber percent channels <300 micron width | 100 | percent |
| Single fiber bulk factor | 4.18 | dimensionless |
| Single fiber total perimeter | 737 | microns |
| Single fiber specific capillary volume | 2.84 | cc/gm |
| Single fiber specific capillary surface area | 1244 | cm²/gm |
| Single fiber slenderness ratio | 27.1 | dimensionless |
| Specific liq. movement force | 0.0723 | dyne/den |
| Single fiber initial liquid velocity | 23.2 | mm/sec |
| 8-fiber bundle initial liquid velocity | 53.2 | mm/sec |
| 8-fiber bundle maximum potential flux | 0.1546 | cc/(den*hr) |
| Single fiber maximum potential flux | 0.0643 | cc/(den*hr) |
| $MPF_B/MPF_{SF}$ | 2.41 | dimensionless |
| Single fiber vertical rise after 15 min. | 3.49 | cm |
| Bundle vertical rise after 15 min. | 9.32 | cm |
| $VR_B/VR_{SF}$ | 2.67 | dimensionless |

Notice that bundles of this excellently wetting single fiber only slightly exceed the limitation of $MPF_B$ exceeding 0.14 (cc/den*hr). This is very surprising!

Comparative Example 14
(H, PET, EGAN)

The spinnerette used was I-1148 with 32 holes (See FIG. 32) and the spinning system was the same as example 1. The polymer was semi dull PET with an IV of 0.778. The spinning speed was 1500 meters/min. with a quench air flow of approximately 43 meters/min. at a melt temperature of about 285° C. The hydrophilic finish, LK 5598-E10, was applied at approximately a 1.1% level.

Fiber, bundle and liquid movement properties are shown below:

| | | |
|---|---|---|
| X-Factor | 1.76 | dimensionless |
| Denier per fiber | 40 | dpf |
| Channel width ($x_1$, FIG. 34) | 122 | microns |
| Specific volume @ 0.05 gram/denier tension | 4.96 | cc/gm |
| Single fiber fiber area | 3,363 | microns² |
| Single fiber total channel area | 18,172 | microns² |
| Single fiber capillary channel area for flow | 18,172 | microns² |
| Single fiber percent channels <300 micron width | 100 | percent |
| Single fiber bulk factor | 5.40 | dimensionless |
| Single fiber total perimeter | 941 | microns |
| Single fiber specific capillary volume | 3.17 | cc/gm |
| Single fiber specific capillary surface area | 1017 | cm²/gm |
| Single fiber slenderness ratio | 30.6 | dimensionless |
| Specific liq. movement force | 0.0729 | dyne/den |
| Single fiber initial liquid velocity | 31.3 | mm/sec |
| 8-fiber bundle initial liquid velocity | 57.6 | mm/sec |

-continued

| | | |
|---|---|---|
| 8-fiber bundle maximum potential flux | 0.19 | cc/(den*hr) |
| Single fiber maximum potential flux | 0.10 | cc/(den*hr) |
| $MPF_B/MPF_{SF}$ | 1.90 | dimensionless |
| Single fiber vertical rise after 15 min. | 3.7 | cm |
| Bundle vertical rise after 15 min. | 9.7 | cm |
| $VR_B/VR_{SF}$ | 2.6 | dimensionless |

This particular sample represents about the best single fiber wetting "H" made to date. Yet, and very surprisingly, the bundle performance exceeds 0.14 (cc/den*hr) by only 35% and the $MPF_B/MPF_{SF}$ ratio is only 1.90. This compares to Example 6 which exceeds the 0.14 (cc/den*hr) limitation by 157% and has a $MPF_B/MPF_{SF}$ ratio of 14.7. Clearly, better performing bundles can be made from poorer performing single fibers.

Based upon the figures of the cross-sections of the examples and the magnifications of those figures, the lengths and widths of the arms of the cross-sections were measured.

The arms of the cross-section of the fibers of example 1 have lengths between about 280 and 360 microns and a length to width ratio (L/W) ranging between 22 and 27 for the width of the arms about half way along the arms.

For example 3, arm lengths are between about 120 and 380 microns and L/W is between about 10 and 28.

For example 4, the arm lengths are between about 100 and 400 microns and L/W is between about 5 and 31.

For example 5, the arm lengths are between about 60 and 460 microns and the L/W is between about 6 and 35.

For example 6, the arm lengths are between about 200 and 250 microns and L/W is between about 22 and 25.

For example 7, the arm lengths are between about 40 and 700 microns and LAW is between about 3 and 35.

For example 9, the length of the "C" shaped cross-section is between about 800 and 900 microns and L/W for the cross-section is between about 40 and 60.

For examples 1–8, the widths of the arms at their midpoints are less than 20 microns and greater than 5 microns.

For example 9, the width of the cross-section at the center of the "C" shape is less than 40 microns.

The fibers of examples 3 and 7 have two relatively short arms and two relatively long arms. The two relatively long arms of the fiber of example 7 form an angle of about 120°. The arms of the fiber of example 3 form angles of about 90°. The fiber of example 5 has one relatively short arm and two relatively long arms. For example 5, the two relatively long arms form an angle of about 180° and each relatively long arm forms an angle of about 90° with the relatively short arm.

The properties of examples 1–14 are summarized in Table Nos. IA–ID.

TABLE IA

| Example No. | X | Denier per Fiber (dpf) | Average Channel Width (Microns) | Specific Volume (cc/gm) | Single Fiber Cross-Section Area (Microns)² | Single Fiber Total Channels' Area (Micron)² | Single Fiber Capillary Area for Flow (Micron)² |
|---|---|---|---|---|---|---|---|
| 1 | 1.21 | 123 | (1) 332 (2) 537 | 5.58 | 10,311 | 80,770 | 10,492 |
| 2 | 1.52 | 96 | 365 | 2.70 | 8,046 | 24,352 | 9,140 |
| 3 | 1.26 | 38 | 333 | 4.28 | 11,570 | 77,083 | 22,156 |
| 4 | 1.22 | 123 | (1) 358 (2) 125 (3) 347 (4) 624 | 4.83 | 10,313 | 63,911 | 14,890 |
| 5 | 1.23 | 90.3 | 387 | 4.20 | 11,028 | 45,316 | 10,195 |
| 6 | 1.09 | 77 | 390 | 7.22 | 6,464 | 63,657 | 9,490 |
| 7 | 1.14 | 169 | (1) 375 (2) 58 (3) 837 | 3.19 | 14,181 | 87,066 | 8,795 |
| 8 | 1.07 | 160 | (1) 473 (2) 572 | 5.93 | 13,478 | 106,592 | 13,365 |
| 9 | 1.20 | 156 | 686 | 3.56 | 13,133 | 111,081 | 5,608 |
| 10 | — | — | — | — | — | — | — |
| 11 | — | — | — | — | — | — | — |
| 12 | 1.78 | 44.8 | 37 | 2.35 | 3,767 | 5,845 | 5,405 |
| 13 | 1.39 | 31.6 | 124 | 4.39 | 2,659 | 11,119 | 12,153 |
| 14 | 1.76 | 40 | 122 | 4.96 | 3,363 | 18,172 | 18,172 |

TABLE IB

| Example No. | Single Fiber's % of Channels Having a Width <300 (Microns) | Single Fiber Bulk Factor | Single Fiber Total Perimeter (Microns) | Single Fiber SCV (cc/gm) | Single Fiber SCSA cm²/gm) | Single Fiber Slenderness Ratio(s) |
|---|---|---|---|---|---|---|
| 1 | 0 | 7.83 | 1811 | 3.21 | 577 | 25.3 |
| 2 | 0 | 3.03 | 1379 | 0.60 | 878 | 85.7 |
| 3 | 0 | 6.66 | 1953 | 2.77 | 1121 | 19.0 |
| 4 | 25 | 6.20 | 1897 | 2.21 | 726 | 18.8 |
| 5 | 0 | 5.11 | 2086 | 2.15 | 1269 | 49.1 |
| 6 | 0 | 5.11 | 1519 | 1.64 | 980 | — |
| 7 | 25 | 6.14 | 2334 | 0.67 | 688 | — |
| 8 | 0 | 7.91 | 2130 | 1.91 | 416 | — |
| 9 | 0 | 8.46 | 2055 | 0.74 | 458 | — |
| 10 | — | — | — | — | — | — |
| 11 | — | — | — | — | — | — |
| 12 | 100 | 1.55 | 744 | 1.11 | 747 | 19.8 |
| 13 | 100 | 4.18 | 737 | 2.84 | 1244 | 27.1 |
| 14 | 100 | 5.40 | 941 | 3.17 | 1017 | 30.6 |

TABLE IC

| Example No. | Specific Liquid Movement Force (dyne/den) | Single Fiber Initial Velocity (mm/s) | Fiber Bundle Initial Velocity (mm/s) | Eight Fiber Bundle Maximum Potential Flux ($MPF_B$)* | Single Fiber Maximum Potential Flux ($MPF_{SF}$) |
|---|---|---|---|---|---|
| 1 | 0.0458 | 34.1 | 70.0 | 0.2701 | 0.0210 |
| 2 | 0.0447 | 22.3 | 54.0 | 0.0839 | 0.0154 |
| 3 | 0.0441 | 42.7 | 68.9 | 0.1942 | 0.0607 |
| 4 | 0.0480 | 38.2 | 73.0 | 0.2378 | 0.0334 |
| 5 | 0.0716 | 23.9 | 56.5 | 0.1407 | 0.0194 |
| 6 | 0.0613 | 27.6 | 69.7 | 0.3603 | 0.0246 |
| 7 | 0.0430 | 26.1 | 73.2 | 0.1424 | 0.00981 |
| 8 | 0.0412 | 36.5 | 71.3 | 0.2950 | 0.0219 |
| 9 | 0.0408 | 22.9 | 72.8 | 0.1632 | 0.0593 |
| 10 | — | — | — | — | — |
| 11 | — | — | — | — | — |
| 12 | 0.0515 | 31.9 | 50.0 | 0.0637 | 0.0277 |
| 13 | 0.0723 | 23.2 | 53.2 | 0.1546 | 0.0643 |
| 14 | 0.0729 | 31.3 | 57.6 | 0.19 | 0.10 |

*All bundle MPF values for an 8 (eight) fiber bundle.

TABLE ID

| Example No. | Single Fiber Vertical Rise After 15 Minutes (cm) | Eight Fiber Bundle Vertical Rise After 15 Minutes (cm) | $MPF_B/MPF_{SF}$ | Ratio of Vertical $Rise_B$ to Vertical $Rise_{SF}$ ($VR_B/VR_{SF}$) |
|---|---|---|---|---|
| 1 | 3.65 | 6.04 | 12.80 | 1.66 |
| 2 | 2.58 | 12.90 | 5.46 | 4.98 |
| 3 | 5.85 | 7.88 | 3.20 | 1.35 |
| 4 | 4.51 | 8.91 | 7.12 | 1.98 |
| 5 | 0.83 | 9.74 | 7.25 | 11.70 |
| 6 | 2.85 | 6.64 | 14.70 | 2.33 |
| 7 | 1.71 | 7.45 | 14.50 | 4.36 |
| 8 | 3.83 | 5.19 | 13.40 | 1.36 |
| 9 | 1.49 | 5.96 | 27.60 | 4.00 |
| 10 | — | — | — | — |
| 11 | — | — | — | — |
| 12 | 5.46 | 12.40 | 2.30 | 2.27 |
| 13 | 3.49 | 9.32 | 2.41 | 2.67 |
| 14 | 3.70 | 9.70 | 2.30 | 2.60 |

EXAMPLES

LIQUID ACQUISITION/DISTRIBUTION STRUCTURES

EXAMPLES 15–22

In each of examples 15–22, approximately 25 milliliters (ml) of a textile tint was poured on the center of the structure at about 3 ml/sec. A ½-inch thick layer of cellulose fluff pulp was placed under the flow resistance layer to receive the insult. As shown in Table II, the "best" liquid distributors of the fibers tested in the sense of distributing the liquid uniformly over the length of the fluff were clearly the bundles containing spontaneously wettable fibers. Bundles of fibers of the invention described herein will perform at least as well also.

Table II also shows the actual measurements of the maximum "pumping ability" of the respective bundles as characterized by $MPF_B$ in (cc/den*hr). The specific volume was measured by the method disclosed in U.S. Pat. No. 4,245,001, which is the same as the method disclosed in U.S. Pat. No. 4,829,761. The $MPF_B$ increased dramatically from 0.002 (cc/den*hr) for the round cross section fibers to 0.171 (cc/den*hr) for the spontaneously wettable fibers.

The cross-sections of the fibers of the bundle used in examples 21 and 22 are shown in FIGS. 46A–B. In examples 15–22, a perforated polyethylene film sold under the brand name Dri-Weave® was used as the top layer and the flow resistance layer. It should be noted that bundles of the fibers of examples 1–9 forming the distribution layer in the absorbent article discussed for example 15–22 will function to distribute the liquid reasonably uniformly along the length of the absorbent article.

The properties of examples 15–22 are summarized in Table II.

TABLE II

Properties of Examples 15–22

| Example No. | Cross* Section | dpf | $V_0$ mm/sec | $V_{0_8}$ mm/sec | Specific Volume cc/gm | Maximum Potential Flux* cc/den*hr. | Liquid Distribution in Pulp Underlay |
|---|---|---|---|---|---|---|---|
| 15 | Round | 19.2 | 0 | 22.1 | 0.88 | 0.002 | Almost all the liquid moved into the center ⅓ of the pulp underlay |
| 16 | Round | 30.1 | 0 | 20.6 | 0.88 | 0.003 | Almost all the liquid moved into the center ⅓ of the pulp underlay |
| 17 | FIG. 45B | 20.0 | 3.6 | 33.5 | 1.17 | 0.011 | Some of the liquid was distributed to the outer ⅓ rds of the pulp underlay. |
| 18 | FIG. 45B | 29.9 | 5.0 | 39.1 | 1.18 | 0.013 | Some of the liquid was distributed to the outer ⅓ rds of the pulp underlay. |
| 19 | FIG. 45D | 12.7 | 0 | 37.1 | 1.82 | 0.031 | A significant amount of liquid was moved to the outer ⅓ rds of the pulp underlay. |
| 20 | FIG. 45C | 43.9 | 31.9 | 44.8 | 3.11 | 0.084 | The liquid was distributed reasonably uniformly along the length of the pad. |
| 21 | FIG. 46A | 40.0 | 26.6 | 50.0 | 5.03 | 0.171 | The liquid was distributed reasonably uniformly along the length of the pad. |

TABLE II-continued

Properties of Examples 15–22

| Example No. | Cross* Section | dpf | Vo mm/sec | Vo$_8$ mm/sec | Specific Volume cc/gm | Maximum Potential Flux* cc/den*hr. | Liquid Distribution in Pulp Underlay |
|---|---|---|---|---|---|---|---|
| 22 | FIG. 46B | 6.0 | 13.8 | 22.8 | 1.61 | 0.016 | Some of the liquid was distributed to the outer ⅓ rds of the pulp underlay. |

*Examples 15–18 had ~0.5% LK 5598 - E10 as a surface finish.
Example 19 had ~0.5% LK 1549 E25 as a surface finish, which is __wt. % solids polyethylene glycol (400) monolaurate, __wt. % solids polyethylene glycol (600) monolaurate, and __wt. % solids 4-cetyl, 4-ethyl morpholinium ethosulfate.
Example 20 had ~1.0% LK 5570 E10 as a surface finish, which is 49 wt. % solids polyethylene glycol (400) monolaurate, 49 wt. % solids polyethylene glycol (600) monolaurate, and 2 wt. % solids 4-cetyl, 4-ethyl morpholinium ethosulfate.
**Maximum Potential Flux (MPF$_B$) (cc/(den*hr)) = Vo$_8$ * 8 * 10$^{-4}$ * SV * (1 − 0.7576/SV)

EXAMPLE 23

Example 23 was a repeat of the test conducted in examples 15–22 except that the top sheet and the flow resistance layer were a standard calendar bonded polypropylene nonwoven. Essentially the same results were achieved using the standard calendar bonded polypropylene nonwoven as the top sheet and the flow resistance layer as when the perforated polyethylene film was used.

EXAMPLE 24

Example 24 was also a repeat of examples 15–22 except that a top sheet available from Mölnlycke (i.e., another polymer film) was used for the top sheet and flow resistance layer. Again, similar results were obtained as in examples 15–22.

EXAMPLE 25

Example 25 was a repeat of example 19 except that the flow resistance layer was the polymer film used in example 24. The liquid acquisition/distribution system of example 25 increased the distribution of the liquid toward the outer one third radius of the structure.

EXAMPLE 26

Example 26 is a comparison of performance of hydrophilic surfaces to non-hydrophilic surfaces. The acquisition/distribution of a clean (i.e., uncoated) Dri-Weave® top sheet and clean Dri-Weave® flow resistance layer were compared to the acquisition/distribution structure in which the Dri-Weaves were coated with a very low level of the hydrophilic surface lubricant Pegasperse 200, available from Lonza Inc. of Fairlawn, N.J. The structure with the Pegasperse 200 was clearly superior in its distribution capability than the structure having the clean surfaces.

EXAMPLE 27

Example 27 involved a structure having Dri-Weave® as the top layer and the flow resistance layer, and the distribution layer was a thermal bonded (85% fiber/15% binder powder) 4DG nonwoven fabric. 4DG is the cross-section of the fibers of the bundle of example 22 and are shown in FIG. 46B. The 95.7 gms/meter$^2$ nonwoven was aligned with the machine direction of the nonwoven being parallel to the major axis of the structure. This system distributed the liquid but was not as effective as the structure used in example 19–22.

EXAMPLE 28

The liquid acquisition/distribution structure used in example 28 is shown in FIGS. 47A–B. Notice the 4 cm wide section in the flow resistance layer which is impermeable to flow. This system used the bundle material used in example 21 (shown in FIG. 46A) as the distribution layer and gave excellent distribution of the liquid to the outer one third radius of the structure.

EXAMPLE 29

An absorbent product containing the liquid acquisition/distribution structure used in example 28 is schematically shown in FIGS. 51A–B. Notice the liquid is intended to insult the surface over the small aperture 574. The diameter of the small aperture 574 is 0.5 centimeters. The diameter of the larger apertures 573, 575 are 2.0 centimeters. Upon an insult to the top layer 571 above the aperture 574, the liquid distribution layer 572 substantially uniformly distributes the liquid through the apertures 573, 574, 575 in order to more uniformly communicate the liquid to the absorbent core. The top layer was Dri-Weave®. The distribution layer 572 consisted of a 30,000 denier bundle of the fibers of example 6. The resistance layer 577 was a polyethylene film having the aperture 573, 574, and 575. The structure allowed the liquid to contact the absorbent core 578 at three distinct points to increase the utilization of the absorbent core's material. Obviously, the number of openings, their size, shape (e.g., round, rectangular, crescent, semicircular), and location can be selected to provide the desired distribution of liquid to the core. Each opening should connect the distribution layer to the absorbent core, and should be in communication with the insult region via the distribution layer.

The distribution layer 572 may be a bundle of any of the fibers of examples 1–9. Preferably, the distribution layer 572 comprises a bundle of the fibers of example 6.

Fiber Measurement System

Figure 27:
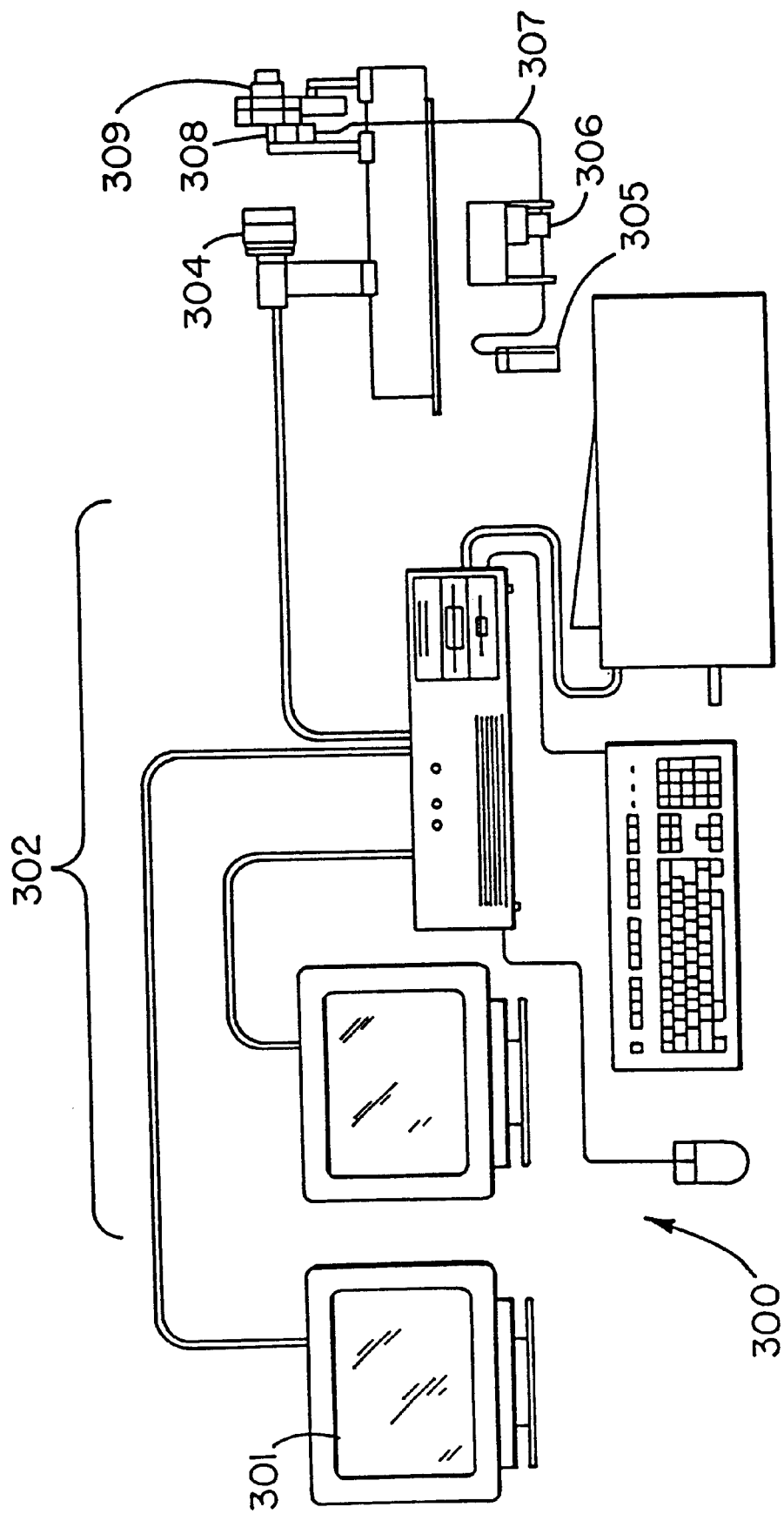
FIG. 27 is a schematic illustrating an image analysis system for use in measuring properties of fibers.

FIG. 27 shows a fiber wetting measurement system 300 useful for determining a liquid's velocity along the fiber or the bundle of fibers. The system 300 includes an image video display 301 for displaying high quality images of liquid-air-solid interfaces moving along the surfaces of the fiber or the bundle of fibers, a computer analysis system generally indicated as 302 including a computer comprising input output devices, a central processing unit, and memory, all of which are functionally interrelated as is well known in the art. The system 300 also includes a liquid reservoir 305 in which there is one end of a tube 307 for transporting the liquid from the liquid reservoir 305, a liquid pump 306 for pumping a metered amount of the liquid from the liquid reservoir 305 through the tube 307 to a fiber retaining mechanism 308. The fiber retaining mechanism 308 positions the fiber or the bundle of fibers retained thereby between the video camera 304 and a means for providing uniform bright field illumination 309. The means for providing the uniform bright field illumination 309 may be a combination of a light homogenizer and a fluorescent ring shaped light source wherein the light homogenizer is between the fiber retaining mechanism 308 and the ring shaped light source.

Figure 28:
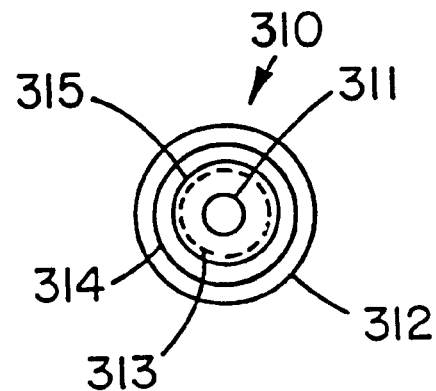
FIG. 28 is a schematic plan sectional view along an axis of a liquid dispensing tip of the imaging system of FIG. 27.

FIG. 28 is a top-sectional view of a liquid dispensing tip 310 for providing a metered amount of liquid to a fiber though the tube 307 shown in FIG. 27. The radii 311–315 are about 0.029 inches, 0.125 inches, 0.063 inches, 0.096 inches, and 0.076 inches, respectively. The metering pump (not shown) provides consistent liquid delivery on demand.

Figure 29:
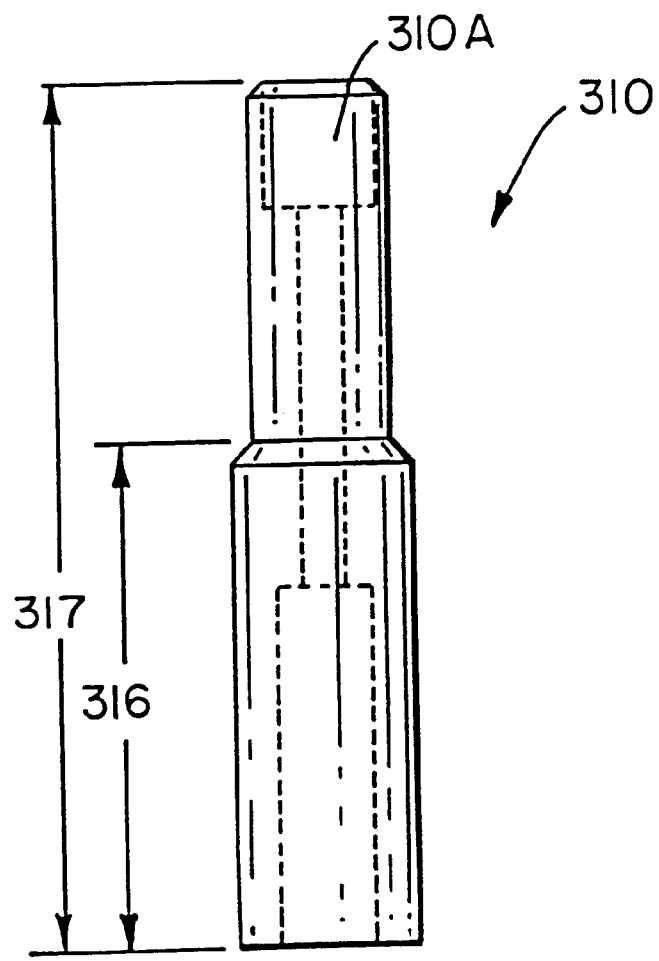
FIG. 29 is a schematic side view of the liquid dispensing tip of FIG. 28.

FIG. 29 is a side-sectional view of dispenser tip 310. The lengths 316 and 317 are about 0.35 and about 0.60 inches, respectively.

The system 300 provides for collection of image data showing the movement of the liquid-air-solid interface along the fiber or the bundle of fibers retained by the retaining mechanism 308. The system 300 provides a means to determine Vo, and therefore a means to determine MPF. The computer analysis system 302 is programmed to identify the liquid-air-solid interface position along the fiber in each frame of image data and to calculate the Initial Velocity, Vo, of the liquid-air-solid interface using that data. Details of the computer program are set forth in the Microfiche Appendix.

The liquid supply to the fiber or the bundle of fibers is controlled by a metering system which includes the liquid pump 306 to provide the desired quantity (a metered amount) of the liquid to a local reservoir 310a of liquid adjacent the fiber or the bundle of fibers. The metering system includes the dispensing tip 310 shown in FIGS. 28 and 29, for receiving the metered amount of the liquid. The arrow at the bottom of FIG. 29 indicates the direction of flow of the metered amount of the liquid from the tube 307 to the local reservoir 310a in the dispensing tip 310.

Figure 52:
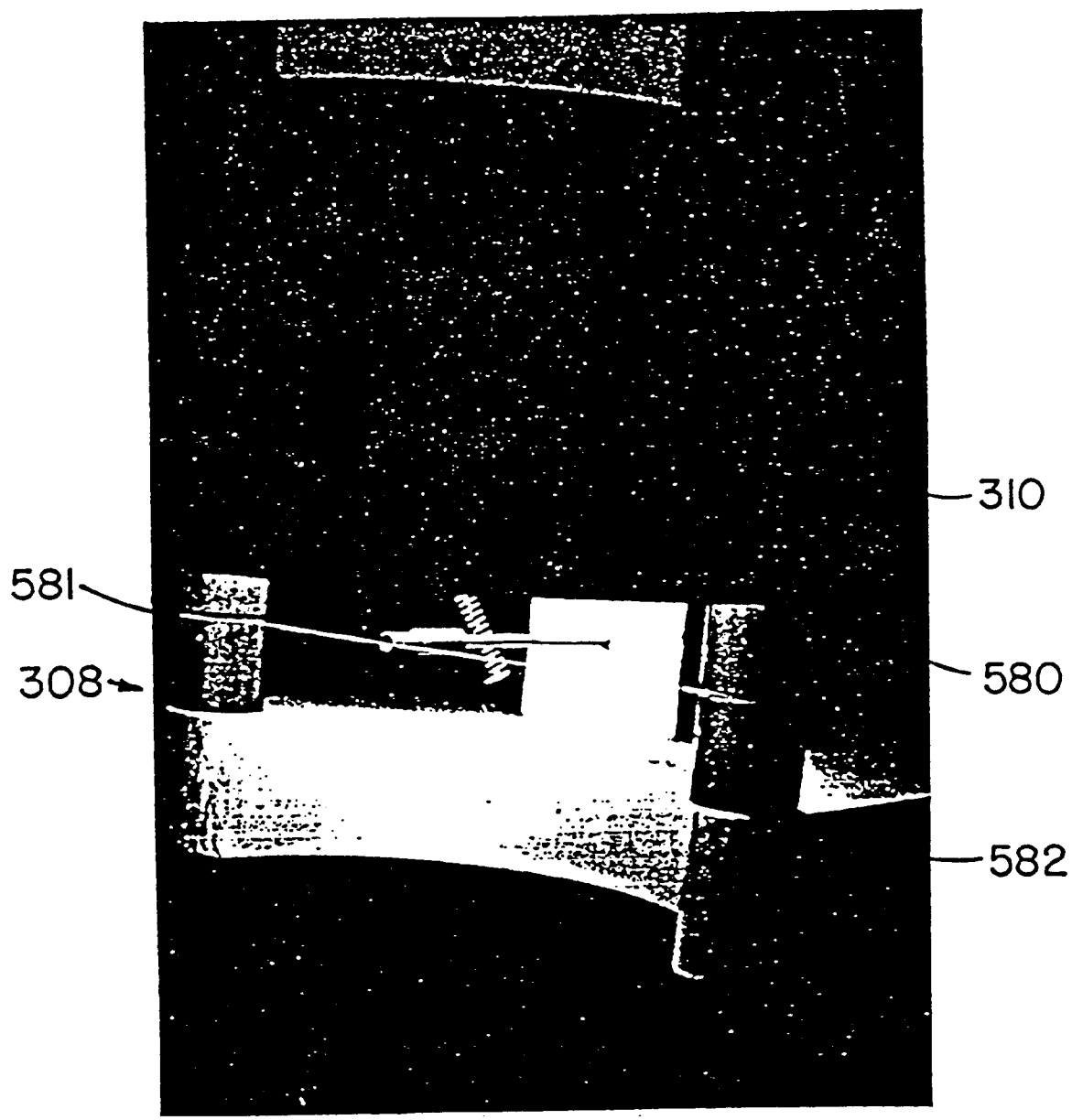
FIG. 52 is a photocopy of a photograph of the fiber retaining mechanism of FIG. 27.

FIG. 52 is a photocopy of a photograph of the fiber retaining mechanism 308 showing the tip 310, the fiber retaining clamps 580, 581, and a fiber 582 retained by the clamps 580, 581. The fiber retaining mechanism 308 retains the fiber 582 adjacent and directly above the center of the local reservoir 310a. (The arrow on the photocopy of the photograph points in the up direction.) The metered amount of the liquid is sufficient to over fill the local reservoir 310a so that the liquid protrudes above the upper surface of the local reservoir 310a and thereby contacts and surrounds the portion of the fiber 582 directly above the local reservoir 310a.

Figure 53:
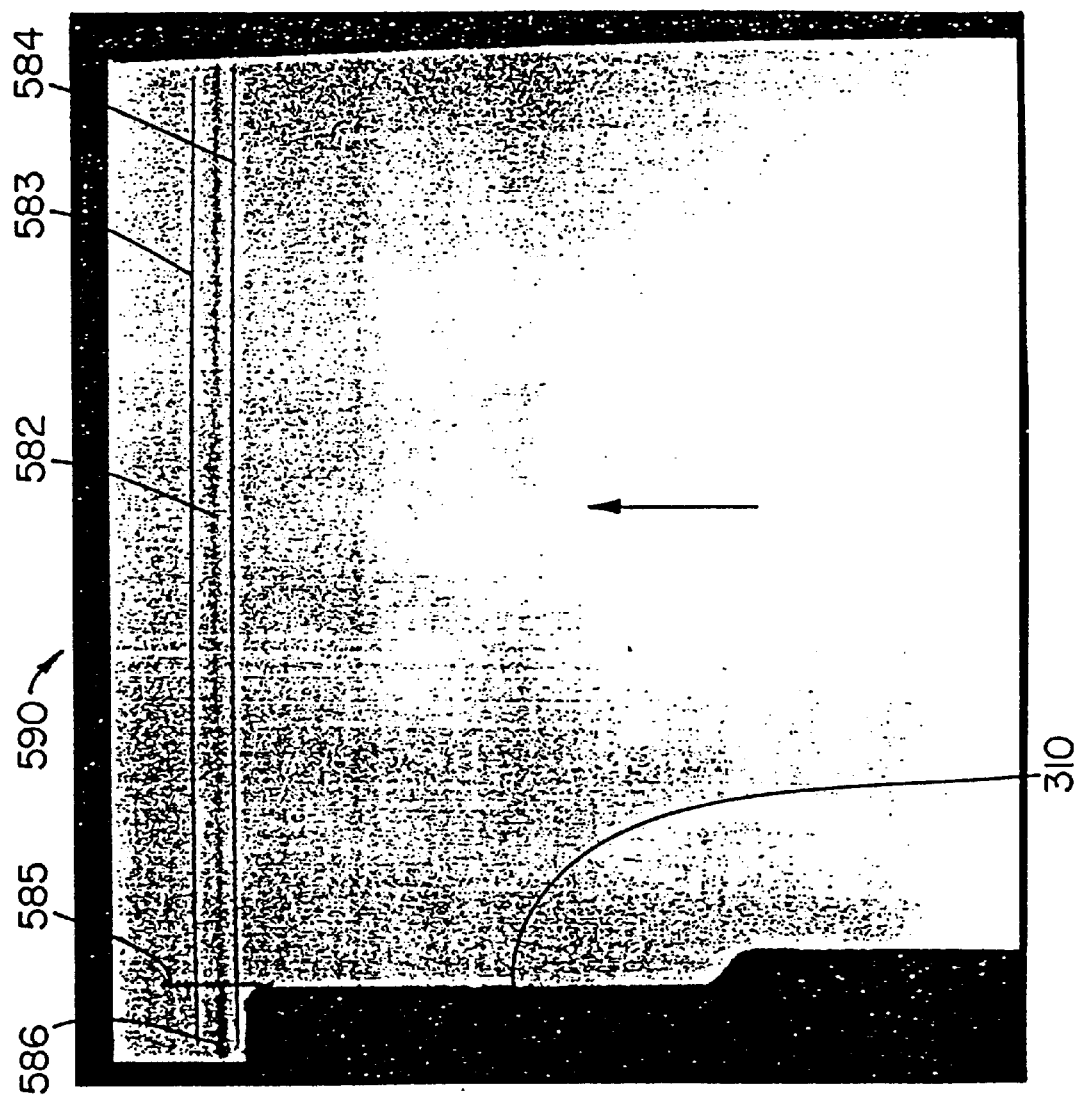
FIG. 53 is a photocopy of a photograph of a video image.

FIG. 53 is a photocopy of a photograph of an image frame 590 generated on the image video 301 by the video camera 304. The image frame 590 shows the fiber 582, the liquid dispensing tip 310, the horizontal lines 583, 584, and the vertical marker line 585. The horizontal lines 583, 584 delimit a visual region of interest or ROI. As shown in FIG. 53, the fiber 582 is suspended so that a portion 586 is directly above the top of the liquid dispensing tip 310. (The arrow on the image frame 590 shows the up direction.)

Figure 54:
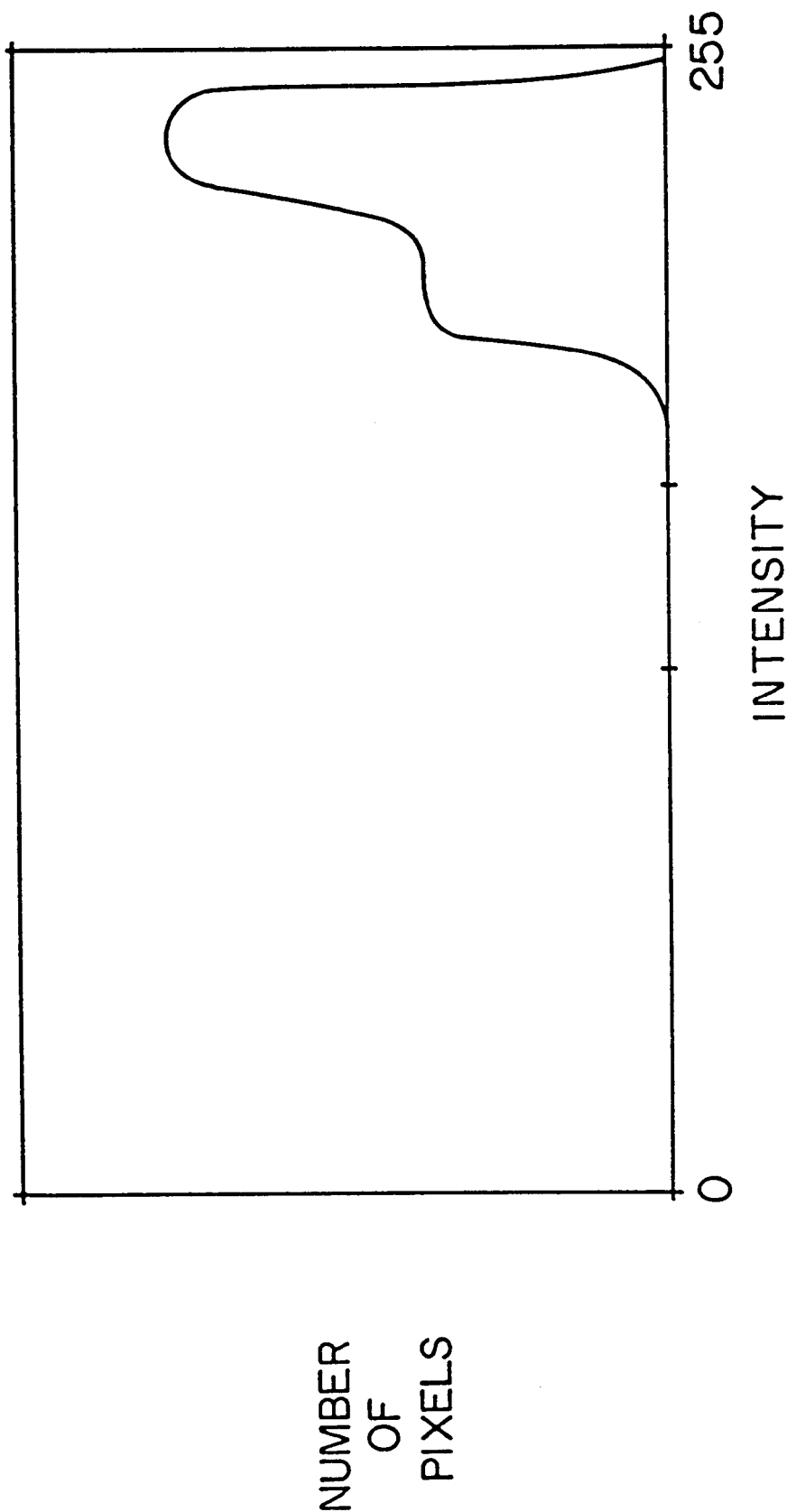
FIG. 54 is a schematic of a histogram of image pixel intensity versus number of pixels.

FIG. 54 is a schematic of the type of histogram generated from the image data for the purpose of setting a threshold for determining when to begin image data collection in the system shown in FIG. 27. The horizontal axis in FIG. 54 identifies a digital value of intensity associated with the light received by a pixel in the video camera 304. The vertical axis in FIG. 54 identifies the number of pixels having each digital value of intensity. Because of the bright field illumination due to the illuminating means 309, all pixels in the ROI have an intensity towards the upper end of the intensity scale. The histogram in FIG. 54 includes data only for the pixels in the ROI between the lines 583, 584.

FIG. 54 also identifies a digital value indicated as the threshold. The threshold is a value that may be graphically determined by the operator of the system shown in FIG. 27. The threshold is set to an intensity value that is below the lowest digital value for intensity of any pixel in the ROI and above the digital value for the intensity at a location of the fiber or the bundle of fibers when the fiber or the bundle of fibers is wetted by the liquid in the reservoir.

Figure 55:
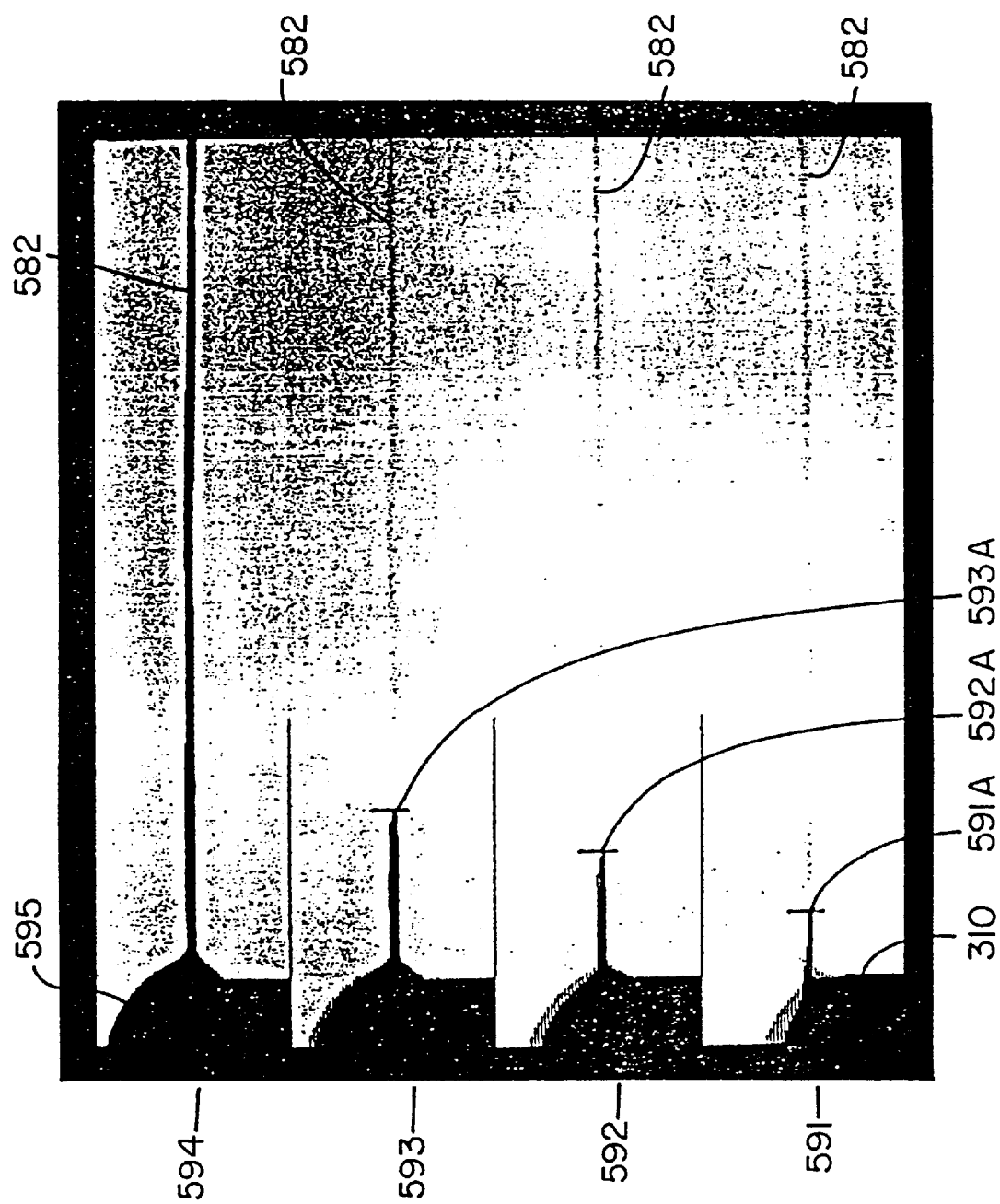
FIG. 55 is a photocopy of a photograph of a video image of a region of interest at four different times.

FIG. 55 consists of four images of the ROI 591–594 at different times. Images 591–594 are sequential in time, showing the movement of the liquid-air-solid interface from where the liquid contacts the fiber or the bundle of fibers along the fiber or the bundle of fibers. The ROI 591 shows the liquid air interface 591a. The ROI 592 shows the liquid-air-solid interface 592a. The ROI 593 shows the liquid-air-solid interface 593a. In the ROI 594, the liquid-air-solid interface is beyond the right end edge of FIG. 55. The convex meniscus 595 forming the liquid-air interface above the liquid dispensing tip 310 is shown in the ROI 594.

Figure 56:
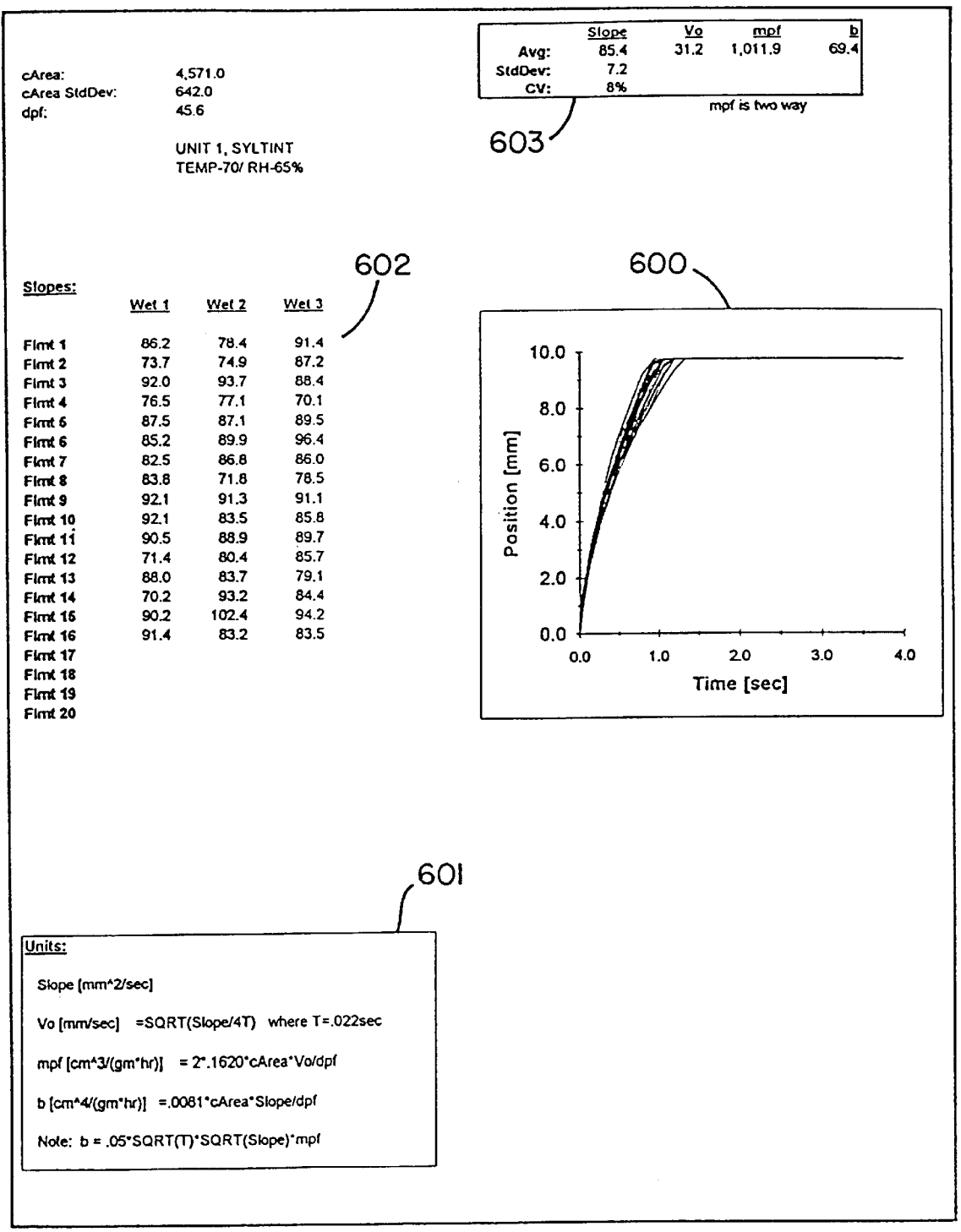
FIG. 56 is a photocopy of a photograph of a video image including various data relating to liquid flux calculations.

FIG. 56 shows a video image including a graph 600, formula used for calculating values 601, data from a series of tests 602, and calculated values 603 based upon the experimental results shown in the graph 600. The graph 600 is a graph of position versus time for the location of the liquid-air-solid interface along the length of the fiber 582.

Use of the Fiber Measurement System

The Vo determination includes the following general procedure. A tensioned (≈0.1 g/d) fiber or bundle is mounted to the fiber retaining mechanism 308 in a predetermined location within the field of view of the video camera 304. A fixed metered volume of test liquid (i.e. Syltint® Red or Red Test Solution) is brought into contact with the bundle. The fixed volume of liquid used for a single fiber measurement (as opposed to a bundle measurement) is 0.00677 milliliters$^3$. (This volume of liquid was provided in the system 300 by setting the metering pump liquid volume setting to 115.) Data from thirty digital video frames per second are recorded in the computer 302's memory for a period of four seconds. The slope of the line defined by the square of the distance traveled by the liquid front versus time is determined. A least squares fit or similar procedure may used to determine a value for the slope, or the slope may be estimated from a plot of the data. From this slope, the initial liquid velocity Vo is calculated using the formula:

$$Vo(\text{mm/sec}) = [\text{Slope}(\text{mm}^2/\text{sec})/(4*0.022 \text{ sec})]^{1/2}.$$

The capillary channel area for flow and the denier per filament (dpf) are determined. The capillary channel area for flow is determined as described herein. It is well known in the art how to determine the denier of the fiber.

From Vo, dpf, and capillary channel area for flow, the (two-way) MPF$_{SF}$ in cubic centimeters per gram per hour is calculated as:

$$\text{Two-way } MPF_{SF}(\text{cc/gm*hr}) = 2*0.1620*Vo(\text{mm/sec})*(\text{capillary channel area for flow (microns}^2))*(1/\text{dpf})$$

The arbitrary length of the fiber used in the above formula is 20 centimeters. Thus, the weight in grams of the fiber is the weight of a 20 cm long piece of the fiber.

The "two-way" calculation accounts for the fact that the liquid moves along the fiber in both directions even though Vo is determined only on one side of the drop contact, which is why the two-way MPF definition includes a factor of two. These measurements and calculations are conducted on a sufficient number of filaments to develop statistically sound data. Typically for a given type of fiber (i.e., a fiber produced from a spinnerette aperture under a set of conditions), twenty pieces of the fiber are cut and three measurements of the initial liquid velocity are made on each of the piece of the fiber, for a total of sixty measurements. The average of the 60 measurements (or wets) is used to determine Vo.

The 20 cm length used to calculate $MPF_{SF}$ is quite arbitrary although it is the approximate length of a feminine napkin. After serious consideration the inventors believe that a more standard unit system for MPF is cubic centimeter per denier per hour cc/(den*hr) instead of cc/(gm*hr). The units of conversion from cc/(gm*hr) to cc/(den*hr) changes the length in the equation for MPF from 20 cm to 9,000 meters, because 9,000 meters is the standard length for the denier unit. All of the MPF values reported herein are in cc/(den*hr) unless otherwise stated. The conversion of MPF (cc/gm*hr.) to MPF (cc/den*hr.) is accomplished by the following equation:

$$MPF(cc/gm\ hr)*(20\ cm/900,000\ cm)=MPF(cc/gm*hr)*(1/45,000)=MPF(cc/den*hr)$$

Thus dividing by 45,000 converts to MPF from cc/(gm*hour) to cc/(den*hr).

During the procedures for determining the values for MPF of a fiber or of a bundle of fibers care is taken to avoid stretching the fibers, to avoid crimps in the fiber, to avoid separation of wetting liquid in the pumping system, to maintain room temperature (21.1° C.) and normal humidity (65% Relative Humidity) thereby avoiding condensation, to maintain sufficient optical contrast to be able to observe the position of the liquid on the fiber, to avoid movement of the fiber during the measurements, and to avoid contamination of the fibers.

From time to time it is necessary to calibrate the metering pump to ensure that a given scale setting on the pump corresponds to a known delivered volume of liquid. This can be accomplished by setting a series of several pump scale settings (say 100, 200, 300, 400), manually pulsing the pump a large number of times at each of these settings (say 400, 200, 150, 100 times, respectively), and diverting the Syltint discharge of the pump into a calibrated 10 ml glass cylinder. The volume of liquid collected at each setting is divided by the number of pulses (strokes) used at that setting to calibrate the metering pump setting to the volume of liquid delivered at that setting.

The video scale of the system 300 should also be calibrated to ensure that the lengths automatically determined in the computer based upon the image data correspond to physical lengths. The video scale should be calibrated when a change has been made in the video camera or in the lighting system, such as a change in the video camera's position or focus. The video calibration may be accomplished by placing a ruler in the location of the fiber sample holder so that a ten centimeter section is in the field of view and adjusting the external light source so that the ruler divisions are clearly visible. The ten centimeter length of the ruler can be defined in the image data and the computer's variables identifying the scale may be adjusted so that the computer's calculations define the centimeter section of the ruler as ten centimeters.

Determination of the Initial Velocity of liquid along the bundle is very similar to the determination of the Initial Velocity of liquid along the single fiber. The primary difference is that measurements are made upon a bundle of fibers grouped together rather than a single fiber. The test is performed using the same system 300 used for single fibers. Differences between measurements of single fibers and bundles of fibers are described below.

Sample preparation for use in the system 300 of a bundle of fibers includes separating single fibers from a ninety centimeter long full yarn strand and then combining the individual fibers into an 8 fiber bundle of essentially parallel fibers.

The weights for tensioning are clipped to each end of the ninety centimeter long bundle to produce a bundle tension of about 0.1 gm/denier on the bundle (based on the total denier of the bundle). The bundle is placed in and on top of the fiber mounting grooves of the mounting system in a manner to keep the fibers grouped as close together and as parallel as practical.

Measurements are made on three separate locations on each ninety centimeter long bundle. Measurements are obtained from approximately 20 bundles for a total of sixty wets.

A volume of liquid of 0.013984 ml for a bundle of eight 50 dpf fibers and a volume of liquid of 0.033198 ml for a bundle of eight 150 dpf fibers was metered. The volume of liquid that is metered may be determined in accordance with the metering of liquid described for measuring individual fibers. Generally, the amount of liquid metered per measurement is a constant plus a volume linearly proportional to the dpf of the fibers of the bundle. However, the exact amount of liquid metered per measurement is not critical.

The use of the system 300 for determining the maximum potential flux (MPF) and the Initial Velocity (Vo) is described hereinbelow in the discussion of FIGS. 57–60. One embodiment of a computer program for determining MPF is set forth in the Microfiche Appendix.

Figure 57:
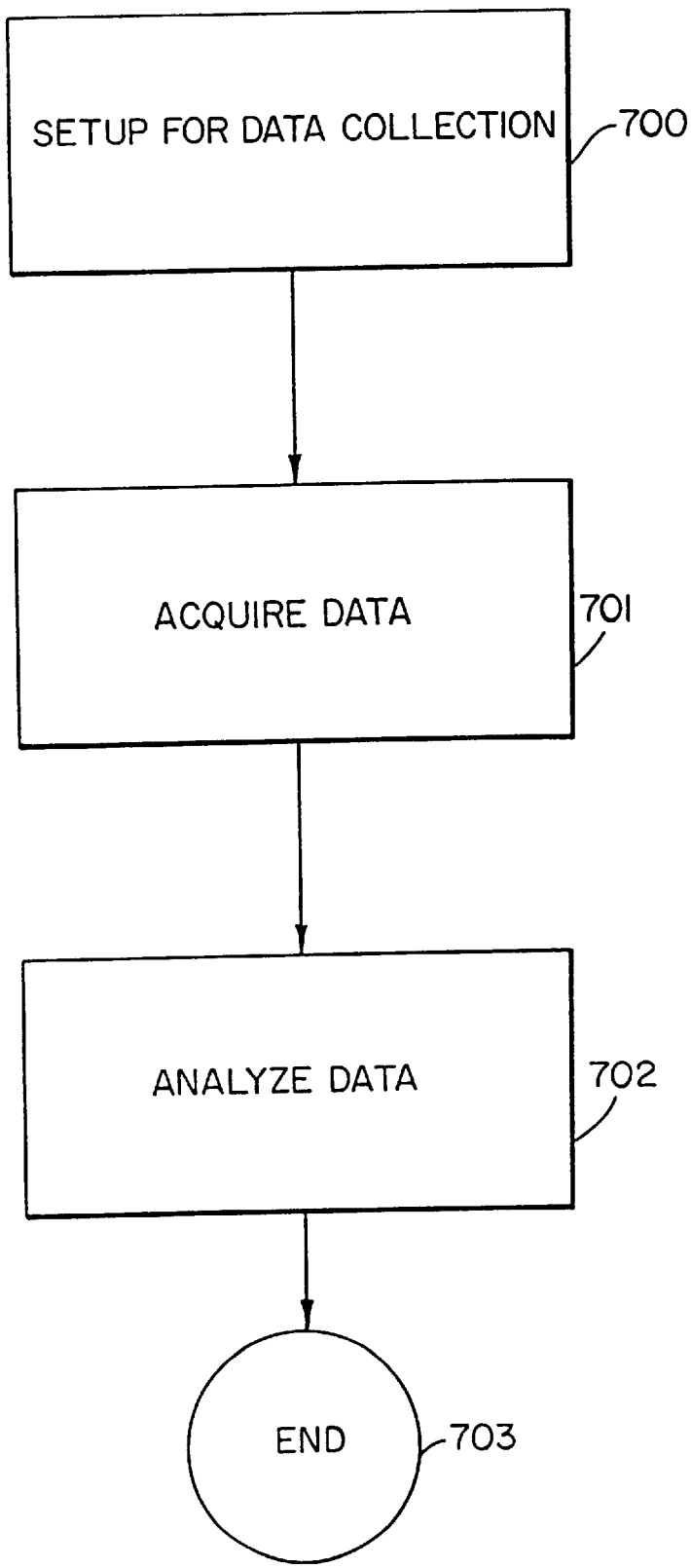
FIG. 57 is a flowchart showing an overview of algorithms for determining MPF and $V_0$.

FIG. 57 is a flowchart showing an overview of the algorithm for calculating MPF and Vo using the system 300 shown in FIG. 27. That algorithm includes the sub-algorithm 700 for setting up the system 300 for data collection, the sub-algorithm 701 for acquiring data, the sub-algorithm 702 for analyzing data, and the end of the routine 703.

Figure 58:
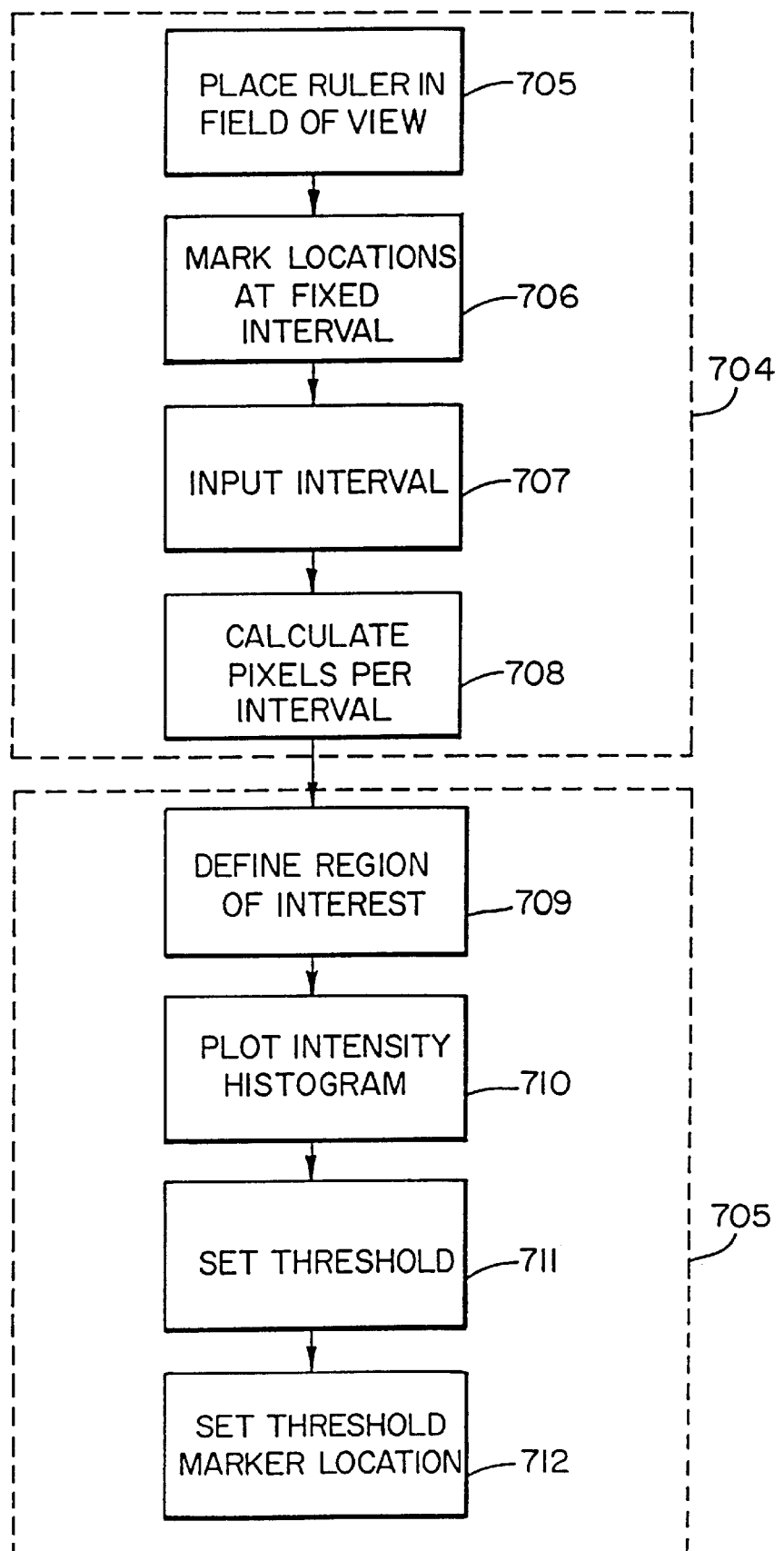
FIG. 58 is a flowchart showing an algorithm for setting up for data collection.

FIG. 58 shows the sub-algorithm 700 for setting up for data collection which includes the scale determining algorithm 704 and the threshold setting algorithm 705.

The scale determining algorithm 704 includes the step 705 of placing a ruler in the field of view at the same distance from the video camera 304 as the fiber 582. In step 706, two points defining an interval along the image of the ruler appearing in the image video 301 are marked with graphical markers controlled by a graphical interface, such as a mouse. In step 707, the actual interval between the two points is read from the indicia on the image of the ruler and input into the computer via the keyboard. The computer runs an algorithm to determine the number of pixels spanning the interval defined by the two points. In step 708, the computer calculates the number of pixels per length by dividing the determined number of pixels spanning the interval by the length of the interval, thereby determining the scale of the image of the fiber or the bundle of fibers 582.

The purpose of the algorithm 705 for setting the threshold is to enable the computer to automatically recognize and locate the liquid-air-solid interface, and to thereby measure the advancement of the liquid along the length of the fiber or the bundle of fibers. In step 709, the user defines the region of interest, ROI, which is the region in the video image containing the image of the fiber. The ROI in FIG. 53 is limited to the region between the two lines 583, 584. In step 710, the computer is instructed to plot a histogram of the number versus the digitized pixel intensity for the pixels in the region of interest and display the plot on the image video 301.

Since the system 300 includes the bright field background provided by the means 309, all of the pixels have an intensity towards the upper end of the scale. This is why the histogram shown in FIG. 54 has intensity only towards the upper end of the digitized intensity scale. The shoulder in the histogram appearing in FIG. 54 towards lower intensity represents the decrease in intensity for the pixels imaging the fiber 582 shown in FIG. 53 relative to the bright background. The decreased intensity is because the fiber blocks or scatters some of the light. Based upon the data in the histogram, an intensity below the intensity of the pixels that are present in the ROI is defined as the threshold. The intensity of the threshold is set below the intensity of any pixel in the ROI and above the intensity of the image of the fiber when the fiber is wetted by the liquid.

Setting the threshold is step 711. In step 712, the marker location for the threshold is set. FIG. 53 shows the marker location 585 for the threshold. The marker location for the threshold is set laterally displaced from the region of the fiber immediately above the liquid dispensing tip 310 so that the threshold (1) will not be triggered by the formation of the convex meniscus of the liquid protruding up from the reservoir of the liquid dispensing tip 310 but (2) will be triggered when the liquid begins propagating along the fiber or the bundle of fibers thereby crossing the marker location 585.

The threshold and the marker location for the threshold are used to begin data collection and to extrapolate when the liquid contacts the fiber. Data collection begins when the intensity of the pixel (or average intensity of the pixels, if a group of pixels is used) at the marker location falls below the threshold value. The intensity of the pixel or pixels at the marker location falls below the threshold value when the liquid covers the fiber or the bundle of fibers at the marker location. Since the marker location is immediately adjacent to the liquid dispensing tip 310, and since the fiber or bundle of fibers are spontaneously transporting, the liquid covers the fiber at the marker location very shortly after the liquid contacts the fibers. By extrapolation from the data of liquid-air-solid interface versus time, it appears that the liquid covers the marker location along the fiber in no more than a few milliseconds. Since the system 300 records a new image frame every thirtieth of a second, the time at which the intensity at the marker location falls below the threshold is a good approximation to the time when the liquid contacts the fiber.

FIG. 55 shows a display on the image video 301 reconstructing four images 591–594 of the ROI at four consecutive times. Image 591 shows the liquid-air-solid interface 591a at a position along the fiber or bundle of fibers 582 that is relatively close to the top of the liquid dispensing tip 310 as compared to the liquid-air-solid interface positions 592a and 593a in the images 592 and 593 that occur sequentially at subsequent times. Image 594 shows the fiber or bundle of fibers 582 in ROI entirely coated with the liquid. The metered amount of liquid is sufficient to fill the local reservoir of the liquid dispensing tip 310 such that the liquid projects up from the from the rim of the reservoir of the tip and forms a meniscus 595 having a positive curvature such that the liquid extends around the fiber or the bundle of fibers.

Figure 59:
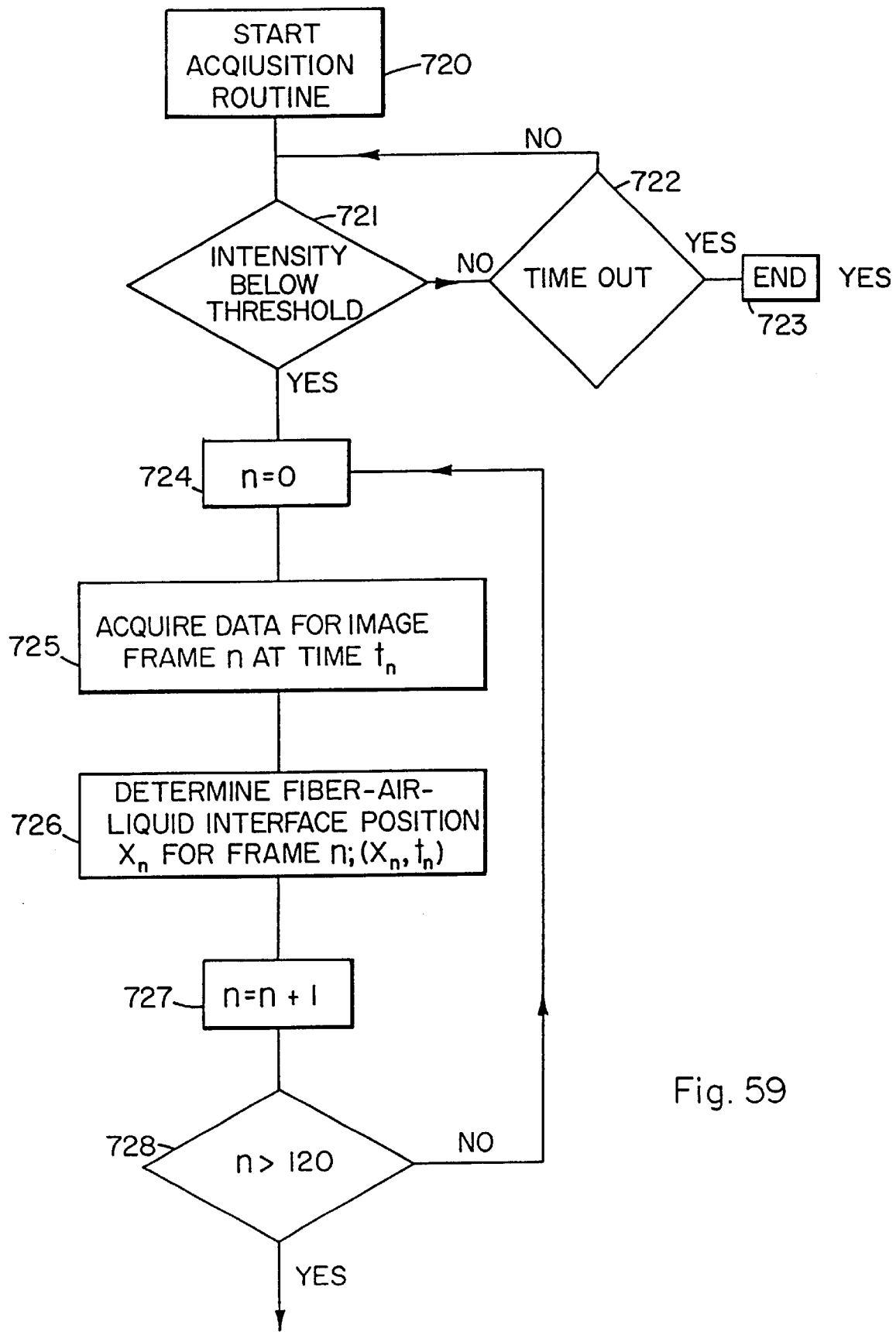
FIG. 59 is a flowchart showing an algorithm for acquiring data.

FIG. 59 shows the algorithm for acquiring data using the system 300. Data acquisition is initiated after the system has been set up for data collection using the algorithm shown in FIG. 58. However, it should be noted that the recalibration of the scale and the resetting of the threshold each time the system is used are advisable, but not essential.

In step 720, the system is instructed to begin the data acquisition. In step 721, the system compares the intensity at the threshold marker location with the threshold. If the intensity is not below the threshold, the system executes step 722 to determine if a timeout has occurred. If a timeout has occurred, the system ends the data acquisition in step 723. If a timeout has not occurred, pursuant to step 722, the system repeats the comparison in step 721.

If, in step 721, the system 300 determines that the intensity at the marker location is below the threshold intensity, the system 300 sets a running variable n=0 in step 724.

Next, in step 725, the system acquires data for the image frame n at the time $T_n$. Next, in step 726, the system examines the data in the ROI to determine the location, $X_n$, of the liquid-air-solid interface for image frame n. The system records the location of the liquid-air-solid interface and the time of the image frame n ($X_n$, $T_n$).

Next, in step 727, the system 300 increments the value of n by 1. Next, in step 728, the system determines whether n is greater 120. If n is not greater than 120, the system returns to step 725 and acquires the next image frame. The system is set so that the time between image frames is ⅓₀th of a second (0.033 seconds). Therefore, when n=120, the system has been acquiring data for approximately four seconds.

If, in step 728, n is greater than 120, the system does not return to step 729 to acquire more data.

Figure 60:
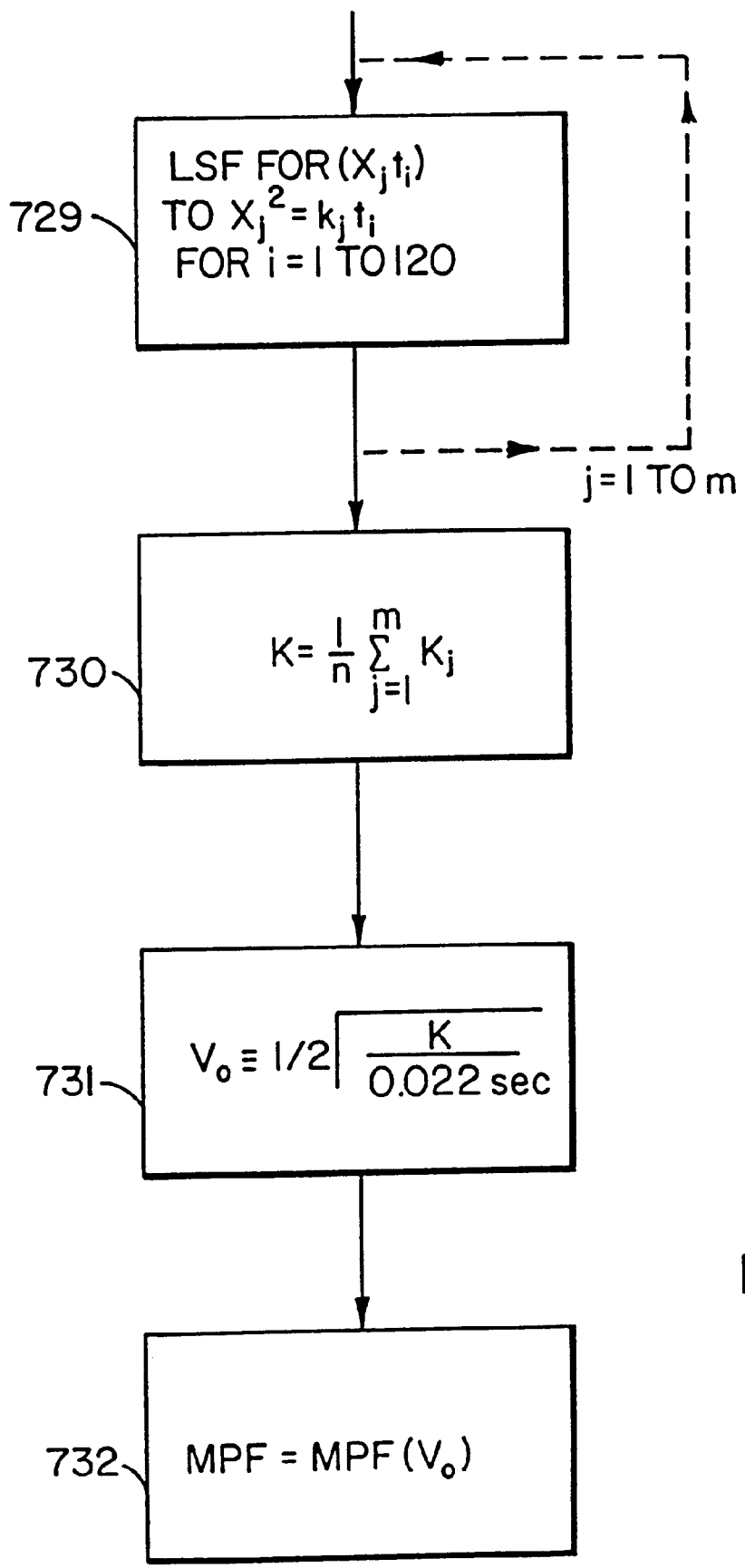
FIG. 60 is a flowchart showing an algorithm for calculating MPF and $V_0$ based upon acquired data.

When n exceeds 120, the data acquisition for the wetting of the fiber or the bundle of fibers ends. At this point, the operator can start the data acquisition routine again after moving the fiber or the bundle of fibers to a location so that the dispensing tip 310 is not adjacent a wet region of the fiber or the bundle of fibers. Alternatively, the operator can instruct the system to begin the analysis of the data for some set, j, of acquired data $(X_i, T_i)_j$. (The subscript i refers to different data during a single wetting. The subscript j refers to data for different wettings.) In any case, when several data sets for several distinct wettings of the fiber or bundle of fibers have been recorded, the algorithm for calculating the Initial Velocity Vo and the Maximum Potential Flux MPF is executed. That algorithm is shown in FIG. 60.

In step 729, the system performs a curve fit for the 120 pairs of values for the position of the liquid-air-solid interface at the times T to the equation $X^2$ equals a constant, K, times the time, T. ($X_i^2 = K_j * T_i$ for i=1 to 120 and for a specified integral value of j.) Step 729 is performed for each of the data sets, j, that has been acquired for a particular fiber or bundle of fibers. That is, position versus time of the liquid-air-solid interface is acquired at multiple locations along a single fiber or bundle of fibers, or is acquired along different segments of the same type of fiber. Each set of data points (X, T) is fit to the foregoing formula in order to determine a value of $K_j$ for the jth wetting of the fiber or the bundle of fibers.

Next, in step 730, an average value of K is determined. The average value of K is the average of all $K_j$ values obtained in step 729 for the same type of fiber or the bundle of fibers. In this context, the same type means fibers or bundles of fibers formed using the same process as one another and thereby nominally having the same cross-sectional shape and surface composition.

Next, in step 731, the parameter Vo (Initial Velocity) is calculated as Vo=one half of the quantity of the square root of K in square centimeters per second ($cm^2$/sec) divided 0.022 seconds. The quantity Vo is termed the Initial Velocity because it approximates the velocity that the liquid would have at 0.022 seconds after the liquid first contacts the fiber or the bundles of fibers. That approximation is based upon a physical model balancing forces between the driving force and the velocity-proportionally viscous force. That is, the model (which results in the equation of motion $X^2$=KT) is an approximation assuming a solution to the equation of motion for the liquid that ignores inertial terms. Note that actual gravitational forces do not exist along the length of the fiber or the bundle of fibers because the fiber or the bundle of fibers are held horizontal during the measurements. The value for time of 0.022 seconds after the time of which the optical intensity falls below threshold at the marker location in step 721 is in the definition of Vo because that time is long enough after the actual time at which the liquid contacts the fiber that differences between the model's velocity Vo and the actual velocity at t=0.022 seconds are insignificant. In this context, insignificant means that the difference is less than about ten percent.

Finally, in steps 732, the MPF, which is a function of Vo and predetermined quantities, is calculated.

Red Test Solution: Composition and Preparation

In preparing a sample of Red Test Solution, components (a) through (g) comprising
- (a) 80.3 grams (0.414 moles) dimethyl isophthalate,
- (b) 26.9 grams (0.091 moles) dimethyl-5-sodiosulfoisophthalate,
- (c) 54.1 grams (0.51 moles) diethylene glycol.
- (d) 37.4 grams (0.26 moles) 1,4-cyclohexanedimethanol,
- (e) 0.75 grams (.0091 moles) anhydrous sodium acetate,
- (f) 100 ppm Titanium catalyst as titanium tetraisopropoxide, and
- (g) 15.0 grams (0.037 moles) of red colorant

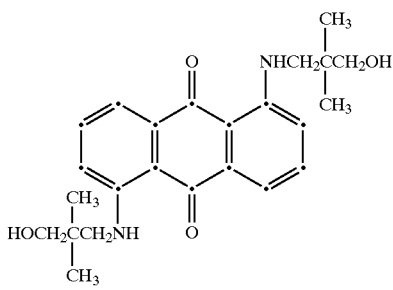

are added to a 50 mL round bottom flask. The flask is fitted with a stirrer, condensate take off and nitrogen inlet head. The flask and contents are immersed into a Belmont metal bath and heated for two hours at 200–220° C. while ester interchange occurs. To carry out the polycondensation reaction, the temperature is increased to about 250° C. and the flask is held under vacuum $\leq 0.5$ mm Hg for about 20 minutes. A dark red polymer is produced which is granulated by grinding in a Wiley mill.

The dark red polymer is a water dispersible polymer containing 10 percent by weight of the red colorant. The dark red polymer has an IV of 0.235, a $T_g$ at 57.51° C., a weight average molecular weight of 12,728, a number average molecular weight of 5,035 by Gel Permeation Chromotography and a polydispersity value of 2.53.

After granulation, slowly add 100 grams of the dark red polymer granules to 250 mls of boiling millipore water. The water is then slowly cooled with stirring until the dispersion is uniform so no solid residue remains. The resulting dispersion weighs 333 grams which is equivalent to 30 percent by weight of the dark red polymer in millipore water. Add 10 mls of the 30 percent by weight dispersion to an equal portion of millipore water to make a 50/50 dispersion. Add 10 mls of the 50/50 dispersion to 5 mls of distilled water to make the final test solution which is a 90/10 water/red polymer dispersion.

The Red Test Solution while appearing to be very stable, should be stirred or mixed thoroughly once a month to insure a uniform test fluid. The Red Test Solution has a shear viscosity of 1.5 centipoise and a surface tension of 56 dynes/cm.

Note that any aqueous fluid with sufficient color contrast and viscosity less than 3 centipoise could have been used as the test fluid. However, the results for MPF depend strongly on the surface tension and the viscosity of the test fluid. Thus, if an aqueous fluid with higher surface tension and equal viscosity to the test fluids above is used, the MPF numbers will be larger for a given fiber test sample. If an aqueous fluid with a higher viscosity and equal surface tension to the test fluids above is used, the MPF numbers will be smaller.

Obviously, numerous modifications and variations of the present invention are possible in light of the above teachings. It is therefore to be understood that within the scope of the appended claims, the invention may be practiced otherwise than as specifically described herein.

What is claimed as new and useful is:

1. A bundle of synthetic fibers for transporting non-polar fluids, wherein the bundle comprises at least two fibers, at least one of said two fibers having
   (A) a non-round cross-section;
   (B) a Single Fiber Bulk Factor greater than 4.0;
   (C) (i) a Specific Capillary Volume less than 2.0 cc/gm or a Specific Capillary Surface Area less than 2000 cc/gm, and (ii) more than 70% intra-fiber capillaries having a channel width greater than 300 microns; and
   (D) a hydrophobic surface composition.

2. The bundle of synthetic fibers of claim 1 having an average inter-fiber capillary width of from 25 to 400 microns.

3. The bundle of synthetic fibers of claim 1 wherein the cross-section and the surface composition of the fibers satisfy the inequality: $(P\gamma \cos(\theta a))/d > 0.03$ dynes/den,
   wherein P is the perimeter of the cross-section of the fiber, $\gamma$ is the surface tension of the liquid, ($\theta a$) is the advancing contact angle of the liquid measured on a flat surface made from the same material as the fiber and having the same surface treatment and d is the denier of the fiber.

4. The bundle of synthetic fibers of claim 1 wherein said cross-section of said fiber defines a first arm having a length greater than 40 microns.

5. The bundle of synthetic fibers of claim 4 wherein said first arm has a length greater than 100 microns.

6. The bundle of synthetic fibers of claim 1 wherein said Single Fiber Bulk Factor is between 4.0 and 10.0.

7. The bundle of synthetic fibers of claim 1 wherein said Specific Capillary Volume is between 0.0 and 1.5 cc.

8. The bundle of synthetic fibers of claim 7 wherein said Specific Capillary Volume is between 0.0 and 1.0 cc.

9. The bundle of synthetic fibers of claim 1 wherein said Specific Capillary Surface Area is less than 1500 cc/gm.

10. The bundle of synthetic fibers of claim 1 wherein said fibers each have a denier between 15 and 250.

11. The bundle of synthetic fibers of claim 10 wherein said fibers each have a denier between 30 and 170.

* * * * *